(12) United States Patent
Clark et al.

(10) Patent No.: US 8,598,154 B2
(45) Date of Patent: Dec. 3, 2013

(54) PYRIDYL-AMINE FUSED AZADECALIN MODULATORS

(75) Inventors: Robin Clark, Kaleheo, HI (US); Tony Johnson, Harlow (GB); Hazel Hunt, Harlow (GB); Ian McDonald, Harlow (GB)

(73) Assignee: Corcept Therapeutics, Inc., Menlo Park, CA (US)

( * ) Notice: Subject to any disclaimer, the term of this patent is extended or adjusted under 35 U.S.C. 154(b) by 0 days.

(21) Appl. No.: 13/218,809

(22) Filed: Aug. 26, 2011

(65) Prior Publication Data

US 2012/0220565 A1    Aug. 30, 2012

Related U.S. Application Data

(60) Provisional application No. 61/377,558, filed on Aug. 27, 2010.

(51) Int. Cl.
| *A61K 31/5383* | (2006.01) |
| *A61K 31/437*  | (2006.01) |
| *A61K 31/496*  | (2006.01) |
| *A61K 31/5377* | (2006.01) |
| *C07D 471/14*  | (2006.01) |
| *C07D 498/04*  | (2006.01) |

(52) U.S. Cl.
USPC ........... 514/210.21; 514/230.4; 514/232.8; 514/253.03; 514/293; 544/105; 544/126; 544/361; 546/82

(58) Field of Classification Search
None
See application file for complete search history.

(56) References Cited

U.S. PATENT DOCUMENTS

| 7,678,813 B2 | 3/2010 | Clark et al. |
| 7,928,237 B2 | 4/2011 | Clark et al. |
| 2007/0281928 A1 | 12/2007 | Clark et al. |

FOREIGN PATENT DOCUMENTS

| EP | 0375210 A1 | 6/1990 | |
| WO | WO 03/015692 A2 | 2/2003 | |
| WO | WO 2005087769 A1 * | 9/2005 | ........... C07D 471/04 |

OTHER PUBLICATIONS

Clark et al., 1H-Pyrazolo[3,4-g]hexahydro-isoquinolines as Selective Glucocorticoid Receptor Antagonists with High Functional Activity, 18 Bioorg. & Med. Chem. Letts. 1312-1317 (2008).*
International Search Report and Written Opinion dated Jan. 30, 2012, issued in related International Patent Appln. No. PCT/US11/49408, filed Aug. 26, 2011.
Clark et al., "1*H*-Pyrazolo[3,4-g]hexahydro-isoquinolines as selective glucocorticoid receptor antagonists with high functional activity," 2008, Bioorganic & Medicinal Chemistry Letters, 18, pp. 1312-1317.

* cited by examiner

*Primary Examiner* — Janet Andres
*Assistant Examiner* — Timothy R Rozof
(74) *Attorney, Agent, or Firm* — Kilpatrick Townsend & Stockton LLP.

(57) ABSTRACT

The present invention provides a novel class of pyridyl-amine fused azadecalin compounds and methods of using the compounds as glucocorticoid receptor modulators.

19 Claims, 4 Drawing Sheets

PYRIDYL-AMINE FUSED AZADECALIN MODULATORS

CROSS-REFERENCES TO RELATED APPLICATIONS

This application claims priority to U.S. Provisional Application No. 61/377,558, filed Aug. 27, 2010, which is incorporated in its/their entirety herein for all purposes.

BACKGROUND OF THE INVENTION

In most species, including man, the physiological glucocorticosteroid is cortisol (hydrocortisone). Glucocorticosteroids are secreted in response to ACTH (corticotropin), which shows both circadian rhythm variation and elevations in response to stress and food. Cortisol levels are responsive within minutes to many physical and psychological stresses, including trauma, surgery, exercise, anxiety and depression. Cortisol is a glucocorticosteroid and acts by binding to an intracellular, glucocorticoid receptor (GR). In man, glucocorticoid receptors are present in two forms: a ligand-binding GR-alpha of 777 amino acids; and a GR-beta isoform which lacks the 50 carboxy terminal amino acids. Since these include the ligand binding domain, GR-beta is unable to bind ligand, is constitutively localized in the nucleus, and is transcriptionally inactive. The glucocorticoid receptor, GR, is also known as the glucocorticoid receptor II, or GRII.

The biologic effects of cortisol, including those caused by hypercortisolemia, can be modulated at the GR level using receptor modulators, such as agonists, partial agonists and antagonists. Several different classes of agents are able to block the physiologic effects of GR-agonist binding. These antagonists include compositions which, by binding to GR, block the ability of an agonist to effectively bind to and/or activate the GR. One such known GR antagonist, mifepristone, has been found to be an effective anti-glucocorticoid agent in humans (Bertagna (1984) *J. Clin. Endocrinol. Metab.* 59:25). Mifepristone binds to the GR with high affinity, with a dissociation constant ($K_d$) of $10^{-9}$ M (Cadepond (1997) *Annu. Rev. Med.* 48:129).

Patients with some forms of psychiatric illnesses have been found to have increased levels of cortisol (Krishnan (1992) *Prog. Neuro-Psychopharmacol. & Biol. Psychiat.* 16:913-920). For example, some depressed individuals can be responsive to treatments which block the effect of cortisol, as by administering GR antagonists (Van Look (1995) *Human Reproduction Update* 1:19-34). In one study, a patient with depression secondary to Cushing's Syndrome (hyperadrenocorticism) was responsive to a high dose, up to 1400 mg per day, of GR antagonist mifepristone (Nieman (1985) *J. Clin Endocrinol. Metab.* 61:536). Another study which used mifepristone to treat Cushing's syndrome found that it improved the patients' conditions, including their psychiatric status (Chrousos, pp 273-284, In: Baulieu, ed. *The Antiprogestin Steroid RU 486 and Human Fertility Control*. Plenum Press, New York (1989), Sartor (1996) *Clin. Obstetrics and Gynecol.* 39:506-510).

Psychosis has also been associated with Cushing's syndrome (Gerson (1985) *Can. J. Psychiatry* 30:223-224; Saad (1984) *Am. J. Med.* 76:759-766). Mifepristone has been used to treat acute psychiatric disturbances secondary to Cushing's syndrome. One study showed that a relatively high dose of mifepristone (400 to 800 mg per day) was useful in rapidly reversing acute psychosis in patients with severe Cushing Syndrome due to adrenal cancers and ectopic secretion of ACTH from lung cancer (Van der Lely (1991) *Ann. Intern. Med.* 114:143; Van der Lely (1993) *Pharmacy World & Science* 15:89-90; Sartor (1996) supra).

A treatment for psychosis or the psychotic component of illnesses, such as psychotic major depression, has recently been discovered (Schatzberg et al., U.S. Pat. No. 6,150,349). The treatment includes administration of an amount of a glucocorticoid receptor antagonist effective to ameliorate the psychosis. The psychosis may also be associated with psychotic major depression, Alzheimer's Disease and cocaine addiction.

Thus, there exists a great need for a more effective and safer treatment for illnesses and conditions associated with the glucocorticoid receptors, including psychotic major depression. The present invention fulfills these and other needs.

BRIEF SUMMARY OF THE INVENTION

In a first embodiment, the present invention provides a compound having the formula:

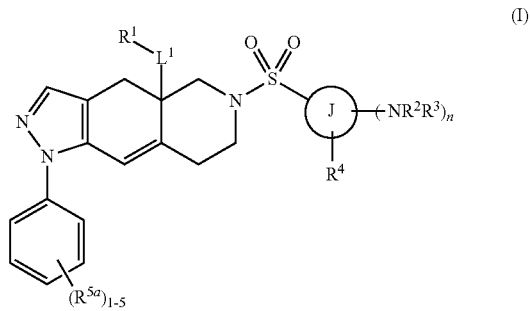

(I)

In Formula I, $L^1$ can be a bond, —C(O)O—$C_{0-6}$ alkylene, $C_{1-6}$ alkylene or $C_{1-6}$ heteroalkylene. $R^1$ of Formula I can be hydrogen, $C_{1-6}$ alkyl, $C_{1-6}$ haloalkyl, $C_{1-6}$ heteroalkyl, $C_{3-8}$ cycloalkyl, $C_{3-8}$ heterocycloalkyl, aryl, heteroaryl, —$OR^{1a}$, $NR^{1c}R^{1d}$, and —C(O)$NR^{1c}R^{1d}$, wherein the cycloalkyl, heterocycloalkyl, aryl or heteroaryl groups are optionally substituted with hydrogen, $C_{1-6}$ alkyl, hydroxy and $C_{1-6}$ alkoxy. Each $R^{1a}$ independently can be hydrogen, $C_{1-6}$ alkyl, $C_{1-6}$ haloalkyl, $C_{1-6}$ heteroalkyl, $C_{3-8}$ cycloalkyl, $C_{1-6}$alkyl$C_{3-8}$ cycloalkyl, $C_{3-8}$ heterocycloalkyl, $C_{1-6}$alkyl$C_{3-8}$ heterocycloalkyl, aryl, $C_{1-6}$ alkylaryl, heteroaryl or $C_{1-6}$ alkylheteroaryl. Each of $R^{1c}$ and $R^{1d}$ independently can be hydrogen, $C_{1-6}$ alkyl, $C_{1-6}$ heteroalkyl, $C_{3-8}$ cycloalkyl, $C_{3-8}$ heterocycloalkyl, aryl, or heteroaryl. Alternatively, $R^{1c}$ and $R^{1d}$ can be combined to form a $C_{3-8}$ heterocycloalkyl having from 1 to 3 heteroatoms each independently N, O or S, and optionally substituted with 1 to 3 groups each independently hydrogen, $C_{1-6}$ alkyl, hydroxy or $C_{1-6}$ alkoxy. Ring J is a heteroaryl ring having from 5 to 6 ring members and from 1 to 3 heteroatoms each independently N, O or S, wherein at least one heteroatom is N. Each of $R^2$ and $R^3$ are independently hydrogen, $C_{1-6}$ alkyl, $C_{2-6}$ alkenyl, $C_{2-6}$ alkynyl, $C_{1-6}$ haloalkyl, $C_{1-6}$ heteroalkyl, $C_{3-8}$ cycloalkyl, $C_{3-8}$ heterocycloalkyl, aryl or heteroaryl. In Formula I, $R^4$ can be hydrogen, halogen, $C_{1-6}$ alkyl, $C_{2-6}$ alkenyl, $C_{2-6}$ alkynyl, $C_{1-6}$ haloalkyl, $C_{1-6}$ alkoxy, $C_{1-6}$ haloalkoxy, $C_{1-6}$ heteroalkyl, $C_{3-8}$ cycloalkyl, $C_{3-8}$ heterocycloalkyl, aryl or heteroaryl. Alternatively $R^2$ can be combined with $R^3$ or $R^4$ to form a $C_{3-8}$ heterocycloalkyl having from 1 to 3 heteroatoms each independently N, O or S, and optionally substituted with 1 to 3 $R^{2a}$ groups, wherein each $R^{2a}$ independently can be hydrogen, $C_{1-6}$ alkyl, halogen, $C_{1-6}$ haloalkyl, hydroxy, $C_{1-6}$ alkoxy, $C_{1-6}$ haloalkoxy, nitro, cyano, $C_{3-8}$ cycloalkyl, $C_{3-8}$ heterocycloalkyl, aryl or heteroaryl. Subscript n of Formula I is 0 or 1. Each $R^{5a}$ independently can be hydrogen, halogen, —$OR^{5a1}$, —$NR^{5a2}R^{5a3}$, —$S(O_2)NR^{5a2}R^{5a3}$, —CN, $C_{1-6}$ alkyl, $C_{2-6}$ alkenyl, $C_{2-6}$ alkynyl, $C_{1-6}$ haloalkyl, $C_{1-6}$ heteroalkyl, $C_{3-8}$ cycloalkyl, $C_{3-8}$ heterocycloalkyl, aryl, or heteroaryl. Each of $R^{5a1}$, $R^{5a2}$ and $R^{5a3}$ independently can be hydrogen, $C_{1-6}$ alkyl, $C_{1-6}$ heteroalkyl, $C_{3-8}$ cycloalkyl, $C_{3-8}$ heterocycloalkyl, aryl, or heteroaryl. For the compound of Formula I, when $R^4$ is hydrogen, subscript n is 1. Also provided in the present invention are salts and isomers of compounds of Formula I.

In another embodiment, the present invention provides a pharmaceutical composition, including a compound of the present invention and a pharmaceutically acceptable excipient.

In another embodiment, the present invention provides a method of modulating a glucocorticoid receptor, the method including administering to a subject in need thereof, a therapeutically effective amount of a compound of the present invention.

In another embodiment, the present invention provides a method of treating a disorder or condition through modulating a glucocorticoid receptor, the method including administering to a subject in need thereof, a therapeutically effective amount of a compound of the present invention.

In another embodiment, the present invention provides a method of treating a disorder or condition through antagonizing a glucocorticoid receptor, the method including administering to a subject in need thereof, a therapeutically effective amount of a compound of the present invention.

DETAILED DESCRIPTION OF THE INVENTION

I. General

Figure 1:
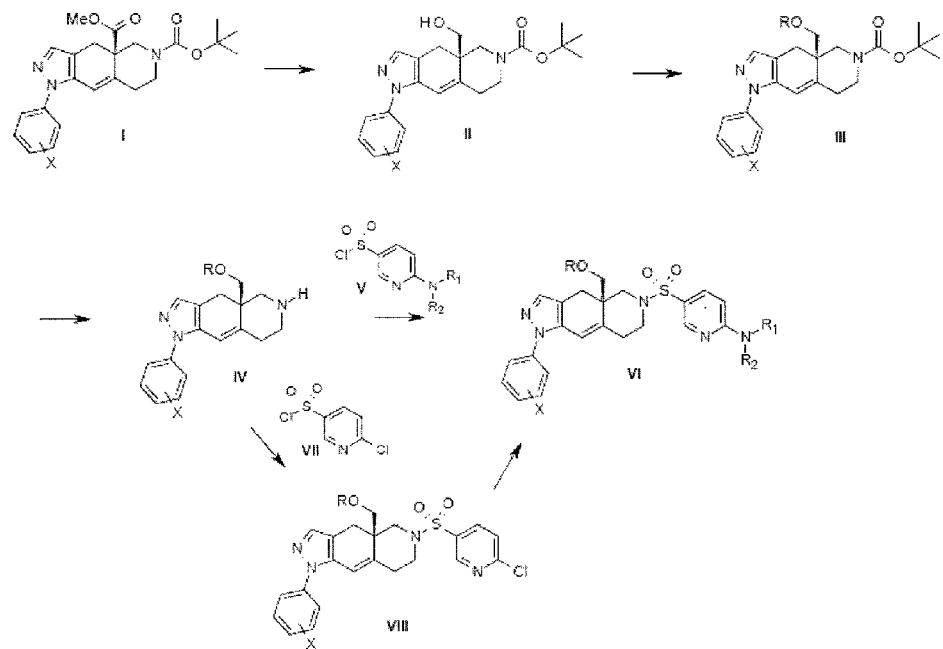
FIG. 1 shows methods of making compounds of the present invention.

The present invention provides pyridyl-amine fuzed azadecalin compounds and pharmaceutical compositions including pharmaceutically acceptable excipients. The compounds of the present invention are useful for modulating a glucocorticoid receptor and for treating a disorder or condition through modulating or antagonizing a glucocorticoid receptor.

II. Definitions

The abbreviations used herein have their conventional meaning within the chemical and biological arts.

Where substituent groups are specified by their conventional chemical formulae, written from left to right, they equally encompass the chemically identical substituents that would result from writing the structure from right to left, e.g., —$CH_2O$— is equivalent to —$OCH_2$—.

As used herein, the term "alkyl" refers to a straight or branched, saturated, aliphatic radical having the number of carbon atoms indicated. For example, $C_1$-$C_6$ alkyl includes, but is not limited to, methyl, ethyl, propyl, butyl, pentyl, hexyl, iso-propyl, iso-butyl, sec-butyl, tert-butyl, etc.

As used herein, the term "alkylene" refers to either straight chain or branched alkylene of 1 to 7 carbon atoms, i.e. a divalent hydrocarbon radical of 1 to 7 carbon atoms; for instance, straight chain alkylene being the bivalent radical of Formula —$(CH_2)_n$—, where n is 1, 2, 3, 4, 5, 6 or 7. Preferably alkylene represents straight chain alkylene of 1 to 4 carbon atoms, e.g. a methylene, ethylene, propylene or butylene chain, or the methylene, ethylene, propylene or butylene chain mono-substituted by $C_1$-$C_3$-alkyl (preferably methyl) or disubstituted on the same or different carbon atoms by $C_1$-$C_3$-alkyl (preferably methyl), the total number of carbon atoms being up to and including 7. One of skill in the art will appreciate that a single carbon of the alkylene can be divalent, such as in —$CH((CH_2)_nCH_3)$—, wherein n=0-5. The alkylene group can be linked to the same atom or different atoms.

As used herein, the term "heteroalkyl" refers to an alkyl group having from 1 to 3 heteroatoms such as N, O and S. Additional heteroatoms can also be useful, including, but not limited to, B, Al, Si and P. The heteroatoms can also be oxidized, such as, but not limited to, —S(O)— and —$S(O)_2$—. For example, heteroalkyl can include ethers, thioethers, alkyl-amines and alkyl-thiols.

As used herein, the term "heteroalkylene" refers to a heteroalkyl group, as defined above, linking at least two other groups. The two moieties linked to the heteroalkylene can be linked to the same atom or different atoms of the heteroalkylene.

As used herein, the term "alkenyl" refers to either a straight chain or branched hydrocarbon of 2 to 6 carbon atoms, having at least one double bond. Examples of alkenyl groups include, but are not limited to, vinyl, propenyl, isopropenyl, butenyl, isobutenyl, butadienyl, pentenyl or hexadienyl.

As used herein, the term "alkynyl" refers to either a straight chain or branched hydrocarbon of 2 to 6 carbon atoms, having at least one triple bond. Examples of alkynyl groups include, but are not limited to, acetylenyl, propynyl or butynyl.

As used herein, the term "cycloalkyl" refers to a saturated or partially unsaturated, monocyclic, fused bicyclic or bridged polycyclic ring assembly containing from 3 to 12 ring atoms, or the number of atoms indicated. For example, $C_{3-8}$ cycloalkyl includes cyclopropyl, cyclobutyl, cyclopentyl, cyclohexyl, cycloheptyl, and cyclooctyl. Cycloalkyl also includes norbornyl and adamantyl.

As used herein, the terms "heterocycloalkyl" and "heterocyclic" refer to a ring system having from 3 ring members to about 20 ring members and from 1 to about 5 heteroatoms such as N, O and S. For example, heterocycle includes, but is not limited to, tetrahydrofuranyl, tetrahydrothiophenyl, morpholino, pyrrolidinyl, pyrrolinyl, imidazolidinyl, imidazolinyl, pyrazolidinyl, pyrazolinyl, piperazinyl, piperidinyl, indolinyl, quinuclidinyl and 1,4-dioxa-8-aza-spiro[4.5]dec-8-yl.

As used herein, the term "alkoxy" refers to alkyl with the inclusion of an oxygen atom, for example, methoxy, ethoxy, etc.

As used herein, the terms "halo" or "halogen," by themselves or as part of another substituent, mean, unless otherwise stated, a fluorine, chlorine, bromine, or iodine atom.

As used herein, the term "haloalkyl" refers to alkyl as defined above where some or all of the hydrogen atoms are substituted with halogen atoms. Halogen (halo) preferably represents chloro or fluoro, but may also be bromo or iodo.

For example, haloalkyl includes trifluoromethyl, fluoromethyl, etc. The term "perfluoro" defines a compound or radical which has at least two available hydrogens substituted with fluorine. For example, perfluoromethane refers to 1,1,1-trifluoromethyl and perfluoromethoxy refers to 1,1,1-trifluoromethoxy.

As used herein, the term "aryl" refers to a monocyclic or fused bicyclic, tricyclic or greater, aromatic ring assembly containing 6 to 16 ring carbon atoms. For example, aryl may be phenyl, benzyl, naphthyl, or phenanthrenyl, preferably phenyl. "Arylene" means a divalent radical derived from an aryl group. Aryl groups can be mono-, di- or tri-substituted by one, two or three radicals selected from alkyl, alkoxy, aryl, hydroxy, halogen, cyano, amino, amino-alkyl, trifluoromethyl, alkylenedioxy and oxy-$C_2$-$C_3$-alkylene.

As used herein, the term "heteroaryl" refers to a monocyclic or fused bicyclic or tricyclic aromatic ring assembly containing 5 to 16 ring atoms, where from 1 to 4 of the ring atoms are a heteroatom each N, O or S. For example, heteroaryl includes pyridyl, indolyl, indazolyl, quinoxalinyl, quinolinyl, isoquinolinyl, benzothienyl, benzofuranyl, furanyl, pyrrolyl, thiazolyl, benzothiazolyl, oxazolyl, isoxazolyl, triazolyl, tetrazolyl, pyrazolyl, imidazolyl, thienyl, or any other radicals substituted, especially mono- or di-substituted, by e.g. alkyl, nitro or halogen. Pyridyl represents 2-, 3- or 4-pyridyl. Thienyl represents 2- or 3-thienyl. Quinolinyl represents preferably 2-, 3- or 4-quinolinyl. Isoquinolinyl represents preferably 1-, 3- or 4-isoquinolinyl. Benzopyranyl, benzothiopyranyl represents preferably 3-benzopyranyl or 3-benzothiopyranyl, respectively. Thiazolyl represents preferably 2- or 4-thiazolyl, and most preferred, 4-thiazolyl. Triazolyl is preferably 1-, 2- or 5-(1,2,4-triazolyl). Tetrazolyl is preferably 5-tetrazolyl.

Preferably, heteroaryl is pyridyl, indolyl, quinolinyl, pyrrolyl, thiazolyl, isoxazolyl, triazolyl, tetrazolyl, pyrazolyl, imidazolyl, thienyl, furanyl, benzothiazolyl, benzofuranyl, isoquinolinyl, benzothienyl, oxazolyl, indazolyl, or any of the radicals substituted, especially mono- or di-substituted.

Substituents for the aryl and heteroaryl groups are varied and are selected from: -halogen, —OR', —OC(O)R', —NR'R", —SR', —R', —CN, —NO$_2$, —CO$_2$R', —CONR'R", —C(O)R', —OC(O)NR'R", —NR"C(O)R', —NR"C(O)$_2$R', —NR'—C(O)NR"R'", —NH—C(NH$_2$)=NH, —NR'C(NH$_2$)=NH, —NH—C(NH$_2$)=NR', —S(O)R', —S(O)$_2$R', —S(O)$_2$NR'R", —N$_3$, —CH(Ph)$_2$, perfluoro($C_1$-$C_4$)alkoxy, and perfluoro($C_1$-$C_4$)alkyl, in a number ranging from zero to the total number of open valences on the aromatic ring system; and where R', R" and R'" are independently selected from hydrogen, $C_1$-$C_8$ alkyl and heteroalkyl, unsubstituted aryl and heteroaryl, (unsubstituted aryl)-($C_1$-$C_4$)alkyl, and (unsubstituted aryl)oxy-($C_1$-$C_4$)alkyl.

As used herein, the terms "arylalkyl" and "alkylaryl", refer to an aryl radical attached directly to an alkyl group. Likewise, the terms "arylalkenyl" and "aryloxyalkyl" refer to an aryl radical attached directly to alkenyl group, or an oxygen which is attached to an alkyl group, respectively. The term "aryloxy" refers to an aryl radical as described above which also bears an oxygen substituent which is capable of covalent attachment to another radical (such as, for example, phenoxy, naphthyloxy, and pyridyloxy).

As used herein, the term "alkylheteroaryl" refers to an heteroaryl radical attached directly to an alkyl group.

As used herein, the term "oxo" as used herein means an oxygen that is double bonded to a carbon atom.

Each of the above terms (e.g., "alkyl," "heteroalkyl," "aryl" and "heteroaryl") are meant to include both substituted and unsubstituted forms of the indicated radical.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to: —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NR(SO$_2$)R', —CN and —NO$_2$ in a number ranging from zero to (2 m'+1), where m' is the total number of carbon atoms in such radical. R', R", R'" and R"" are each independently selected from hydrogen, $C_1$-$C_8$ alkyl and heteroalkyl, unsubstituted aryl and heteroaryl, (unsubstituted aryl)-($C_1$-$C_4$)alkyl, and (unsubstituted aryl)oxy-($C_1$-$C_4$)alkyl. When a compound of the invention includes more than one R group, for example, each of the R groups is independently selected as are each R', R", R'" and R"" groups when more than one of these groups is present. When R' and R" are attached to the same nitrogen atom, they can be combined with the nitrogen atom to form a 4-, 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

As used herein, the term "salt" refers to acid or base salts of the compounds used in the methods of the present invention. Illustrative examples of pharmaceutically acceptable salts are mineral acid (hydrochloric acid, hydrobromic acid, phosphoric acid, and the like) salts, organic acid (acetic acid, propionic acid, glutamic acid, citric acid and the like) salts, quaternary ammonium (methyl iodide, ethyl iodide, and the like) salts. It is understood that the pharmaceutically acceptable salts are non-toxic. Additional information on suitable pharmaceutically acceptable salts can be found in Remington's Pharmaceutical Sciences, 17th ed., Mack Publishing Company, Easton, Pa., 1985, which is incorporated herein by reference.

As used herein, the term "hydrate" refers to a compound that is complexed to at least one water molecule. The compounds of the present invention can be complexed with from 1 to 10 water molecules.

Where two substituents are "optionally joined together to form a ring," the two substituents are covalently bonded together with the atom or atoms to which the two substituents are joined to form a substituted or unsubstituted aryl, a substituted or unsubstituted heteroaryl, a substituted or unsubstituted cycloalkyl, or a substituted or unsubstituted heterocycloalkyl ring.

As used herein, the term "cortisol" refers to a family of compositions also referred to as hydrocortisone, and any synthetic or natural analogues thereof.

As used herein, the term "glucocorticoid receptor" ("GR") refers to a family of intracellular receptors also referred to as the cortisol receptor, which specifically bind to cortisol and/or cortisol analogs (e.g. dexamethasone). The term includes isoforms of GR, recombinant GR and mutated GR.

As used herein, the term "glucocorticoid receptor antagonist" refers to any composition or compound which partially or completely inhibits (antagonizes) the binding of a glucocorticoid receptor (GR) agonist, such as cortisol, or cortisol analogs, synthetic or natural, to a GR. A "specific glucocorticoid receptor antagonist" refers to any composition or compound which inhibits any biological response associated with the binding of a GR to an agonist. By "specific," we intend the drug to preferentially bind to the GR rather than other nuclear receptors, such as mineralocorticoid receptor (MR) or progesterone receptor (PR).

As used herein, the terms "pharmaceutically acceptable excipient" and "pharmaceutically acceptable carrier" refer to a substance that aids the administration of an active agent to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors and colors, and the like. One of skill in the art will recognize that other pharmaceutical excipients are useful in the present invention.

As used herein, the term "modulating a glucocorticoid receptor" refers to methods for adjusting the response of a glucocorticoid receptor towards glucocorticoids, glucocorticoid antagonists, agonists, and partial agonists. The methods include contacting a glucocorticoid receptor with an effective amount of either an antagonist, an agonist, or a partial agonist and detecting a change in GR activity.

As used herein, the term "isomers" refers to compounds with the same chemical formula but which are structurally distinguishable.

As used herein, the term "tautomer," refers to one of two or more structural isomers which exist in equilibrium and which are readily converted from one form to another.

As used herein, the terms "patient" or "subject in need thereof" refers to a living organism suffering from or prone to a condition that can be treated by administration of a pharmaceutical composition as provided herein. Non-limiting examples include humans, other mammals and other non-mammalian animals.

As used herein, the terms "therapeutically effective amount" refers to an amount of a conjugated functional agent or of a pharmaceutical composition useful for treating or ameliorating an identified disease or condition, or for exhibiting a detectable therapeutic or inhibitory effect. The effect can be detected by any assay method known in the art.

The amount of GR modulator adequate to treat a disease through modulating the GR is defined as a "therapeutically effective dose." The dosage schedule and amounts effective for this use, i.e., the "dosing regimen," will depend upon a variety of factors, including the stage of the disease or condition, the severity of the disease or condition, the general state of the patient's health, the patient's physical status, age and the like. In calculating the dosage regimen for a patient, the mode of administration also is taken into consideration.

As used herein, the terms "treat", "treating" and "treatment" refers to any indicia of success in the treatment or amelioration of an injury, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation.

As used herein, the terms "disorder" or "condition" refer to a state of being or health status of a patient or subject capable of being treated with the glucocorticoid receptor modulators of the present invention.

As used herein, the term "co-administer" means to administer more than one active agent, such that the duration of physiological effect of one active agent overlaps with the physiological effect of a second active agent.

As used herein, the terms "a," "an," or "a(n)", when used in reference to a group of substituents or "substituent group" herein, mean at least one. For example, where a compound is substituted with "an" alkyl or aryl, the compound is optionally substituted with at least one alkyl and/or at least one aryl, wherein each alkyl and/or aryl is optionally different. In another example, where a compound is substituted with "a" substituent group, the compound is substituted with at least one substituent group, wherein each substituent group is optionally different.

Description of compounds of the present invention are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, or physiological conditions.

III. Compounds

In a first embodiment, the present invention provides compounds having the following formula:

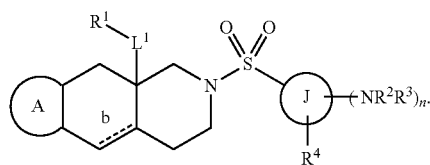

The dashed line b is optionally a bond. Ring A can be $C_{3-8}$ heterocycloalkyl or heteroaryl, each having from 5 to 6 ring members and each independently substituted with 1 to 4 $R^5$ groups which can be hydrogen, $C_{1-6}$ alkyl, $C_{1-6}$ heteroalkyl, $C_{3-8}$ cycloalkyl, $C_{3-8}$ heterocycloalkyl, heteroaryl, or aryl, each substituted with from 1 to 4 $R^{5a}$ groups. $R^{5a}$ and other groups are as defined for Formula I below.

In other embodiments, the present invention provides a compound of Formula I:

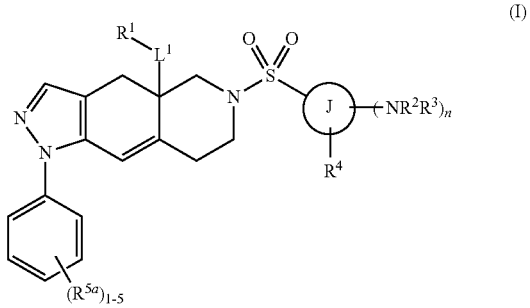

(I)

In Formula I, $L^1$ can be a bond, —C(O)O—$C_{0-6}$ alkylene, $C_{1-6}$ alkylene or $C_{1-6}$ heteroalkylene. $R^1$ of Formula I can be hydrogen, $C_{1-6}$ alkyl, $C_{1-6}$ haloalkyl, $C_{1-6}$ heteroalkyl, $C_{3-8}$ cycloalkyl, $C_{3-8}$ heterocycloalkyl, aryl, heteroaryl, —$O^{1a}$, $NR^{1c}R^{1d}$, and —$C(O)NR^{1c}R^{1d}$, wherein the cycloalkyl, heterocycloalkyl, aryl or heteroaryl groups are optionally substituted with hydrogen, $C_{1-6}$ alkyl, hydroxy and $C_{1-6}$ alkoxy. Each $R^{1a}$ independently can be hydrogen, $C_{1-6}$ alkyl, $C_{1-6}$ haloalkyl, $C_{1-6}$ heteroalkyl, $C_{3-8}$ cycloalkyl, $C_{1-6}$alkyl$C_{3-8}$ cycloalkyl, $C_{3-8}$ heterocycloalkyl, $C_{1-6}$alkyl$C_{3-8}$ heterocycloalkyl, aryl, $C_{1-6}$ alkylaryl, heteroaryl or $C_{1-6}$ alkylheteroaryl. Each of $R^{1c}$ and $R^{1d}$ independently can be hydrogen, $C_{1-6}$ alkyl, $C_{1-6}$ heteroalkyl, $C_{3-8}$ cycloalkyl, $C_{3-8}$ heterocycloalkyl, aryl, or heteroaryl. Alternatively, $R^{1c}$ and $R^{1d}$ can be combined to form a $C_{3-8}$ heterocycloalkyl having from 1 to 3 heteroatoms each independently N, O or S, and optionally substituted with 1 to 3 groups each independently hydrogen, $C_{1-6}$ alkyl, hydroxy or $C_{1-6}$ alkoxy. Ring J is a heteroaryl ring having from 5 to 6 ring members and from 1 to 3 heteroatoms each independently N, O or S, wherein at least one heteroatom is N. Each of $R^2$ and $R^3$ are independently hydrogen, $C_{1-6}$ alkyl, $C_{2-6}$ alkenyl, $C_{2-6}$ alkynyl, $C_{1-6}$ haloalkyl, $C_{1-6}$ heteroalkyl, $C_{3-8}$ cycloalkyl, $C_{3-8}$ heterocycloalkyl, aryl or heteroaryl. In Formula I, $R^4$ can be hydrogen, halogen, $C_{1-6}$ alkyl, $C_{2-6}$ alkenyl, $C_{2-6}$ alkynyl, $C_{1-6}$ haloalkyl, $C_{1-6}$ alkoxy, $C_{1-6}$ haloalkoxy, $C_{1-6}$ heteroalkyl, $C_{3-8}$ cycloalkyl, $C_{3-8}$ heterocycloalkyl, aryl or heteroaryl. Alternatively $R^2$ can be combined with $R^3$ or $R^4$ to form a $C_{3-8}$ heterocycloalkyl having from 1 to 3 heteroatoms each independently N, O or S, and optionally substituted with 1 to 3 $R^{2a}$ groups, wherein each $R^{2a}$ independently can be hydrogen, $C_{1-6}$ alkyl, halogen, $C_{1-6}$ haloalkyl, hydroxy, $C_{1-6}$ alkoxy, $C_{1-6}$ haloalkoxy, nitro, cyano, $C_{3-8}$ cycloalkyl, $C_{3-8}$ heterocycloalkyl, aryl or heteroaryl. Subscript n of Formula I is 0 or 1. Each $R^{5a}$ independently can be hydrogen, halogen, —$OR^{5a1}$, —$NR^{5a2}R^{5a3}$, —$S(O_2)NR^{5a2}R^{5a3}$, —CN, $C_{1-6}$ alkyl, $C_{2-6}$ alkenyl, $C_{2-6}$ alkynyl, $C_{1-6}$ haloalkyl, $C_{1-6}$ heteroalkyl, $C_{3-8}$ cycloalkyl, $C_{3-8}$ heterocycloalkyl, aryl, or heteroaryl. Each of $R^{5a1}$, $R^{5a2}$ and $R^{5a3}$ independently can be hydrogen, $C_{1-6}$ alkyl, $C_{1-6}$ heteroalkyl, $C_{3-8}$ cycloalkyl, $C_{3-8}$ heterocycloalkyl, aryl, or heteroaryl. For the compound of Formula I, when $R^4$ is hydrogen, subscript n is 1. Also provided in the present invention are salts and isomers of compounds of Formula I.

In some embodiments, the compound of Formula I has the formula:

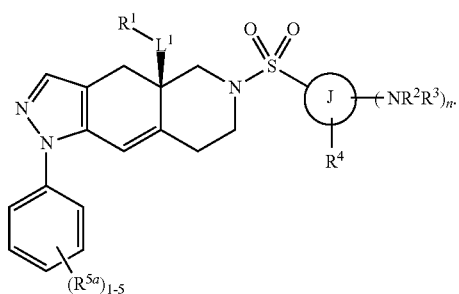

In some embodiments, the compound of Formula I has the formula:

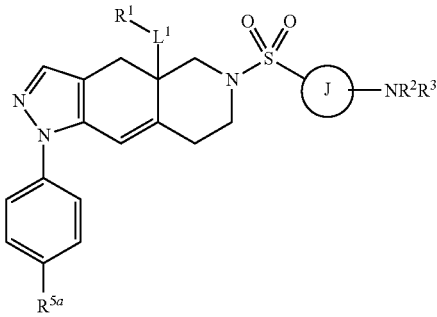

wherein each of $R^2$ and $R^3$ are independently H or $C_{1-6}$ alkyl. Alternatively, $R^2$ can be combined with $R^3$ to form a $C_{3-8}$ heterocycloalkyl having from 1 to 3 heteroatoms each independently N, O or S, and optionally substituted with 1 to 3 $R^{2a}$ groups, wherein each $R^{2a}$ independently can be hydrogen, $C_{1-6}$ alkyl, halogen, $C_{1-6}$ haloalkyl, hydroxy, $C_{1-6}$ alkoxy, $C_{1-6}$ haloalkoxy, nitro, cyano, $C_{3-8}$ cycloalkyl, $C_{3-8}$ heterocycloalkyl, aryl or heteroaryl. In addition, $R^{5a}$ can be halogen.

In some embodiments, $L^1$ can be —C(O)O—, —C(O)O—$C_{1-6}$ alkylene, or $C_{1-6}$ alkylene. $R^1$ of Formula I can be $C_{1-6}$ alkyl, $C_{3-8}$ cycloalkyl, $C_{3-8}$ heterocycloalkyl, heteroaryl, or —$OR^{1a}$, wherein the cycloalkyl, heterocycloalkyl and heteroaryl groups are optionally substituted with hydrogen, $C_{1-6}$ alkyl, hydroxy or $C_{1-6}$ alkoxy. And each $R^{1a}$ of Formula I independently can be hydrogen, $C_{1-6}$ alkyl, $C_{1-6}$ haloalkyl, $C_{1-6}$ heteroalkyl, $C_{3-8}$ cycloalkyl, $C_{1-6}$alkyl$C_{3-8}$ cycloalkyl, $C_{3-8}$ heterocycloalkyl, $C_{1-6}$alkyl$C_{3-8}$ heterocycloalkyl, aryl, $C_{1-6}$ alkylaryl, heteroaryl or $C_{1-6}$ alkylheteroaryl.

In some embodiments, $L^1$ and $R^1$ are joined to form the group $L^1$-$R^1$ which can be —$CH_2R^1$, —$CH_2OR^{1a}$, —C(O)OR$^1$ or —C(O)O—$CH_2$—$R^1$. In other embodiments, the group $L^1$-$R^1$ can be methoxymethyl, ethoxymethyl, isopropoxymethyl, (fluoromethoxy)methyl, (difluoromethoxy)methyl, (trifluoromethoxy)methyl, (cyclopropylmethoxy)methyl, (cyclobutylmethoxy)methyl, (2-methoxyethoxy)methyl, (2-hydroxyethoxy)methyl, (oxazol-2-ylmethoxy)methyl, (isoxazol-3-ylmethoxy)methyl, ((5-methylisoxazol-3-yl)methoxy)methyl, ((3-methyloxetan-3-yl)methoxy)methyl, (oxetan-3-ylmethoxy)methyl, N,N-dimethylaminomethyl, N-(2-hydroxyethyl)-N-methylaminomethyl, azetidin-1-ylmethyl, pyrrolidin-1-ylmethyl, (3-hydroxy-pyrrolidin-1-yl)methyl, methyl carboxylate, ethyl carboxylate, isopropyl carboxylate, cyclopropyl carboxylate, cyclobutyl carboxylate, cyclopropylmethyl carboxylate, cyclobutylmethyl carboxylate, (3-hydroxycyclobutyl)methyl carboxylate, (3-methyloxetan-3-yl)methyl carboxylate, 2-hydroxyethyl carboxylate, 2-(dimethylamino) ethyl carboxylate, or (5-methylisoxazol-3-yl)methyl carboxylate. In some other embodiments, the group $L^1$-$R^1$ can be methoxymethyl, ethoxymethyl, (difluoromethoxy)methyl, (cyclopropylmethoxy)methyl, (2-methoxyethoxy)methyl, (2-hydroxyethoxy)methyl, (oxazol-2-ylmethoxy)methyl, ((5-methylisoxazol-3-yl)methoxy)methyl, N-(2-hydroxyethyl)-N-methyl-aminomethyl, (3-hydroxy-pyrrolidin-1-yl) methyl, methyl carboxylate, ethyl carboxylate, isopropyl carboxylate, cyclobutyl carboxylate, cyclopropylmethyl carboxylate, cyclobutylmethyl carboxylate, (3-hydroxycyclobutyl)methyl carboxylate, (3-methyloxetan-3-yl)methyl carboxylate, 2-hydroxyethyl carboxylate, 2-(dimethylamino) ethyl carboxylate, or (5-methylisoxazol-3-yl)methyl carboxylate.

Ring J can be any suitable heteroaryl ring having from 5 to 6 ring members and from 1 to 3 heteroatoms each independently N, O or S, wherein at least one heteroatom is N. In some embodiments, ring J can be pyrrole, imidazole, pyrazole, thiazole, isothiazole, oxazole, isoxazole, pyridine, pyrazine, pyrimidine or pyridazine. In other embodiments, ring J can be pyrrole, imidazole, pyrazole, pyridine, pyrazine, pyrimidine or pyridazine. In some other embodiments, ring J can be pyridine, pyrazine, pyrimidine and pyridazine. In yet other embodiments, ring J can be pyrid-2-yl, pyrid-3-yl or pyrid-4-yl.

In some embodiments, the compound of Formula I has the formula:

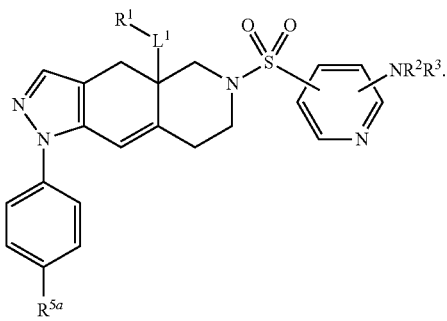

In some embodiments, $R^2$ can be combined with $R^3$ to form a $C_{3-8}$ heterocycloalkyl having from 1 to 2 heteroatoms each independently N or O, and optionally substituted with 1 to 3 $R^{2a}$ groups, wherein each $R^{2a}$ can be $C_{1-6}$ alkyl, halogen, $C_{1-6}$ haloalkyl, hydroxy, $C_{1-6}$ alkoxy or $C_{1-6}$ haloalkoxy.

The groups $R^2$ and $R^3$ can be any suitable groups, such as hydrogen, $C_{1-6}$ alkyl, $C_{2-6}$ alkenyl, $C_{2-6}$ alkynyl, $C_{1-6}$ haloalkyl, $C_{1-6}$ heteroalkyl, $C_{3-8}$ cycloalkyl, $C_{3-8}$ heterocycloalkyl, aryl or heteroaryl. Alternatively $R^2$ can be combined with $R^3$ to form a $C_{3-8}$ heterocycloalkyl having from 1 to 3 heteroatoms each independently N, O or S, and optionally substituted with 1 to 3 $R^{2a}$ groups, wherein each $R^{2a}$ independently can be hydrogen, $C_{1-6}$ alkyl, halogen, $C_{1-6}$ haloalkyl, hydroxy, $C_{1-6}$ alkoxy, $C_{1-6}$ haloalkoxy, nitro, cyano, $C_{3-8}$ cycloalkyl, $C_{3-8}$ heterocycloalkyl, aryl or heteroaryl. In some embodiments, $R^2$ and $R^3$ are not combined. In other embodiments, $R^2$ can be combined with $R^3$ to form a $C_{3-8}$ heterocycloalkyl such as azetidine, pyrrolidine, imidazolidine, pyrazolidine, oxazolidine, isoxazolidine, piperidine, piperazine, morpholine, azepane, homopiperazine, azacyclooctane, quinuclidine, 1,4-diazabicyclo[2.2.2]octane or 2-oxa-5-azabicyclo[2.2.1]heptane, each optionally substituted with 1 $R^{2a}$ group such as halogen or hydroxy. In other embodiments, $R^2$ can be combined with $R^3$ to form a $C_{3-8}$ heterocycloalkyl such as azetidin-1-yl, pyrrolidin-1-yl, piperidin-1-yl, morpholin-1-yl or 2-oxa-5-azabicyclo[2.2.1]heptan-5-yl, wherein the azetidin-1-yl, pyrrolidin-1-yl, and piperidin-1-yl are each optionally substituted with 1 $R^{2a}$ group such as F and hydroxy. In some other embodiments, $R^2$ can be combined with $R^3$ to form a $C_{3-8}$ heterocycloalkyl such as azetidin-1-yl, 3-fluoro-azetidin-1-yl, 3-hydroxy-azetidin-1-yl, pyrrolidin-1-yl, 3-hydroxy-pyrrolidin-1-yl, morpholin-1-yl or 2-oxa-5-azabicyclo[2.2.1]heptan-5-yl.

In Formula I, $R^4$ can be any suitable group, such as hydrogen, halogen, $C_{1-6}$ alkyl, $C_{2-6}$ alkenyl, $C_{2-6}$ alkynyl, $C_{1-6}$ haloalkyl, $C_{1-6}$ alkoxy, $C_{1-6}$ haloalkoxy, $C_{1-6}$ heteroalkyl, $C_{3-8}$ cycloalkyl, $C_{3-8}$ heterocycloalkyl, aryl or heteroaryl. In some embodiments, $R^4$ can be hydrogen, halogen, $C_{1-6}$ alkyl, $C_{1-6}$ haloalkyl, $C_{1-6}$ alkoxy or $C_{1-6}$ haloalkoxy. In other embodiments, $R^4$ can be hydrogen, $C_{1-6}$ haloalkyl or $C_{1-6}$ alkoxy. In some other embodiments, $R^4$ can be hydrogen, $CF_3$ or $OCH_3$.

The group $R^{5a}$ in Formula I can be any suitable group, such as, hydrogen, halogen, $-OR^{5a1}$, $-NR^{5a2}R^{5a3}$, $-S(O_2)NR^{5a2}R^{5a3}$, $-CN$, $C_{1-6}$ alkyl, $C_{2-6}$ alkenyl, $C_{2-6}$ alkynyl, $C_{1-6}$ haloalkyl, $C_{1-6}$ heteroalkyl, $C_{3-8}$ cycloalkyl, $C_{3-8}$ heterocycloalkyl, aryl, or heteroaryl. Each of $R^{5a1}$, $R^{5a2}$ and $R^{5a3}$ independently can be hydrogen, $C_{1-6}$ alkyl, $C_{1-6}$ heteroalkyl, $C_{3-8}$ cycloalkyl, $C_{3-8}$ heterocycloalkyl, aryl, or heteroaryl. In some embodiments, $R^{5a}$ can be halogen, such as F, Cl, Br or I. In other embodiments, $R^{5a}$ can be F.

In some embodiments, the compound of Formula I can have any of the following formulas:

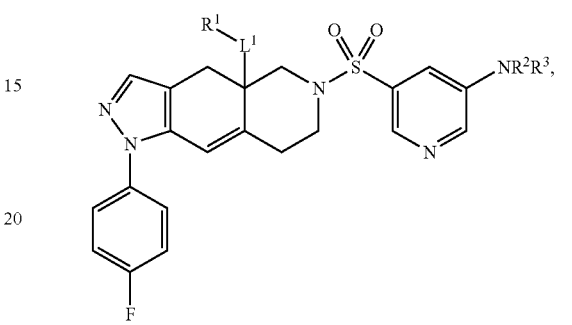

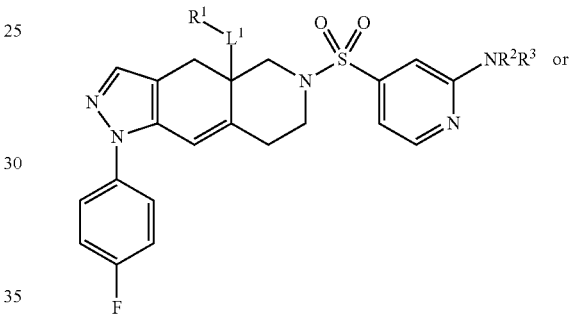

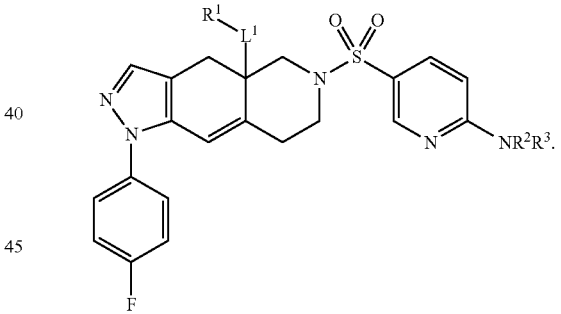

In some embodiments, the compound of Formula I has the formula:

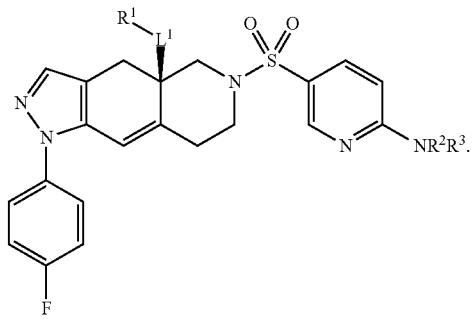

In some embodiments, the compound of Formula I can have any of the following formulas:

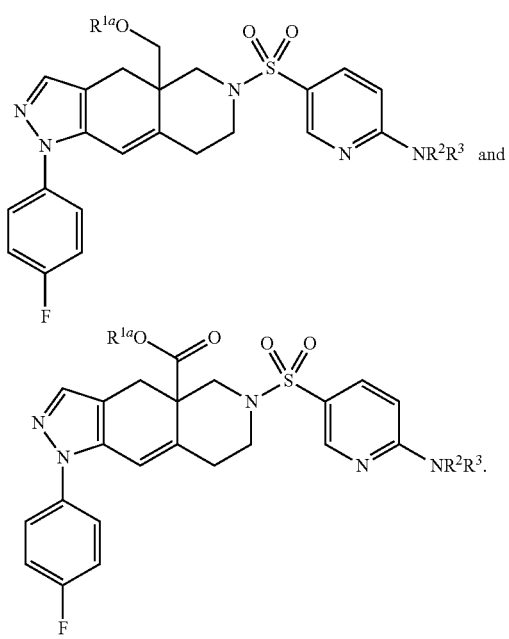

In some embodiments, the compound of Formula I can have the following formula:

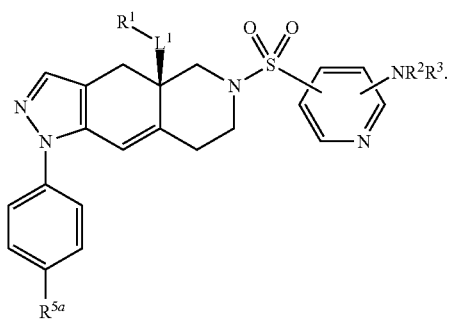

In some embodiments, $L^1$ can be a bond, $C_{1-6}$ alkylene or $C_{1-6}$ heteroalkylene. $R^1$ of Formula I can be hydrogen, $C_{1-6}$ alkyl, $C_{1-6}$ haloalkyl, $C_{1-6}$ heteroalkyl, $C_{3-8}$ cycloalkyl, $C_{3-8}$ heterocycloalkyl, aryl, heteroaryl, —$OR^{1a}$, $NR^{1c}R^{1d}$, —$C(O)NR^{1c}R^{1d}$, or —$C(O)OR^{1a}$. $R^{1a}$ of Formula I can be hydrogen, $C_{1-6}$ alkyl, $C_{1-6}$ haloalkyl, $C_{1-6}$ heteroalkyl, $C_{3-8}$ cycloalkyl, $C_{1-6}$alkyl$C_{3-8}$cycloalkyl, $C_{3-8}$ heterocycloalkyl, $C_{1-6}$alkyl$C_{3-8}$heterocycloalkyl, aryl, $C_{1-6}$ alkylaryl, heteroaryl or $C_{1-6}$ alkylheteroaryl. Each of $R^{1c}$ and $R^{1d}$ of Formula I are independently hydrogen, $C_{1-6}$ alkyl, $C_{1-6}$ heteroalkyl, $C_{3-8}$ cycloalkyl, $C_{3-8}$ heterocycloalkyl, aryl, or heteroaryl. Ring J is a heteroaryl ring having from 5 to 6 ring members and from 1 to 3 heteroatoms each independently N, O or S, wherein at least one heteroatom is N. Each of $R^2$ and $R^3$ of Formula I are independently H, $C_{1-6}$ alkyl, $C_{2-6}$ alkenyl, $C_{2-6}$ alkynyl, $C_{1-6}$ haloalkyl, $C_{1-6}$ heteroalkyl, $C_{3-8}$ cycloalkyl, $C_{3-8}$ heterocycloalkyl, aryl or heteroaryl. $R^4$ of Formula I can be H, halogen, $C_{1-6}$ alkyl, $C_{2-6}$ alkenyl, $C_{2-6}$ alkynyl, $C_{1-6}$ haloalkyl, $C_{1-6}$ alkoxy, $C_{1-6}$ heteroalkyl, $C_{3-8}$ cycloalkyl, $C_{3-8}$ heterocycloalkyl, aryl or heteroaryl.

Alternatively, $R^2$ of Formula I is combined with $R^3$ or $R^4$ to form a $C_{3-8}$ heterocycloalkyl having from 1 to 3 heteroatoms each independently N, O or S, and optionally substituted with 1 to 3 groups each independently hydrogen or $C_{1-6}$ alkyl. The subscript n is 0 or 1 in Formula I. Each $R^{5a}$ of Formula I is independently hydrogen, halogen, —$OR^{5a1}$, —$NR^{5a2}R^{5a3}$, —$S(O_2)NR^{5a2}R^{5a3}$, —CN, $C_{1-6}$ alkyl, $C_{2-6}$ alkenyl, $C_{2-6}$ alkynyl, $C_{1-6}$ haloalkyl, $C_{1-6}$ heteroalkyl, $C_{3-8}$ cycloalkyl, $C_{3-8}$ heterocycloalkyl, aryl, or heteroaryl. Each of $R^{5a1}$, $R^{5a2}$ and $R^{5a3}$ of Formula I are independently hydrogen, $C_{1-6}$ alkyl, $C_{1-6}$ heteroalkyl, $C_{3-8}$ cycloalkyl, $C_{3-8}$ heterocycloalkyl, aryl, or heteroaryl. The compounds of formula I also include salts and isomers thereof.

In some other embodiments, $R^1$ is —$OR^{1a}$ or —$C(O)OR^{1a}$.

In some other embodiments, the heteroatoms of ring J are N. Nitrogen containing rings useful as ring J include, but are not limited to, pyrrolyl, 1-pyrrolyl, 2-pyrrolyl, 3-pyrrolyl, pyrazolyl, 3-pyrazolyl, imidazolyl, 2-imidazolyl, 4-imidazolyl, 1,2,3-triazolyl, 1,2,4-triazolyl, tetrazolyl, pyridyl, 2-pyridyl, 3-pyridyl, 4-pyridyl, pyrimidyl, 2-pyrimidyl, 4-pyrimidyl, pyridazyl also known as 1,2-diazyl, pyrimidyl also known as 1,3-diazyl, 1,4-diazabenzyl, 1,2,3-triazyl, 1,2,4-triazyl, and 1,3,5-triazyl.

In some other embodiments, the compound of Formula I has the formula:

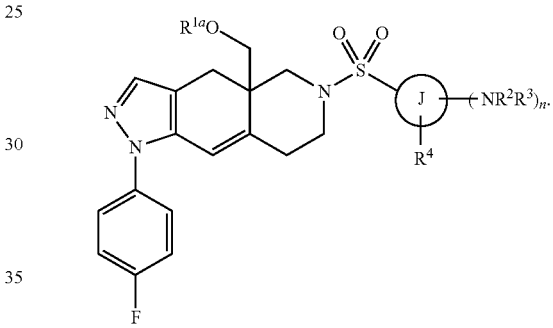

In other embodiments, the compound of Formula I has the formula:

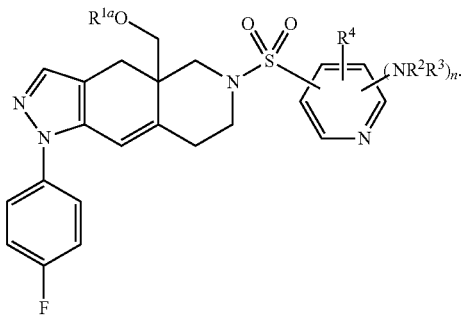

The pyridyl ring can be bonded to the sulfonyl group through either the 2, 3, or 4 position. In other embodiments, $R^{1a}$ can be $C_{1-6}$ alkyl, $C_{1-6}$ haloalkyl or $C_{1-6}$ alkylheteroaryl. In some embodiments, $R^{1a}$ can be methyl, ethyl, —$CHF_2$ or

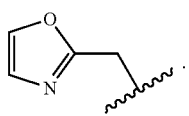 [SMILES: *Cc1ncco1]

In some other embodiments, the compound of Formula I has any of the following formula:

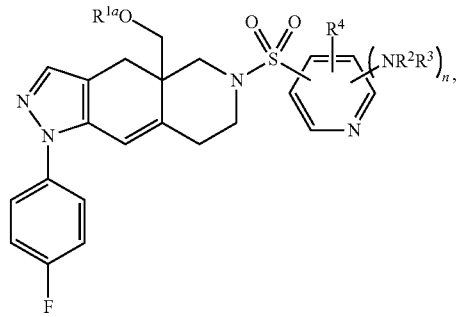

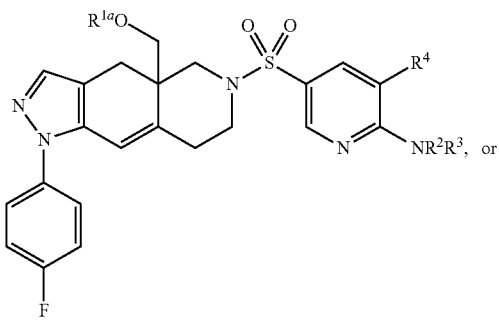

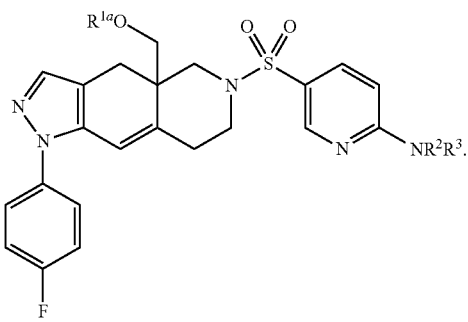

In some embodiments, the compound of Formula I has the following formula:

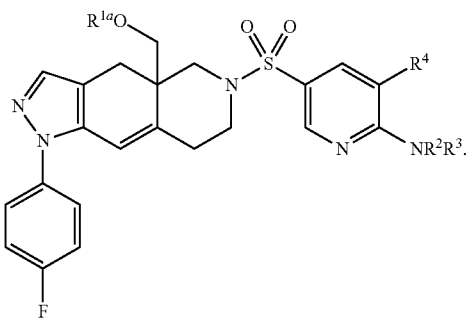

In other embodiments, $R^2$ and $R^4$ are combined to form a heterocyclic ring having from 5 to 6 ring members.

In some embodiments, the compound of Formula I has the following formula:

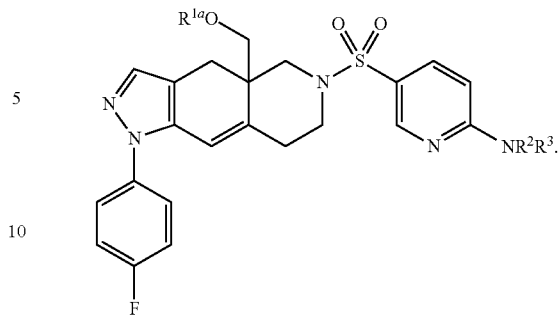

In some embodiments, $R^2$ and $R^3$ are independently H or $C_{1-6}$ alkyl. In other embodiments, $R^2$ and $R^3$ are combined to form a heterocyclic ring having from 4 to 6 ring members. Exemplary rings include, but are not limited to, azetidine, morpholino, pyrrolidinyl, pyrrolinyl, imidazolidinyl, imidazolinyl, pyrazolidinyl, pyrazolinyl, piperazinyl, piperidinyl, indolinyl. In some other embodiments, $R^2$ and $R^3$ are combined to form azetidine, pyrrolidine or morpholine.

In some other embodiments, the compound of Formula I has the following formula:

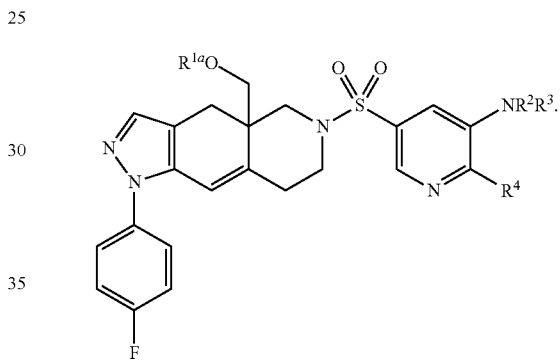

In some other embodiments, subscript n is 0.

In some embodiments, the compound of Formula I can be any one of the compounds in Table 1. In other embodiments, the compound of Formula I can be (R)-4a-Ethoxymethyl-1-(4-fluorophenyl)-6-[[6-(4-morpholinyl)-3-pyridinyl]sulfonyl]-1,4,7,8-tetrahydro-1,2,6-triazacyclopenta[b]naphthalene, (R)-1-(4-Fluorophenyl)-6-(6-morpholin-4-ylpyridine-3-sulfonyl)-1,4,5,6,7,8-hexahydro-1,2,6-triazacyclopenta[b]naphthalene-4a-carboxylic acid methyl ester,

[(R)-1-(4-Fluorophenyl)-6-[[6-(4-morpholinyl)-3-pyridinyl]sulfonyl]-1,4,7,8-tetrahydro-1,2,6-triazacyclopenta[b]naphthalen-4a-yl]methanol, (R)-4a-Ethoxymethyl-1-(4-fluorophenyl)-6-[[3-pyridinyl]sulfonyl]-1,4,7,8-tetrahydro-1,2,6-triazacyclopenta[b]naphthalene, (R)-4a-Ethoxymethyl-1-(4-fluorophenyl)-6-[[2H-pyrido[3.2-b]-1,4-oxazin-7-yl]sulfonyl]-1,4,7,8-tetrahydro-1,2,6-triazacyclopenta[b]naphthalene, (R)-4a-Ethoxymethyl-1-(4-fluorophenyl)-6-[[6-(1-pyrrolidinyl)-3-pyridinyl]sulfonyl]-1,4,7,8-tetrahydro-1,2,6-triazacyclopenta[b]naphthalene, (R)-1-(4-Fluorophenyl)-4a-methoxymethyl-6-[[6-(1-pyrrolidinyl)-3-pyridinyl]sulfonyl]-1,4,7,8-tetrahydro-1,2,6-triazacyclopenta[b]naphthalene, (R)-6-[[6-(1-Azetidinyl)-3-pyridinyl]sulfonyl]-4a-ethoxymethyl-1-(4-fluorophenyl)-1,4,7,8-tetrahydro-1,2,6-triazacyclopenta[b]naphthalene, (R)-4a-Ethoxymethyl-1-(4-fluorophenyl)-6-[[6-methylamino-3-pyridinyl]sulfonyl]-1,4,7,8-tetrahydro-1,2,6-triazacyclopenta[b]naphthalene, (R)-6-[[6-Dimethylamino-3-pyridinyl]sulfonyl]-4a-ethoxymethyl-1-(4-fluorophenyl)-1,4,7,8-tetrahydro-1,2,6-triazacyclopenta[b]naphthalene, (R)-1-(4-Fluorophenyl)-4a-methoxymethyl-6-[[6-methylamino-3-pyridinyl]sulfonyl]-1,4,7,8-tetrahydro-1,2,6-triazacyclopenta[b]naphthalene, (R)-6-[[6-Dimethylamino-3-pyridinyl]sulfonyl]-1-(4-fluorophenyl)-4a-methoxymethyl-1,4,7,8-tetrahydro-1,2,6-triazacyclopenta[b]naphthalene, (R)-6-[[6-(1-Azetidinyl)-3-pyridinyl]sulfonyl]-1-(4-fluorophenyl)-4a-methoxymethyl-1,4,7,8-tetrahydro-1,2,6-triazacyclopenta[b]naphthalene, (R)-1-(4-Fluorophenyl)-4a-methoxymethyl-6-(5-morpholin-4-ylpyridine-3-sulfonyl)-4,4a,5,6,7,8-hexahydro-1H-1,2,6-triazacyclopenta[b]naphthalene, (R)-6-(5-Azetidin-1-ylpyridine-3-sulfonyl)-1-(4-fluorophenyl)-4a-methoxymethyl-4,4a,5,6,7,8-hexahydro-1H-1,2,6-triazacyclopenta[b]naphthalene, (R)-1-(4-Fluorophenyl)-4a-methoxymethyl-6-(6-morpholin-4-yl-pyridine-3-sulfonyl)-4,4a,5,6,7,8-hexahydro-1H-1,2,6-triazacyclopenta[b]naphthalene, (R)-4a-Difluoromethoxymethyl-1-(4-fluorophenyl)-6-(6-morpholin-4-yl-pyridine-3-sulfonyl)-4,4a,5,6,7,8-hexahydro-1H-1,2,6-triazacyclopenta[b]naphthalene, (R)-6-(6-Azetidin-1-yl-pyridine-3-sulfonyl)-1-(4-fluorophenyl)-4a-(oxazol-2-ylmethoxymethyl)-4,4a,5,6,7,8-hexahydro-1H-1,2,6-triazacyclopenta[b]naphthalene, (R)-6-(6-Azetidin-1-ylpyridine-3-sulfonyl)-4a-difluoromethoxymethyl-1-(4-fluorophenyl)-4,4a,5,6,7,8-hexahydro-1H-1,2,6-triazacyclopenta[b]naphthalene, (R)-1-(4-Fluorophenyl)-4a-methoxymethyl-6-[[6-(1-piperazinyl)-3-pyridinyl]sulfonyl]-1,4,7,8-tetrahydro-1,2,6-triazacyclopenta[b]naphthalene, (R)-1-(4-Fluorophenyl)-4a-methoxymethyl-6-[[6-(1-(4-methylpiperazinyl))-3-pyridinyl]sulfonyl]-1,4,7,8-tetrahydro-1,2,6-triazacyclopenta[b]naphthalene, (R)-1-(4-Fluorophenyl)-6-[6-((R)-3-fluoropyrrolidin-1-yl)-pyridine-3-sulfonyl]-4a-methoxymethyl-4,4a,5,6,7,8-hexahydro-1H-1,2,6-triaza-cyclopenta[b]naphthalene, (R)-1-{5-[(R)-1-(4-Fluorophenyl)-4a-methoxymethyl-1,4,4a,5,6,7,8-hexahydro-1,2,6-triaza-cyclopenta[b]naphthalene-6-sulfonyl]-pyridin-2-yl}-pyrrolidin-3-ol, (S)-1-{5-[(R)-1-(4-Fluorophenyl)-4a-methoxymethyl-1,4,4a,5,6,7,8-hexahydro-1,2,6-triaza-cyclopenta[b]naphthalene-6-sulfonyl]-pyridin-2-yl}-pyrrolidin-3-ol, (R)-1-(4-Fluorophenyl)-4a-methoxymethyl-6-[(1S,4S)-6-(2-oxa-5-aza-bicyclo[2.2.1]hept-5-yl)pyridine-3-sulfonyl]-4,4a,5,6,7,8-hexahydro-1H-1,2,6-triaza-cyclopenta[b]naphthalene, (R)-1-(4-Fluorophenyl)-4a-methoxymethyl-6-(6-trifluoromethylpyridine-3-sulfonyl)-4,4a,5,6,7,8-hexahydro-1H-1,2,6-triaza-cyclopenta[b]naphthalene, (R)-4a-Cyclopropylmethoxymethyl-1-(4-fluorophenyl)-6-(6-pyrrolidin-1-yl-pyridine-3-sulfonyl)-4,4a,5,6,7,8-hexahydro-1H-1,2,6-triaza-cyclopenta[b]naphthalene, (R)-4a-Cyclopropylmethoxymethyl-1-(4-fluorophenyl)-6-(6-((R)-3-fluoro-pyrrolidin-1-yl)-pyridine-3-sulfonyl)-4,4a,5,6,7,8-hexahydro-1H-1,2,6-triaza-cyclopenta[b]naphthalene, (R)-4a-Cyclopropylmethoxymethyl-1-(4-fluorophenyl)-6-(6-((S)-3-fluoropyrrolidin-1-yl)-pyridine-3-sulfonyl)-4,4a,5,6,7,8-hexahydro-1H-1,2,6-triaza-cyclopenta[b]naphthalene, (R)-1-{5-[(R)-4a-Cyclopropylmethoxymethyl-1-(4-fluorophenyl)-1,4,4a,5,6,7,8-hexahydro-1,2,6-triaza-cyclopenta[b]naphthalene-6-sulfonyl]pyridine-2-yl}-pyrrolidine-3-ol, (S)-1-{5-[(R)-4a-Cyclopropylmethoxymethyl-1-(4-fluorophenyl)-1,4,4a,5,6,7,8-hexahydro-1,2,6-triaza-cyclopenta[b]naphthalene-6-sulfonyl]pyridine-2-yl}-pyrrolidine-3-ol, (R)-4a-Cyclopropylmethoxymethyl-6-[6-(3-fluoroazetin-1-yl)-pyridine-3-sulfonyl]-1-(4-fluorophenyl)-1,4,4a,5,6,7,8-hexahydro-1H-1,2,6-triaza-cyclopenta[b]naphthalene, 1-{5-[(R)-4a-Cyclopropylmethoxymethyl-1-(4-fluorophenyl)-1,4,4a,5,6,7,8-hexahydro-1,2,6-triaza-cyclopenta[b]naphthalene-6-sulfonyl]-pyridin-2-yl}-azetidin-3-ol, (R)-4a-Cyclopropylmethoxymethyl-1-(4-fluorophenyl)-6-(6-morpholin-4-yl-pyridine-3-sulfonyl)-4,4a,5,6,7,8-hexahydro-1H-1,2,6-triaza-cyclopenta[b]naphthalene, (R)-1-(4-Fluorophenyl)-6-[6-((R)-3-fluoropyrrolidin-1-yl)-pyridine-3-sulfonyl]-4a-(2-methoxyethoxymethyl)-4,4a,5,6,7,8-hexahydro-1H-1,2,6-triaza-cyclopenta[b]naphthalene, 2-{(R)-1-(4-Fluorophenyl)-6-[6-((R)-3-fluoropyrrolidin-1-yl)-1,4,5,6,7,8-hexahydro-1,2,6-triaza-cyclopenta[b]naphthalene-4a-ylmethoxy}ethanol, (R)-1-(4-Fluorophenyl)-6-[6-((R)-3-fluoropyrrolidin-1-yl)-pyridine-3-sulfonyl]-4a-(5-methyl-isoxazol-3-yl-methoxymethyl)-4,4a,5,6,7,8-hexahydro-1H-1,2,6-triaza-cyclopenta[b]naphthalene, 1-{5-[(R)-1-(4-Fluorophenyl)-4a-methoxymethyl-1,4,4a,5,6,7,8-hexahydro-1,2,6-triaza-cyclopenta[b]naphthalene-6-sulfonyl]-pyridin-3-yl}-azetidin-3-ol, (R)-6-[5-(3-Fluoroazetidin-1-yl)-pyridine-3-sulfonyl]-1-(4-fluorophenyl)-4a-methoxymethyl-4,4a,5,6,7,8-hexahydro-1H-1,2,6-triaza-cyclopenta[b]naphthalene, (R)-1-{5-[(R)-1-(4-Fluorophenyl)-4a-methoxymethyl-1,4,4a,5,6,7,8-hexahydro-1,2,6-triaza-cyclopenta[b]naphthalene-6-sulfonyl]pyridine-3-yl}-pyrrolidine-3-ol, (S)-1-{5-[(R)-1-(4-Fluorophenyl)-4a-methoxymethyl-1,4,4a,5,6,7,8-hexahydro-1,2,6-triaza-cyclopenta[b]naphthalene-6-sulfonyl]pyridine-3-yl}-pyrrolidine-3-ol, (R)-1-(4-Fluorophenyl)-6-[5-((R)-3-fluoropyrrolidin-1-yl)-pyridine-3-sulfonyl]-4a-methoxymethyl-4,4a,5,6,7,8-hexahydro-1H-1,2,6-triaza-cyclopenta[b]naphthalene, (R)-1-(4-Fluorophenyl)-6-[5-((S)-3-fluoropyrrolidin-1-yl)-pyridine-3-sulfonyl]-4a-methoxymethyl-4,4a,5,6,7,8-hexahydro-1H-1,2,6-triaza-cyclopenta[b]naphthalene, (R)-1-(4-Fluorophenyl)-4a-methoxymethyl-6-(2-pyrrolidin-1-yl-pyridine-4-sulfonyl)-4,4a,5,6,7,8-hexahydro-1H-1,2,6-triaza-cyclopenta[b]naphthalene, (R)-1-{4-[(R)-1-(4-Fluorophenyl)-4a-methoxymethyl-1,4,4a,5,6,7,8-hexahydro-1,2,6-triaza-cyclopenta[b]naphthalene-6-sulfonyl]-pyridin-2-yl}-pyrrolidin-3-ol, (S)-1-{4-[(R)-1-(4-Fluorophenyl)-4a-methoxymethyl-1,4,4a,5,6,7,8-hexahydro-1,2,6-triaza-cyclopenta[b]naphthalene-6-sulfonyl]-pyridin-2-yl}-pyrrolidin-3-ol, 2-{[(S)-1-(4-Fluorophenyl)-6-[6-morpholin-4-yl-pyridine-3-sulfonyl]-1,4,5,6,7,8-hexahydro-1,2,6-triaza-cyclopenta[b]naphthalene-4a-ylmethyl]-methyl-amino}-ethanol, (S)-1-{(S)-1-(4-Fluorophenyl)-6-[6-((R)-3-hydroxy-pyrrolidin-3-ol)-pyridine-3-sulfonyl]-1,4,5,6,7,8-triaza-cyclopenta[b]naphthalene-4a-ylmethyl}-pyrrolidin-3-ol, (S)-1-{(S)-1-(4-Fluorophenyl)-6-[6-((R)-3-fluoro-pyrrolidin-1-yl)-pyridine-3-sulfonyl]-1,4,5,6,7,8-hexahydro-1,2,6-triaza-cyclopenta[b]naphthalene-4a-ylmethyl}-pyrrolidin-3-ol, (R)-1-(4-Fluorophenyl)-6-(6-morpholin-4-yl-pyridine-3-sulfonyl]-1,4,5,6,7,8-hexahydro-1,2,6-triaza-cyclopenta[b]naphthalene-4a-carboxylic acid ethyl ester,
(R)-1-(4-Fluorophenyl)-6-(6-morpholin-4-yl-pyridine-3-sulfonyl]-1,4,5,6,7,8-hexahydro-1,2,6-triaza-cyclopenta[b]naphthalene-4a-carboxylic acid isopropyl ester,
(R)-1-(4-Fluorophenyl)-6-(6-morpholin-4-yl-pyridine-3-sulfonyl]-1,4,5,6,7,8-hexahydro-1,2,6-triaza-cyclopenta[b]naphthalene-4a-carboxylic acid cyclobutyl ester,
(R)-1-(4-Fluorophenyl)-6-(6-morpholin-4-yl-pyridine-3-sulfonyl]-1,4,5,6,7,8-hexahydro-1,2,6-triaza-cyclopenta[b]naphthalene-4a-carboxylic acid cyclopropylmethyl ester,
(R)-1-(4-Fluorophenyl)-6-(6-morpholin-4-yl-pyridine-3-sulfonyl]-1,4,5,6,7,8-hexahydro-1,2,6-triaza-cyclopenta[b]naphthalene-4a-carboxylic acid cyclobutylmethyl ester,
(R)-1-(4-Fluorophenyl)-6-(6-morpholin-4-yl-pyridine-3-sulfonyl]-1,4,5,6,7,8-hexahydro-1,2,6-triaza-cyclopenta[b]naphthalene-4a-carboxylic acid 3-hydroxycyclobutyl-methyl ester,
(R)-1-(4-Fluorophenyl)-6-(6-morpholin-4-yl-pyridine-3-sulfonyl]-1,4,5,6,7,8-hexahydro-1,2,6-triaza-cyclopenta[b]naphthalene-4a-carboxylic acid 3-methyloxetan-3-yl-methyl ester,
(R)-1-(4-Fluorophenyl)-6-(6-morpholin-4-yl-pyridine-3-sulfonyl]-1,4,5,6,7,8-hexahydro-1,2,6-triaza-cyclopenta[b]naphthalene-4a-carboxylic acid 2-hydroxethyl ester,
(R)-1-(4-Fluorophenyl)-6-(6-morpholin-4-yl-pyridine-3-sulfonyl]-1,4,5,6,7,8-hexahydro-1,2,6-triaza-cyclopenta[b]naphthalene-4a-carboxylic acid 2-dimethylaminoethyl ester,
(R)-1-(4-Fluorophenyl)-6-(6-morpholin-4-yl-pyridine-3-sulfonyl]-1,4,5,6,7,8-hexahydro-1,2,6-triaza-cyclopenta[b]naphthalene-4a-carboxylic acid 5-methylisoxazol-3-ylmethyl ester,
(R)-1-(4-Fluorophenyl)-6-(6-morpholin-4-yl-pyridine-3-sulfonyl]-1,4,5,6,7,8-hexahydro-1,2,6-triaza-cyclopenta[b]naphthalene-4a-carboxylic acid cyclopropylmethyl ester,
(R)-1-(4-Fluorophenyl)-6-(6-methoxy pyridine-3-sulfonyl)-1,4,5,6,7,8-hexahydro-1,2,6-triaza-cyclopenta[b]naphthalene-4a-carboxylic acid cyclobutylmethyl ester,
(R)-1-(4-Fluorophenyl)-6-[6-((R)-3-fluoropyrrolidin-1-yl)-pyridine-3-sulfonyl]-1,4,5,6,7,8-hexahydro-1,2,6-triaza-cyclopenta[b]naphthalene-4a-carboxylic acid 5-methylisoxazol-3-ylmethyl ester,
(R)-1-(4-Fluorophenyl)-6-[6-((R)-3-fluoropyrrolidin-1-yl)-pyridine-3-sulfonyl]-1,4,5,6,7,8-hexahydro-1,2,6-triaza-cyclopenta[b]naphthalene-4a-carboxylic acid 3-hydroxy cyclobutylmethyl ester,
(S)-1-[(S)-1-(4-Fluorophenyl)-6-[6-morpholin-4-yl-pyridine-3-sulfonyl)-1,4,5,6,7,8-hexahydro-1,2,6-triaza-cyclopenta[b]naphthalene-4a-ylmethyl]-pyrrolidin-3-ol,
(R)-1-[(S)-1-(4-Fluorophenyl)-6-[6-morpholin-4-yl-pyridine-3-sulfonyl)-1,4,5,6,7,8-hexahydro-1,2,6-triaza-cyclopenta[b]naphthalene-4a-ylmethyl]-pyrrolidin-3-ol, or
(R)-1-(4-Fluoro-phenyl)-4a-(2-methoxy-ethoxymethyl)-6-(6-morpholin-4-yl-pyridine-3-sulfonyl)-4,4a,5,6,7,8-hexahydro-1H-1,2,6-traza-cyclopenta[b]naphthalene.

It will be apparent to one skilled in the art that certain compounds of this invention may exist in tautomeric forms, all such tautomeric forms of the compounds being within the scope of the invention.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention.

Unless otherwise stated, structures depicted herein are also meant to include compounds which differ only in the presence of one or more isotopically enriched atoms. For example, compounds having the present structures except for the replacement of a hydrogen by a deuterium or tritium, the replacement of a carbon by $^{13}$C- or $^{14}$C-enriched carbon, or the replacement of an iodine by $^{125}$I, are within the scope of this invention. All isotopic variations of the compounds of the present invention, whether radioactive or not, are encompassed within the scope of the present invention.

The compounds of the present invention also include the salts, hydrates, solvates and prodrug forms. The compounds of the present invention also include the isomers and metabolites of those described in Formula I.

Salts include, but are not limited to, sulfate, citrate, acetate, oxalate, chloride, bromide, iodide, nitrate, bisulfate, phosphate, acid phosphate, phosphonic acid, isonicotinate, lactate, salicylate, citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts. Other salts include, but are not limited to, salts with inorganic bases including alkali metal salts such as sodium salts, and potassium salts; alkaline earth metal salts such as calcium salts, and magnesium salts; aluminum salts; and ammonium salts. Other salts with organic bases include salts with diethylamine, diethanolamine, meglumine, and N,N'-dibenzylethylenediamine.

Pharmaceutically acceptable salts of the acidic compounds of the present invention are salts formed with bases, namely cationic salts such as alkali and alkaline earth metal salts, such as sodium, lithium, potassium, calcium, magnesium, as well as ammonium salts, such as ammonium, trimethyl-ammonium, diethylammonium, and tris-(hydroxymethyl)-methyl-ammonium salts.

Similarly acid addition salts, such as mineral acids, organic carboxylic and organic sulfonic acids, e.g., hydrochloric acid, methanesulfonic acid, maleic acid, are also possible provided a basic group, such as pyridyl, constitutes part of the structure.

The neutral forms of the compounds can be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present invention. The compounds of the present invention do not include those which are known in art to be too unstable to synthesize and/or isolate. The present invention is meant to include compounds in racemic and optically pure forms. Optically active (R)- and (S)-, or (D)- and (L)-isomers may be prepared using chiral synthons or chiral reagents, or resolved using conventional techniques.

The present invention also provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

The compounds of the invention can be synthesized by a variety of methods known to one of skill in the art (see *Comprehensive Organic Transformations* Richard C. Larock, 1989) or by an appropriate combination of generally well known synthetic methods. Techniques useful in synthesizing the compounds of the invention are both readily apparent and accessible to those of skill in the relevant art. The discussion below is offered to illustrate certain of the diverse methods available for use in assembling the compounds of the invention. However, the discussion is not intended to define the scope of reactions or reaction sequences that are useful in preparing the compounds of the present invention. One of skill in the art will appreciate that other methods of making the compounds are useful in the present invention. Although some compounds in FIG. 1, FIG. 2, and Table 1 may indicate relative stereochemistry, the compounds may exist as a racemic mixture or as either enantiomer.

The compounds of the invention are synthesized by an appropriate combination of generally well known synthetic methods. Techniques useful in synthesizing the compounds of the invention are both readily apparent and accessible to those of skill in the relevant art. The discussion below is offered to illustrate certain of the diverse methods available for use in assembling the compounds of the invention. However, the discussion is not intended to define the scope of reactions or reaction sequences that are useful in preparing the compounds of the present invention.

Compounds of the present invention can be prepared as shown in FIG. 1. Starting materials can be obtained via commercial sources, known synthetic methods, and methods described in U.S. Pat. No. 7,928,237, incorporated herein by reference. Esters I are converted to alcohols II by treatment with a reducing agent such as DIBAL-H, LiAlH$_4$ or RED-AL, preferable DIBAL-H in an inert solvent such as dichloromethane, tetrahydrofuran, benzene or toluene, preferably dichloromethane. Alcohols II are converted into ether derivatives III by treatment with a base (e.g. sodium hydride) in an aprotic solvent such as tetrahydrofuran, N,N-dimethylformamide, preferably tetrahydrofuran followed by addition of a substituted or unsubstituted alkyl, substituted or unsubstituted heteroalkyl, substituted or unsubstituted arylalkyl halide or methanesulfonate. The tert-butoxycarbonyl protecting group is removed from III by treatment with an acid, such as HCl, HBr, p-toluensulfonic acid or methanesulfonic acid, preferably HCl in a solvent such as dioxane, ethanol or tetrahydrofuran, preferably dioxane, either under anhydrous or aqueous conditions. Amines IV are converted to the subject compounds VI by treatment with an amino-substituted pyridylsulfonyl halide, such as the 2-substituted amino-5-chlorosulfonylpyridine V, in an inert solvent such as dichloromethane, toluene or tetrahydrofuran, preferably dichloromethane, in the presence of a base such as N,N-diisopropylethylamine or triethylamine. Subject compounds VI can also be prepared in a two-step sequence beginning with reaction of amines IV with a chloro (or bromo)-substituted pyridinesulfonyl chloride, such as 2-chloro-5-chlorosulfonylpyridine VII, to afford a halo-substituted pyridinesulfonamide derivative exemplified by VIII. Treatment of VIII with an amine in an inert solvent, such as tetrahydrofuran, toluene or N,N-dimethylformamide, optionally in the presence of a palladium catalyst (e.g. BINAP/Pd$_2$(dba)$_3$ and a base (e.g. sodium or potassium tert-butoxide), optionally under microwave conditions, affords the subject compounds VI.

Figure 2:
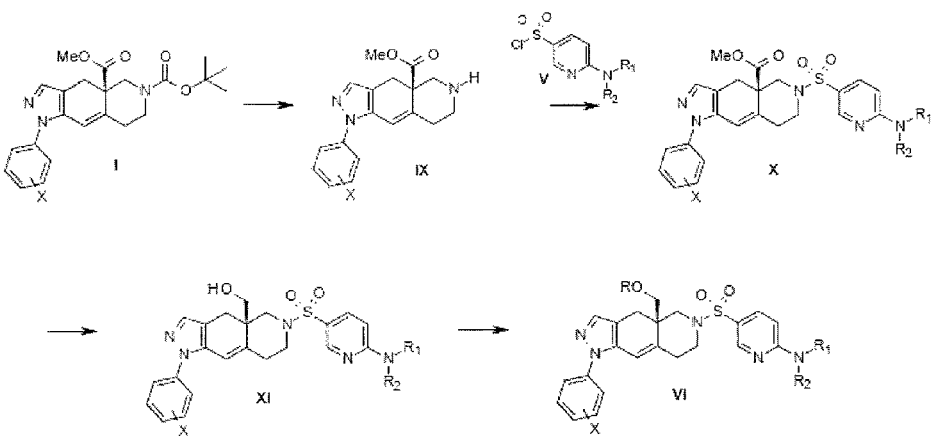
FIG. 2 shows alternative methods of making compounds of the present invention.

Compounds of the present invention can also be prepared as shown in FIG. 2. The tert-butoxycarbonyl protecting group is removed from I by treatment with an acid, such as HCl, HBr, p-toluensulfonic acid or methanesulfonic acid, preferably HCl in a solvent such as dioxane, ethanol or tetrahydrofuran, preferably dioxane, either under anhydrous or aqueous conditions to afford amines IX. Amines IX are converted to the pyridinesulfonamides X by treatment with an amino-substituted pyridylsulfonyl halide, such as the 2-substituted amino-5-chlorosulfonylpyridine V, in an inert solvent such as dichloromethane, toluene or tetrahydrofuran, preferably dichloromethane, in the presence of a base such as N,N-diisopropylethylamine or triethylamine. Reduction of the ester group in X by treatment with a reducing agent such as DIBAL-H, LiAlH$_4$ or RED-AL, preferable DIBAL-H in an inert solvent such as dichloromethane, tetrahydrofuran, benzene or toluene, preferably dichloromethane affords alcohols XI. Alcohols XI are converted into subject compounds VI by treatment with a base (e.g. sodium hydride) in an aprotic solvent such as acetonitrile, dimethylsulfoxide, tetrahydrofuran or N,N-dimethylformamide, preferably tetrahydrofuran followed by addition of a substituted or unsubstituted alkyl, substituted or unsubstituted heteroalkyl, substituted or unsubstituted arylalkyl halide or methanesulfonate. For the preparation of compounds VI in which R=CHF$_2$ the alkylation reagents can be FSO$_2$CF$_2$CO$_2$H in the presence of CuI.

Figure 3:
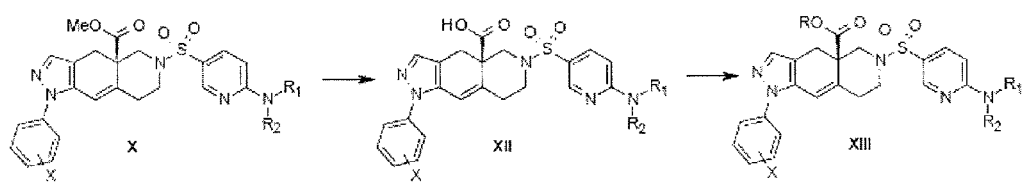
FIG. 3 shows alternative methods of making compounds of the present invention.

Compounds of the present invention can also be prepared as show in FIG. 3. Hydrolysis of esters X by treatment with a base, such as lithium hydroxide, in aqueous tetrahydrofuran affords acids XII which can be converted into esters by conversion to the acid chloride, e.g., with reaction with oxalyl chloride in dichloromethane, followed by treatment with the requisite alcohol in dichloromethane in the presence of triethylamine. Alternatively, acids XII can be alkylated with the appropriate alkyl halide under phase transfer conditions (tetrabutylammonium iodide, aqueous sodium hydroxide, tetrahydrofuran) or in N,N-dimethylformamide with cesium carbonate as base to form esters XIII.

Figure 4:
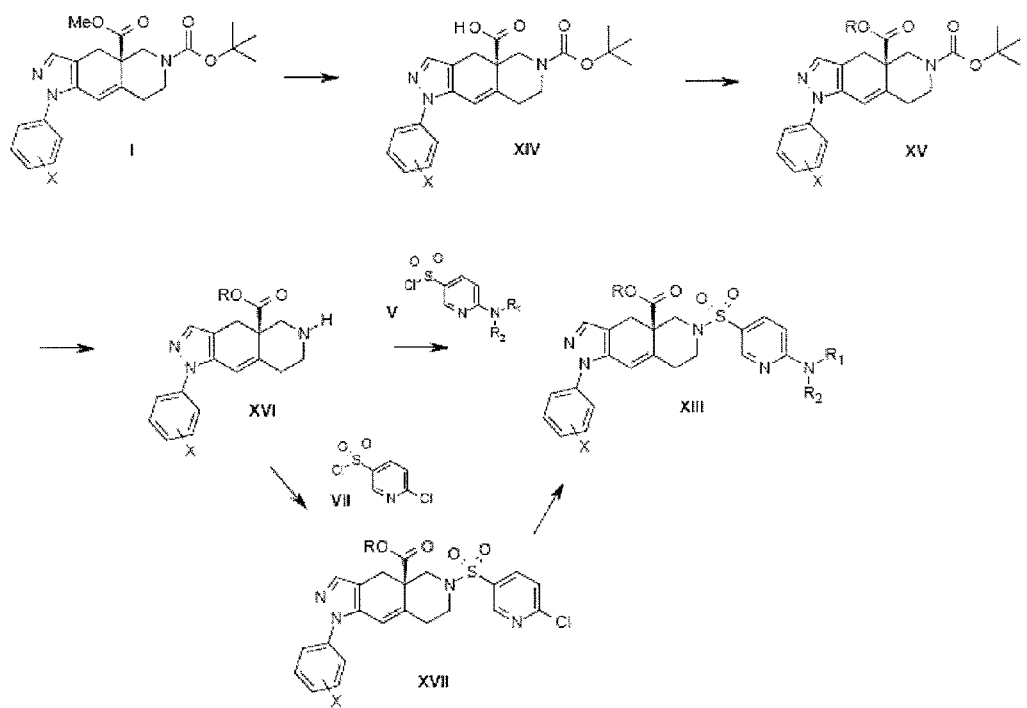
FIG. 4 shows alternative methods of making compounds of the present invention.

Compounds of the present invention can also be prepared as show in FIG. 4. Acids XIV, prepared by hydrolysis of ester I, are converted to esters XV as described for the preparation of esters XIII in FIG. 3. Conversion of esters XV to subject compounds XIII is effected as described for the preparation of subject compounds VI and VIII in FIG. 1, beginning with removal of the tert-butoxycarbonyl protecting group from XV. The resulting amine XVI is then converted to product XIII by reaction with an amino-substituted pyridylsulfonyl halide V. Alternatively, the ester-amine XVI is reacted with a halo-substituted pyridinesulfonyl chloride VII to afford a halo-substituted pyridinesulfonamide derivative XVII, which is then treated with an amine to afford product XIII.

Figure 5:
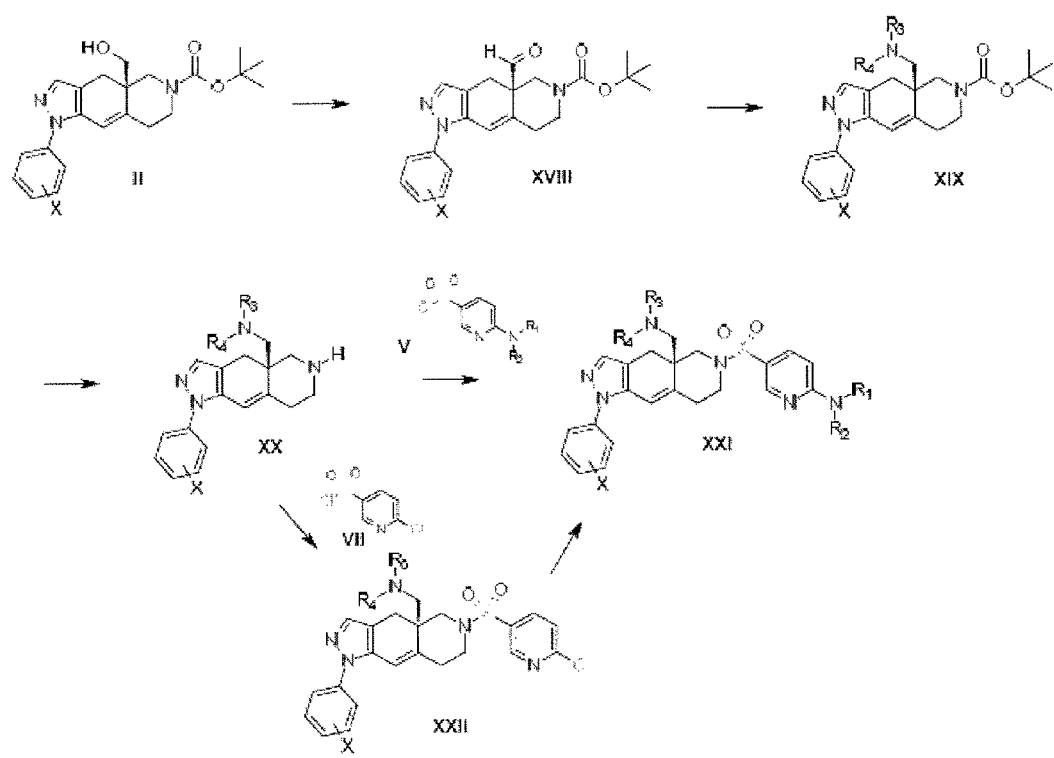
FIG. 5 shows alternative methods of making compounds of the present invention.

Compounds of the present invention can also be prepared as show in FIG. 5. Alcohols II can be oxidized to aldehydes XVIII using the Swern reaction (oxalyl chloride, dimethylsulfoxide, triethylamine in dichloromethane). Reductive amination with the requisite amine is effected with solium triacetoxyborohydride in dichloromethane to afford substituted amines XIX. Removal of the tert-butoxycarbonyl group with trifluoroacetic acid in dichloromethane affords diamines XX which are converted to subject compounds XXII as described for the preparation of subject compounds VI and VIII in FIG. 1, beginning with removal of the tert-butoxycarbonyl protecting group from XIX. The resulting amine XX is then converted to product XXI by reaction with an amino-substituted pyridylsulfonyl halide V. Alternatively, the amine XX is reacted with a halo-substituted pyridinesulfonyl chloride VII to afford a halo-substituted pyridinesulfonamide derivative XXII, which is then treated with an amine to afford product XXI.

Figure 6:
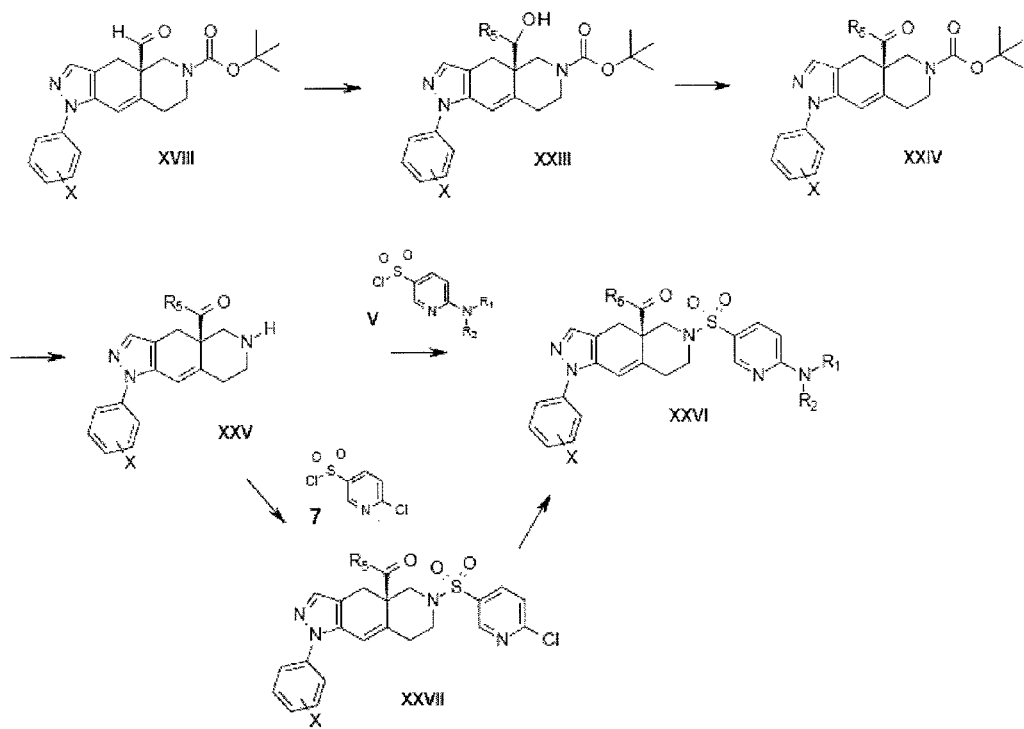
FIG. 6 shows alternative methods of making compounds of the present invention.

Compounds of the present invention can also be prepared as show in FIG. 6. Treatment of aldehydes XVIII with an organometallic reagent, such as an organolithium derivative $R_5Li$ or a Grignard reagent $R_5MgCl$ or $R_5MgBr$, in a suitable inert solvent such as diethyl ether or tetrahydrofuran affords alcohols XXIII. Oxidation to ketones XXIV is carried out with the Dess-Martin periiodinane reagent. Standard deprotection, e.g., with aqueous hydrochloric acid in dioxane, then provides amines XXV which are converted to subject compounds XXVI as described for the preparation of subject compounds VI and VIII in FIG. 1, beginning with removal of the tert-butoxycarbonyl protecting group from XXIV. The resulting amine XXV is then converted to product XXVI by reaction with an amino-substituted pyridylsulfonyl halide V. Alternatively, the amine XXV is reacted with a halo-substituted pyridinesulfonyl chloride VII to afford a halo-substituted pyridinesulfonamide derivative XXVII, which is then treated with an amine to afford product XXVI.

It will be appreciated that substitution of the pyridinesulfonyl chlorides V and VII in FIGS. 1-6 with appropriately substituted heteroaryl sulfonyl halides provides additional compounds of Formula I as described in the Summary of the Invention.

IV. Assays and Methods for Modulating Glucocorticoid Receptor Activity

The compounds of the present invention can be tested for their antiglucocorticoid properties. Methods of assaying compounds capable of modulating glucocorticoid receptor activity are presented herein. Typically, compounds of the present invention are capable of modulating glucocorticoid receptor activity by selectively binding to the GR or by preventing GR ligands from binding to the GR. In some embodiments, the compounds exhibit little or no cytotoxic effect. Therefore, exemplary assays disclosed herein may test the ability of compounds to (1) bind to the GR; (2) selectively bind to the GR; (3) prevent GR ligands from binding to the GR; (4) modulate the activity of the GR in a cellular system; and/or (5) exhibit non-cytotoxic effects.

Binding Assays

In some embodiments, GR modulators are identified by screening for molecules that compete with a ligand of GR, such as dexamethasone. Those of skill in the art will recognize that there are a number of ways to perform competitive binding assays. In some embodiments, GR is pre-incubated with a labeled GR ligand and then contacted with a test compound. This type of competitive binding assay may also be referred to herein as a binding displacement assay. Alteration (e.g. a decrease) of the quantity of ligand bound to GR indicates that the molecule is a potential GR modulator. Alternatively, the binding of a test compound to GR can be measured directly with a labeled test compound. This latter type of assay is called a direct binding assay.

Both direct binding assays and competitive binding assays can be used in a variety of different formats. The formats may be similar to those used in immunoassays and receptor binding assays. For a description of different formats for binding assays, including competitive binding assays and direct binding assays, see *Basic and Clinical Immunology* 7th Edition (D. Stites and A. Ten ed.) 1991; *Enzyme Immunoassay*, E. T. Maggio, ed., CRC Press, Boca Raton, Fla. (1980); and "Practice and Theory of Enzyme Immunoassays," P. Tijssen, *Laboratory Techniques in Biochemistry and Molecular Biology*, Elsevier Science Publishers B.V. Amsterdam (1985), each of which is incorporated herein by reference.

In solid phase competitive binding assays, for example, the sample compound can compete with a labeled analyte for specific binding sites on a binding agent bound to a solid surface. In this type of format, the labeled analyte can be a GR ligand and the binding agent can be GR bound to a solid phase. Alternatively, the labeled analyte can be labeled GR and the binding agent can be a solid phase GR ligand. The concentration of labeled analyte bound to the capture agent is inversely proportional to the ability of a test compound to compete in the binding assay.

Alternatively, the competitive binding assay may be conducted in liquid phase, and any of a variety of techniques known in the art may be used to separate the bound labeled protein from the unbound labeled protein. For example, several procedures have been developed for distinguishing between bound ligand and excess bound ligand or between bound test compound and the excess unbound test compound. These include identification of the bound complex by sedimentation in sucrose gradients, gel electrophoresis, or gel isoelectric focusing; precipitation of the receptor-ligand complex with protamine sulfate or adsorption on hydroxylapatite; and the removal of unbound compounds or ligands by adsorption on dextran-coated charcoal (DCC) or binding to immobilized antibody. Following separation, the amount of bound ligand or test compound is determined.

Alternatively, a homogenous binding assay may be performed in which a separation step is not needed. For example, a label on the GR may be altered by the binding of the GR to its ligand or test compound. This alteration in the labeled GR results in a decrease or increase in the signal emitted by label, so that measurement of the label at the end of the binding assay allows for detection or quantitation of the GR in the bound state. A wide variety of labels may be used. The component may be labeled by any one of several methods. Useful radioactive labels include those incorporating $^3H$, $^{125}I$, $^{35}S$, $^{14}C$, or $^{32}P$. Useful non-radioactive labels include those incorporating fluorophores, chemiluminescent agents, phosphorescent agents, electrochemiluminescent agents, and the like. Fluorescent agents are especially useful in analytical techniques that are used to detect shifts in protein structure such as fluorescence anisotropy and/or fluorescence polarization. The choice of label depends on sensitivity required, ease of conjugation with the compound, stability requirements, and available instrumentation. For a review of various labeling or signal producing systems which may be used, see U.S. Pat. No. 4,391,904, which is incorporated herein by reference in its entirety for all purposes. The label may be coupled directly or indirectly to the desired component of the assay according to methods well known in the art.

For competitive binding assays, the amount of inhibition may be determined using the techniques disclosed herein. The amount of inhibition of ligand binding by a test compound depends on the assay conditions and on the concentrations of ligand, labeled analyte, and test compound that are used. In an exemplary embodiment, a compound is said to be capable of inhibiting the binding of a GR ligand to a GR in a competitive binding assay if the inhibition constant ($K_i$) is less than 5 µM using the assay conditions presented in Example 65. In another exemplary embodiment, a compound is said to be capable of inhibiting the binding of a GR ligand to a GR in a competitive binding assay if the $K_i$ is less than 1 µM using the assay conditions presented in Example 65. In another exemplary embodiment, a compound is said to be capable of inhibiting the binding of a GR ligand to a GR in a competitive binding assay if the $K_i$ is less than 100 nM using the assay conditions presented in Example 65. In another exemplary embodiment, a compound is said to be capable of inhibiting the binding of a GR ligand to a GR in a competitive binding assay if the $K_i$ is less than 10 nM using the assay conditions presented in Example 65. In another exemplary embodiment, a compound is said to be capable of inhibiting the binding of a GR ligand to a GR in a competitive binding assay if the $K_i$ is less than 1 nM using the assay conditions presented in Example 65. In another exemplary embodiment, a compound is said to be capable of inhibiting the binding of a GR ligand to a GR in a competitive binding assay if the $K_i$ is less than 100 pM using the assay conditions presented in Example 65. In another exemplary embodiment, a compound is said to be capable of inhibiting the binding of a GR ligand to a GR in a competitive binding assay if the $K_i$ is less than 10 pM using the assay conditions presented in Example 65.

High-throughput screening methods may be used to assay a large number of potential modulator compounds. Such "compound libraries" are then screened in one or more assays, as described herein, to identify those library members (particular chemical species or subclasses) that display a desired characteristic activity. Preparation and screening of chemical libraries is well known to those of skill in the art. Devices for the preparation of chemical libraries are commercially available (see, e.g., 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.).

Cell-Based Assays

Cell-based assays involve whole cells or cell fractions containing GR to assay for binding or modulation of activity of GR by a compound of the present invention. Exemplary cell types that can be used according to the methods of the invention include, e.g., any mammalian cells including leukocytes such as neutrophils, monocytes, macrophages, eosinophils, basophils, mast cells, and lymphocytes, such as T cells and B cells, leukemias, Burkitt's lymphomas, tumor cells (including mouse mammary tumor virus cells), endothelial cells, fibroblasts, cardiac cells, muscle cells, breast tumor cells, ovarian cancer carcinomas, cervical carcinomas, glioblastomas, liver cells, kidney cells, and neuronal cells, as well as fungal cells, including yeast. Cells can be primary cells or tumor cells or other types of immortal cell lines. Of course, GR can be expressed in cells that do not express an endogenous version of GR.

In some cases, fragments of GR, as well as protein fusions, can be used for screening. When molecules that compete for binding with GR ligands are desired, the GR fragments used are fragments capable of binding the ligands (e.g., dexamethasone). Alternatively, any fragment of GR can be used as a target to identify molecules that bind GR. GR fragments can include any fragment of, e.g., at least 20, 30, 40, 50 amino acids up to a protein containing all but one amino acid of GR. Typically, ligand-binding fragments will comprise the ligand binding domain and/or N-terminal regulatory, DNA-binding, hinge region, and C-terminal domain domains of GR.

In some embodiments, signaling triggered by GR activation is used to identify GR modulators. Signaling activity of GR can be determined in many ways. For example, downstream molecular events can be monitored to determine signaling activity. Downstream events include those activities or manifestations that occur as a result of stimulation of a GR receptor. Exemplary downstream events useful in the functional evaluation of transcriptional activation and antagonism in unaltered cells include upregulation of a number of glucocorticoid response element (GRE)-dependent genes (PEPCK, tyrosine amino transferase, aromatase). In addition, specific cell types susceptible to GR activation may be used, such as osteocalcin expression in osteoblasts which is downregulated by glucocorticoids; primary hepatocytes which exhibit glucocorticoid mediated upregulation of PEPCK and glucose-6-phospahte (G-6-Pase)). GRE-mediated gene expression has also been demonstrated in transfected cell lines using well-known GRE-regulated sequences (e.g. the mouse mammary tumor virus promoter (MMTV) transfected upstream of a reporter gene construct). Examples of useful reporter gene constructs include luciferase (luc), alkaline phosphatase (ALP) and chloramphenicol acetyl transferase (CAT). The functional evaluation of transcriptional repression can be carried out in cell lines such as monocytes or human skin fibroblasts. Useful functional assays include those that measure IL-1beta stimulated IL-6 expression; the downregulation of collagenase, cyclooxygenase-2 and various chemokines (MCP-1, RANTES); or expression of genes regulated by NFkB or AP-1 transcription factors in transfected cell-lines. An example of a cell-based assay measuring gene transcription is presented in Example 66.

V. Pharmaceutical Compositions of Glucocorticoid Receptor Modulators

In another embodiment, the present invention provides a pharmaceutical composition, comprising a compound of Formula I and a pharmaceutically acceptable excipient.

The compounds of the present invention can be prepared and administered in a wide variety of oral, parenteral and topical dosage forms. Oral preparations include tablets, pills, powder, dragees, capsules, liquids, lozenges, cachets, gels, syrups, slurries, suspensions, etc., suitable for ingestion by the patient. The compounds of the present invention can also be administered by injection, that is, intravenously, intramuscularly, intracutaneously, subcutaneously, intraduodenally, or intraperitoneally. Also, the compounds described herein can be administered by inhalation, for example, intranasally. Additionally, the compounds of the present invention can be administered transdermally. The GR modulators of this invention can also be administered by intraocular, intravaginal, and intrarectal routes including suppositories, insufflation, powders and aerosol formulations (for examples of steroid inhalants, see Rohatagi, *J. Clin. Pharmacol.* 35:1187-1193, 1995; Tjwa, *Ann. Allergy Asthma Immunol.* 75:107-111, 1995). Accordingly, the present invention also provides pharmaceutical compositions including a pharmaceutically acceptable carrier or excipient and either a compound of Formula (I), or a pharmaceutically acceptable salt of a compound of Formula (I).

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances, which may also act as diluents, flavoring agents, binders, preservatives, tablet disintegrating agents, or an encapsulating material. Details on techniques for formulation and administration are well described in the scientific and patent literature, see, e.g., the latest edition of Remington's Pharmaceutical Sciences, Maack Publishing Co, Easton Pa. ("Remington's").

In powders, the carrier is a finely divided solid, which is in a mixture with the finely divided active component. In tablets, the active component is mixed with the carrier having the necessary binding properties in suitable proportions and compacted in the shape and size desired. The powders and tablets preferably contain from 5% or 10% to 70% of the active compound.

Suitable solid excipients include, but are not limited to, magnesium carbonate; magnesium stearate; talc; pectin; dextrin; starch; tragacanth; a low melting wax; cocoa butter; carbohydrates; sugars including, but not limited to, lactose, sucrose, mannitol, or sorbitol, starch from corn, wheat, rice, potato, or other plants; cellulose such as methyl cellulose, hydroxypropylmethyl-cellulose, or sodium carboxymethyl-cellulose; and gums including arabic and tragacanth; as well as proteins including, but not limited to, gelatin and collagen. If desired, disintegrating or solubilizing agents may be added, such as the cross-linked polyvinyl pyrrolidone, agar, alginic acid, or a salt thereof, such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound (i.e., dosage). Pharmaceutical preparations of the invention can also be used orally using, for example, push-fit capsules made of gelatin, as well as soft, sealed capsules made of gelatin and a coating such as glycerol or sorbitol. Push-fit capsules can contain GR modulator mixed with a filler or binders such as lactose or starches, lubricants such as talc or magnesium stearate, and, optionally, stabilizers. In soft capsules, the GR modulator compounds may be dissolved or suspended in suitable liquids, such as fatty oils, liquid paraffin, or liquid polyethylene glycol with or without stabilizers.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution.

Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate). The aqueous suspension can also contain one or more preservatives such as ethyl or n-propyl p-hydroxybenzoate, one or more coloring agents, one or more flavoring agents and one or more sweetening agents, such as sucrose, aspartame or saccharin. Formulations can be adjusted for osmolarity.

Also included are solid form preparations, which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

Oil suspensions can be formulated by suspending a GR modulator in a vegetable oil, such as arachis oil, olive oil, sesame oil or coconut oil, or in a mineral oil such as liquid paraffin; or a mixture of these. The oil suspensions can contain a thickening agent, such as beeswax, hard paraffin or cetyl alcohol. Sweetening agents can be added to provide a palatable oral preparation, such as glycerol, sorbitol or sucrose. These formulations can be preserved by the addition of an antioxidant such as ascorbic acid. As an example of an injectable oil vehicle, see Minto, *J. Pharmacol. Exp. Ther.* 281:93-102, 1997. The pharmaceutical formulations of the invention can also be in the form of oil-in-water emulsions. The oily phase can be a vegetable oil or a mineral oil, described above, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening agents and flavoring agents, as in the formulation of syrups and elixirs. Such formulations can also contain a demulcent, a preservative, or a coloring agent.

VI. Administration

The GR modulators of the invention can be delivered by transdermally, by a topical route, formulated as applicator sticks, solutions, suspensions, emulsions, gels, creams, ointments, pastes, jellies, paints, powders, and aerosols.

The GR modulators of the invention can also be delivered as microspheres for slow release in the body. For example, microspheres can be administered via intradermal injection of drug-containing microspheres, which slowly release subcutaneously (see Rao, *J. Biomater Sci. Polym. Ed.* 7:623-645, 1995; as biodegradable and injectable gel formulations (see, e.g., Gao *Pharm. Res.* 12:857-863, 1995); or, as microspheres for oral administration (see, e.g., Eyles, *J. Pharm. Pharmacol.* 49:669-674, 1997). Both transdermal and intradermal routes afford constant delivery for weeks or months.

The GR modulator pharmaceutical formulations of the invention can be provided as a salt and can be formed with many acids, including but not limited to hydrochloric, sulfuric, acetic, lactic, tartaric, malic, succinic, etc. Salts tend to be more soluble in aqueous or other protonic solvents that are the corresponding free base forms. In other cases, the preparation may be a lyophilized powder in 1 mM-50 mM histidine, 0.1%-2% sucrose, 2%-7% mannitol at a pH range of 4.5 to 5.5, that is combined with buffer prior to use.

In another embodiment, the GR modulator formulations of the invention are useful for parenteral administration, such as intravenous (IV) administration or administration into a body cavity or lumen of an organ. The formulations for administration will commonly comprise a solution of the GR modulator dissolved in a pharmaceutically acceptable carrier. Among the acceptable vehicles and solvents that can be employed are water and Ringer's solution, an isotonic sodium chloride. In addition, sterile fixed oils can conventionally be employed as a solvent or suspending medium. For this purpose any bland fixed oil can be employed including synthetic mono- or diglycerides. In addition, fatty acids such as oleic acid can likewise be used in the preparation of injectables. These solutions are sterile and generally free of undesirable matter. These formulations may be sterilized by conventional, well known sterilization techniques. The formulations may contain pharmaceutically acceptable auxiliary substances as required to approximate physiological conditions such as pH adjusting and buffering agents, toxicity adjusting agents, e.g., sodium acetate, sodium chloride, potassium chloride, calcium chloride, sodium lactate and the like. The concentration of GR modulator in these formulations can vary widely, and will be selected primarily based on fluid volumes, viscosities, body weight, and the like, in accordance with the particular mode of administration selected and the patient's needs. For IV administration, the formulation can be a sterile injectable preparation, such as a sterile injectable aqueous or oleaginous suspension. This suspension can be formulated according to the known art using those suitable dispersing or wetting agents and suspending agents. The sterile injectable preparation can also be a sterile injectable solution or suspension in a nontoxic parenterally-acceptable diluent or solvent, such as a solution of 1,3-butanediol.

In another embodiment, the GR modulator formulations of the invention can be delivered by the use of liposomes which fuse with the cellular membrane or are endocytosed, i.e., by employing ligands attached to the liposome, or attached directly to the oligonucleotide, that bind to surface membrane protein receptors of the cell resulting in endocytosis. By using liposomes, particularly where the liposome surface carries ligands specific for target cells, or are otherwise preferentially directed to a specific organ, one can focus the delivery of the GR modulator into the target cells in vivo. (See, e.g., Al-Muhammed, *J. Microencapsul.* 13:293-306, 1996; Chonn, *Curr. Opin. Biotechnol.* 6:698-708, 1995; Ostro, *Am. J. Hosp. Pharm.* 46:1576-1587, 1989).

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 0.1 mg to 10000 mg, more typically 1.0 mg to 1000 mg, most typically 10 mg to 500 mg, according to the particular application and the potency of the active component. The composition can, if desired, also contain other compatible therapeutic agents.

The compounds described herein can be used in combination with one another, with other active agents known to be useful in modulating a glucocorticoid receptor, or with adjunctive agents that may not be effective alone, but may contribute to the efficacy of the active agent.

In some embodiments, co-administration includes administering one active agent within 0.5, 1, 2, 4, 6, 8, 10, 12, 16, 20, or 24 hours of a second active agent. Co-administration includes administering two active agents simultaneously, approximately simultaneously (e.g., within about 1, 5, 10, 15, 20, or 30 minutes of each other), or sequentially in any order. In some embodiments, co-administration can be accomplished by co-formulation, i.e., preparing a single pharmaceutical composition including both active agents. In other embodiments, the active agents can be formulated separately. In another embodiment, the active and/or adjunctive agents may be linked or conjugated to one another.

VII. Methods

In another embodiment, the present invention provides methods of modulating glucocorticoid receptor activity. In an exemplary embodiment, the method includes contacting a GR with an effective amount of a compound of the present invention, such as the compound of Formula (I), and detecting a change in GR activity.

In an exemplary embodiment, the GR modulator is an antagonist of GR activity (also referred to herein as "a glucocorticoid receptor antagonist"). A glucocorticoid receptor antagonist, as used herein, refers to any composition or compound which partially or completely inhibits (antagonizes) the binding of a glucocorticoid receptor (GR) agonist (e.g. cortisol and synthetic or natural cortisol analog) to a GR thereby inhibiting any biological response associated with the binding of a GR to the agonist.

In a related embodiment, the GR modulator is a specific glucocorticoid receptor antagonist. As used herein, a specific glucocorticoid receptor antagonist refers to a composition or compound which inhibits any biological response associated with the binding of a GR to an agonist by preferentially binding to the GR rather than another nuclear receptor (NR). Examples of nuclear receptors include the progesterone and mineralocorticoid receptors. In some embodiments, the specific glucocorticoid receptor antagonist binds preferentially to GR rather than the mineralocorticoid receptor (MR) or progesterone receptor (PR). In an exemplary embodiment, the specific glucocorticoid receptor antagonist binds preferentially to GR rather than the mineralocorticoid receptor (MR). In another exemplary embodiment, the specific glucocorticoid receptor antagonist binds preferentially to GR rather than the progesterone receptor (PR).

In a related embodiment, the specific glucocorticoid receptor antagonist binds to the GR with an association constant ($K_d$) that is at least 10-fold less than the $K_d$ for the NR. In another embodiment, the specific glucocorticoid receptor antagonist binds to the GR with an association constant ($K_d$) that is at least 100-fold less than the $K_d$ for the NR. In another embodiment, the specific glucocorticoid receptor antagonist binds to the GR with an association constant ($K_d$) that is at least 1000-fold less than the $K_d$ for the NR.

In some embodiments, the present invention provides a method of modulating a glucocorticoid receptor, the method including administering to a subject in need thereof, a therapeutically effective amount of a compound of the present invention.

In some embodiments, the present invention provides a method of treating a disorder or condition through modulating a glucocorticoid receptor, the method including administering to a subject in need thereof, a therapeutically effective amount of the compound of the present invention.

In some embodiments, the present invention provides a method of treating a disorder or condition through antagonizing a glucocorticoid receptor, the method comprising administering to a subject in need thereof, a therapeutically effective amount of the compound of the present invention.

A variety of disease states are capable of being treated with glucocorticoid receptor modulators of the present invention. Exemplary disease states include major psychotic depression, mild cognitive impairment, psychosis, dementia, hyperglycemia, stress disorders, antipsychotic induced weight gain, delirium, cognitive impairment in depressed patients, cognitive deterioration in individuals with Down's syndrome, psychosis associated with interferon-alpha therapy, chronic pain (e.g. pain associate with gastroesophageal reflux disease), postpartum psychosis, postpartum depression, neurological disorders in premature infants, migraine headaches, obesity, diabetes, cardiovascular disease, hypertension, Syndrome X, depression, anxiety, glaucoma, human immunodeficiency virus (HIV) or acquired immunodeficiency syndrome (AIDS), neurodegeneration (e.g. Alzheimer's disease and Parkinson's disease), cognition enhancement, Cushing's Syndrome, Addison's Disease, osteoperosis, frailty, inflammatory diseases (e.g., osteoarthritis, rheumatoid arthritis, asthma and rhinitis), adrenal function-related ailments, viral infection, immunodeficiency, immunomodulation, autoimmune diseases, allergies, wound healing, compulsive behavior, multi-drug resistance, addiction, psychosis, anorexia, cachexia, post-traumatic stress syndrome post-surgical bone fracture, medical catabolism, and muscle frailty. The methods of treatment includes administering to a patient in need of such treatment, a therapeutically effective amount of a compound of the present invention, or a pharmaceutically acceptable salt thereof.

Thus, in an exemplary embodiment, the present invention provides a method of treating a disorder or condition through modulating a GR, the method includes administering to a subject in need of such treatment, an effective amount of a compound of the present invention, such as a compound of Formula (I).

The amount of GR modulator adequate to treat a disease through modulating the GR is defined as a "therapeutically effective dose." The dosage schedule and amounts effective for this use, i.e., the "dosing regimen," will depend upon a variety of factors, including the stage of the disease or condition, the severity of the disease or condition, the general state of the patient's health, the patient's physical status, age and the like. In calculating the dosage regimen for a patient, the mode of administration also is taken into consideration.

The dosage regimen also takes into consideration pharmacokinetics parameters well known in the art, i.e., the rate of absorption, bioavailability, metabolism, clearance, and the like (see, e.g., Hidalgo-Aragones (1996) *J. Steroid Biochem. Mol. Biol.* 58:611-617; Groning (1996) *Pharmazie* 51:337-341; Fotherby (1996) *Contraception* 54:59-69; Johnson (1995) *J. Pharm. Sci.* 84:1144-1146; Rohatagi (1995) *Pharmazie* 50:610-613; Brophy (1983) *Eur. J. Clin. Pharmacol.* 24:103-108; the latest Remington's, supra). The state of the art allows the clinician to determine the dosage regimen for each individual patient, GR modulator and disease or condition treated.

Single or multiple administrations of GR modulator formulations can be administered depending on the dosage and frequency as required and tolerated by the patient. The formulations should provide a sufficient quantity of active agent to effectively treat the disease state. Thus, in one embodiment, the pharmaceutical formulations for oral administration of GR modulator is in a daily amount of between about 0.5 to about 20 mg per kilogram of body weight per day. In an alternative embodiment, dosages are from about 1 mg to about 4 mg per kg of body weight per patient per day are used. Lower dosages can be used, particularly when the drug is administered to an anatomically secluded site, such as the cerebral spinal fluid (CSF) space, in contrast to administration orally, into the blood stream, into a body cavity or into a lumen of an organ. Substantially higher dosages can be used in topical administration. Actual methods for preparing parenterally administrable GR modulator formulations will be known or apparent to those skilled in the art and are described in more detail in such publications as Remington's, supra. See also Nieman, In "Receptor Mediated Antisteroid Action," Agarwal, et al., eds., De Gruyter, New York (1987).

After a pharmaceutical composition including a GR modulator of the invention has been formulated in an acceptable carrier, it can be placed in an appropriate container and labeled for treatment of an indicated condition. For administration of GR modulators, such labeling would include, e.g., instructions concerning the amount, frequency and method of administration. In one embodiment, the invention provides for a kit for the treatment of delirium in a human which includes a GR modulator and instructional material teaching the indications, dosage and schedule of administration of the GR modulator.

The terms and expressions which have been employed herein are used as terms of description and not of limitation, and there is no intention in the use of such terms and expressions of excluding equivalents of the features shown and described, or portions thereof, it being recognized that various modifications are possible within the scope of the invention claimed. Moreover, any one or more features of any embodiment of the invention may be combined with any one or more other features of any other embodiment of the invention, without departing from the scope of the invention. For example, the features of the GR modulator compounds are equally applicable to the methods of treating disease states and/or the pharmaceutical compositions described herein. All publications, patents, and patent applications cited herein are hereby incorporated by reference in their entirety for all purposes.

TABLE 1

Activity Data for example compounds of the present invention

| Example No. | Compound Structure | GR Binding $K_i$ | GR Functional $K_i$ |
|---|---|---|---|
| Example 1 | 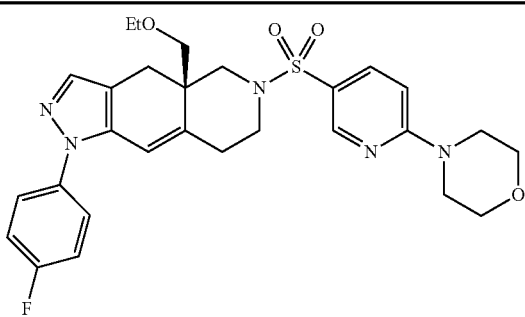 | +++ | +++ |

TABLE 1-continued

Activity Data for example compounds of the present invention

| Example No. | Compound Structure | GR Binding $K_i$ | GR Functional $K_i$ |
|---|---|---|---|
| Example 1c | 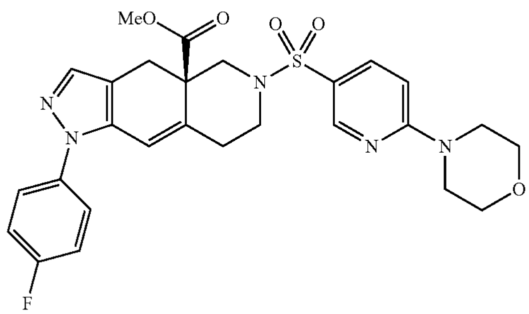 [SMILES: COC(=O)[C@]12Cc3cnn(-c4ccc(F)cc4)c3C=C1CCN(S(=O)(=O)c1ccc(N3CCOCC3)nc1)C2] | + | + |
| Example 1d | 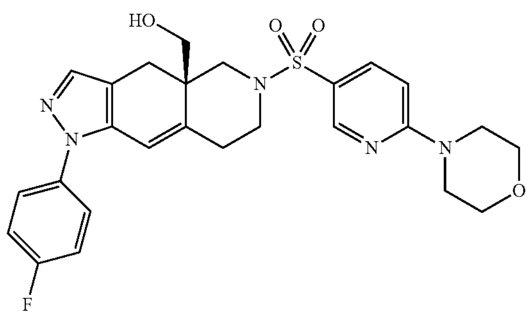 [SMILES: O=S(=O)(c1ccc(N2CCOCC2)nc1)N1CCC2=Cc3c(cnn3-c3ccc(F)cc3)C[C@]2(CO)C1] | + | + |
| Example 2 | 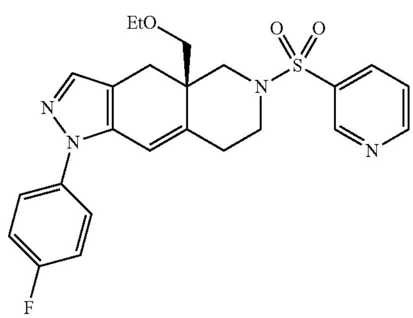 [SMILES: CCOC[C@]12Cc3cnn(-c4ccc(F)cc4)c3C=C1CCN(S(=O)(=O)c1cccnc1)C2] | ++ | ++ |
| Example 3 | 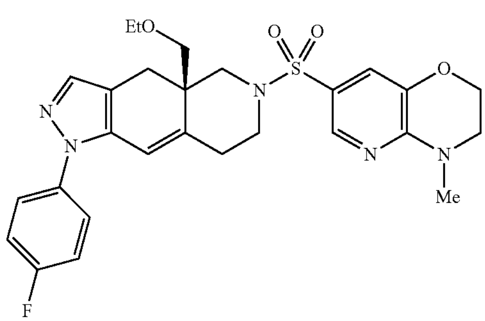 [SMILES: CCOC[C@]12Cc3cnn(-c4ccc(F)cc4)c3C=C1CCN(S(=O)(=O)c1cnc3c(c1)OCCN3C)C2] | +++ | ++ |

TABLE 1-continued

Activity Data for example compounds of the present invention

| Example No. | Compound Structure | GR Binding $K_i$ | GR Functional $K_i$ |
|---|---|---|---|
| Example 4 | 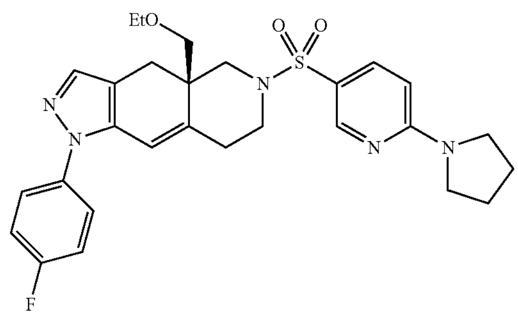 [SMILES: CCOC[C@]12Cc3cnn(-c4ccc(F)cc4)c3C=C1CCN(S(=O)(=O)c1ccc(N3CCCC3)nc1)C2] | + | ++ |
| Example 5 | 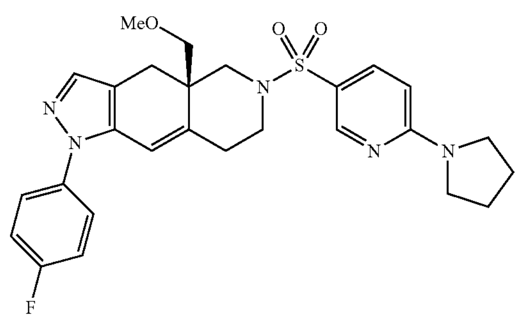 [SMILES: COC[C@]12Cc3cnn(-c4ccc(F)cc4)c3C=C1CCN(S(=O)(=O)c1ccc(N3CCCC3)nc1)C2] | ++ | ++ |
| Example 6 | 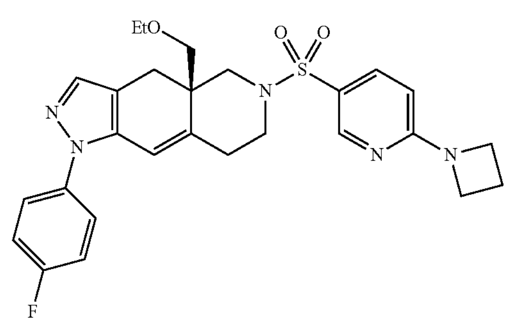 [SMILES: CCOC[C@]12Cc3cnn(-c4ccc(F)cc4)c3C=C1CCN(S(=O)(=O)c1ccc(N3CCC3)nc1)C2] | ++ | ++ |
| Example 7 | 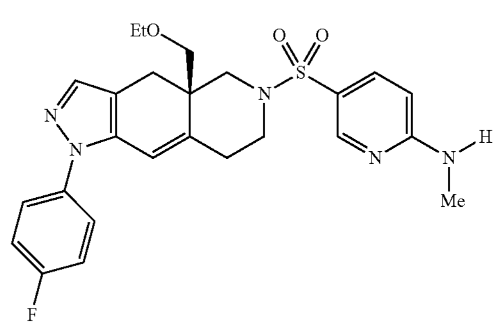 [SMILES: CCOC[C@]12Cc3cnn(-c4ccc(F)cc4)c3C=C1CCN(S(=O)(=O)c1ccc(NC)nc1)C2] | +++ | ++ |

TABLE 1-continued

Activity Data for example compounds of the present invention

| Example No. | Compound Structure | GR Binding $K_i$ | GR Functional $K_i$ |
|---|---|---|---|
| Example 8 | (structure) | +++ | +++ |
| Example 9 | (structure) | + | + |
| Example 10 | (structure) | ++ | ++ |
| Example 11 | (structure) | ++ | ++ |

TABLE 1-continued

Activity Data for example compounds of the present invention

| Example No. | Compound Structure | GR Binding K$_i$ | GR Functional K$_i$ |
|---|---|---|---|
| Example 12 | 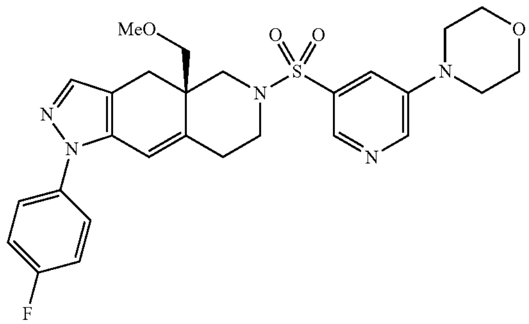 [SMILES: COC[C@]12Cc3cnn(-c4ccc(F)cc4)c3C=C1CCN(S(=O)(=O)c1cncc(N3CCOCC3)c1)C2] | + | + |
| Example 13 | 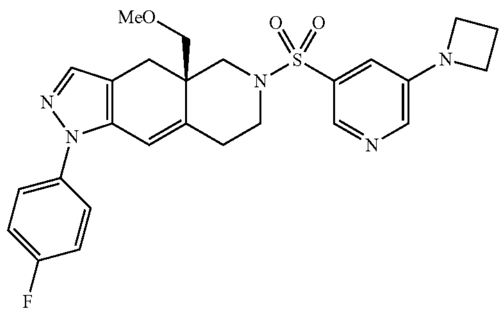 [SMILES: COC[C@]12Cc3cnn(-c4ccc(F)cc4)c3C=C1CCN(S(=O)(=O)c1cncc(N3CCC3)c1)C2] | +++ | ++ |
| Example 14 | 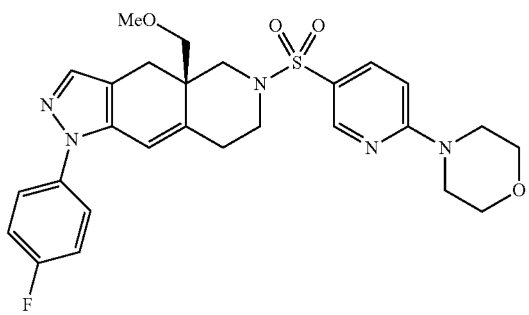 [SMILES: COC[C@]12Cc3cnn(-c4ccc(F)cc4)c3C=C1CCN(S(=O)(=O)c1ccc(N3CCOCC3)nc1)C2] | ++ | ++ |
| Example 15 | 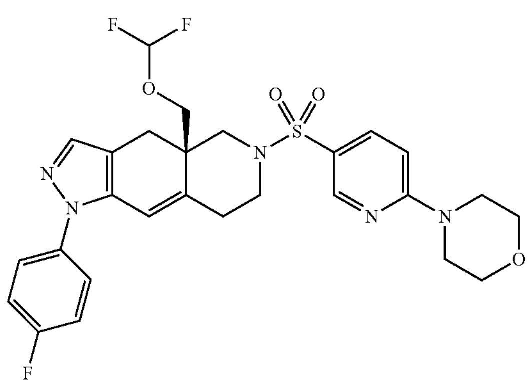 [SMILES: O=S(=O)(c1ccc(N2CCOCC2)nc1)N1CCC2=Cc3c(cnn3-c3ccc(F)cc3)C[C@]2(COC(F)F)C1] | + | ++ |

TABLE 1-continued

Activity Data for example compounds of the present invention

| Example No. | Compound Structure | GR Binding $K_i$ | GR Functional $K_i$ |
|---|---|---|---|
| Example 16 | 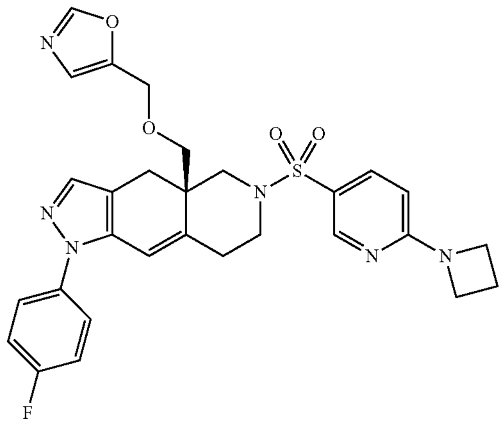 [SMILES: O=S(=O)(c1ccc(N2CCC2)nc1)N1CCC2=Cc3c(cnn3-c3ccc(F)cc3)C[C@]2(COCc2cnco2)C1] | + | ++ |
| Example 17 | 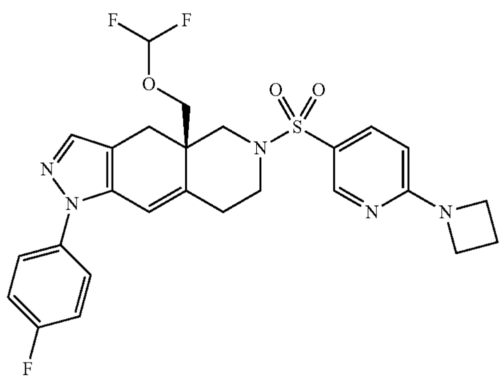 [SMILES: O=S(=O)(c1ccc(N2CCC2)nc1)N1CCC2=Cc3c(cnn3-c3ccc(F)cc3)C[C@]2(COC(F)F)C1] | + | ++ |
| Example 18 | 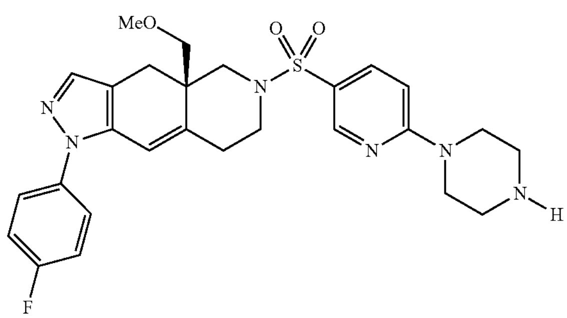 [SMILES: COC[C@]12Cc3cnn(-c4ccc(F)cc4)c3C=C1CCN(S(=O)(=O)c1ccc(N3CCNCC3)nc1)C2] | + | + |
| Example 19 | 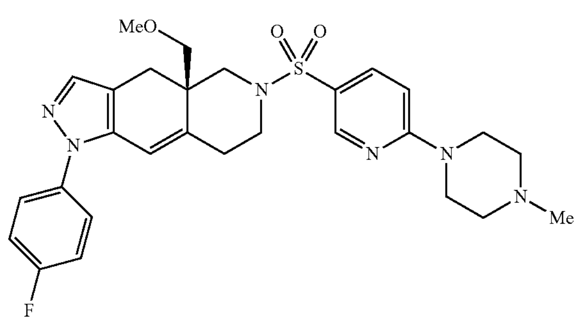 [SMILES: COC[C@]12Cc3cnn(-c4ccc(F)cc4)c3C=C1CCN(S(=O)(=O)c1ccc(N3CCN(C)CC3)nc1)C2] | + | + |

TABLE 1-continued
Activity Data for example compounds of the present invention
| Example No. | Compound Structure | GR Binding $K_i$ | GR Functional $K_i$ |
|---|---|---|---|
| Example 20 | 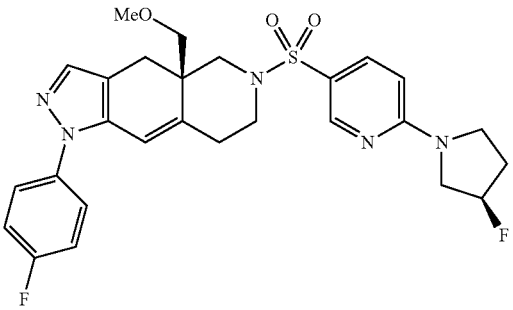 [SMILES: COC[C@]12Cc3cnn(-c4ccc(F)cc4)c3C=C1CCN(S(=O)(=O)c1ccc(N3CC[C@@H](F)C3)nc1)C2] | + | ++ |
| Example 21 | 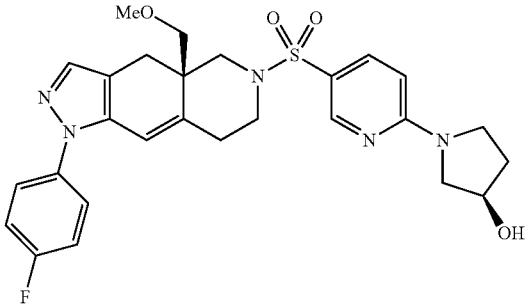 [SMILES: COC[C@]12Cc3cnn(-c4ccc(F)cc4)c3C=C1CCN(S(=O)(=O)c1ccc(N3CC[C@@H](O)C3)nc1)C2] | + | + |
| Example 22 | 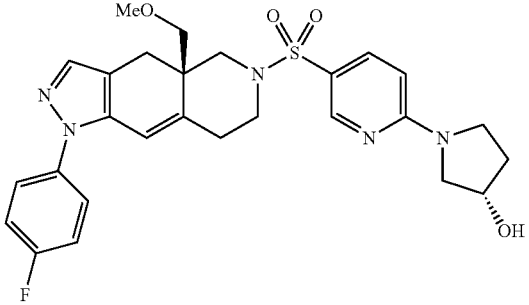 [SMILES: COC[C@]12Cc3cnn(-c4ccc(F)cc4)c3C=C1CCN(S(=O)(=O)c1ccc(N3CC[C@H](O)C3)nc1)C2] | + | + |
| Example 23 | 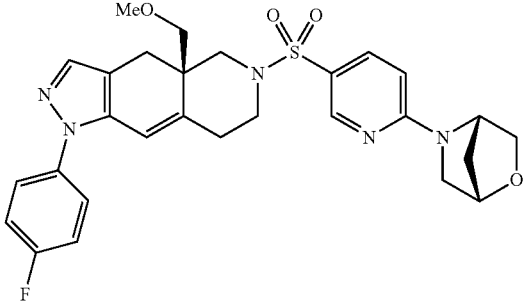 [SMILES: COC[C@]12Cc3cnn(-c4ccc(F)cc4)c3C=C1CCN(S(=O)(=O)c1ccc(N3C[C@@H]4C[C@H]3CO4)nc1)C2] | + | + |

TABLE 1-continued
Activity Data for example compounds of the present invention
| Example No. | Compound Structure | GR Binding $K_i$ | GR Functional $K_i$ |
|---|---|---|---|
| Example 24 | 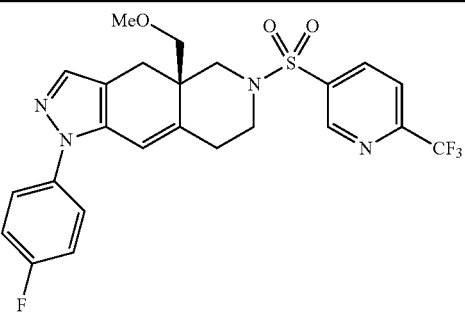 | + | ++ |
| Example 25 | 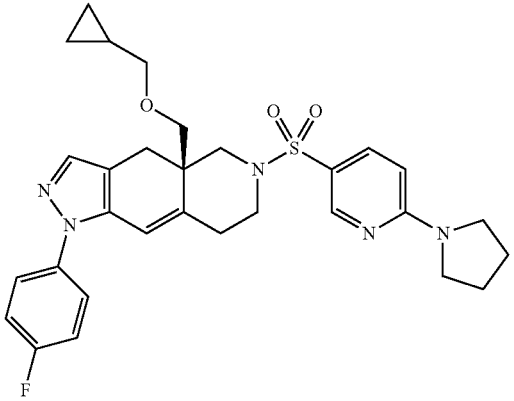 [SMILES: O=S(=O)(c1ccc(N2CCCC2)nc1)N1CCC2=Cc3c(cnn3-c3ccc(F)cc3)C[C@]2(COCC2CC2)C1] | ++ | +++ |
| Example 26 | 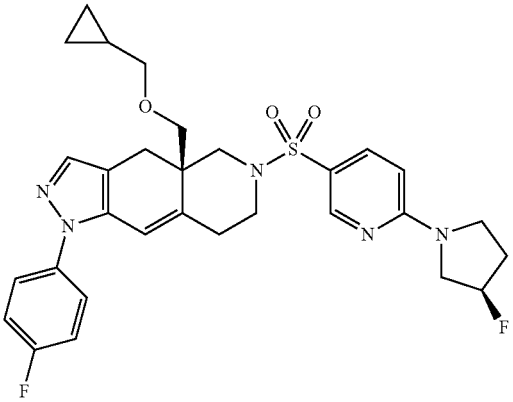 [SMILES: O=S(=O)(c1ccc(N2CC[C@@H](F)C2)nc1)N1CCC2=Cc3c(cnn3-c3ccc(F)cc3)C[C@]2(COCC2CC2)C1] | ++ | +++ |
| Example 27 | 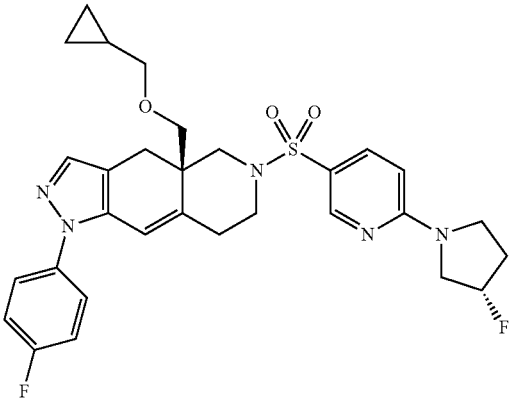 [SMILES: O=S(=O)(c1ccc(N2CC[C@H](F)C2)nc1)N1CCC2=Cc3c(cnn3-c3ccc(F)cc3)C[C@]2(COCC2CC2)C1] | ++ | +++ |

TABLE 1-continued
Activity Data for example compounds of the present invention
| Example No. | Compound Structure | GR Binding $K_i$ | GR Functional $K_i$ |
|---|---|---|---|
| Example 28 | 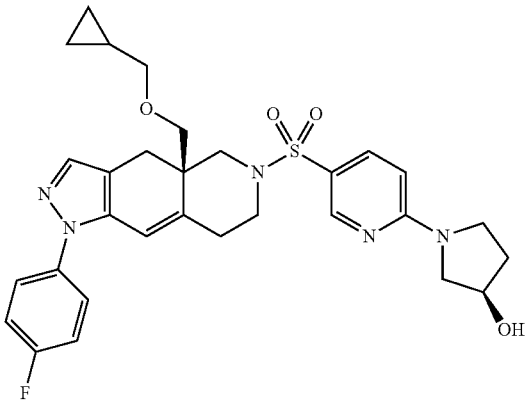 [SMILES: O=S(=O)(c1ccc(N2CC[C@@H](O)C2)nc1)N1CCC2=Cc3c(cnn3-c3ccc(F)cc3)C[C@]2(COCC2CC2)C1] | +++ | ++ |
| Example 29 | 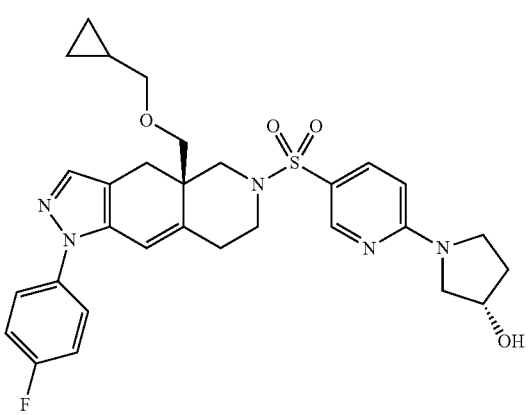 [SMILES: O=S(=O)(c1ccc(N2CC[C@H](O)C2)nc1)N1CCC2=Cc3c(cnn3-c3ccc(F)cc3)C[C@]2(COCC2CC2)C1] | ++ | ++ |
| Example 30 | 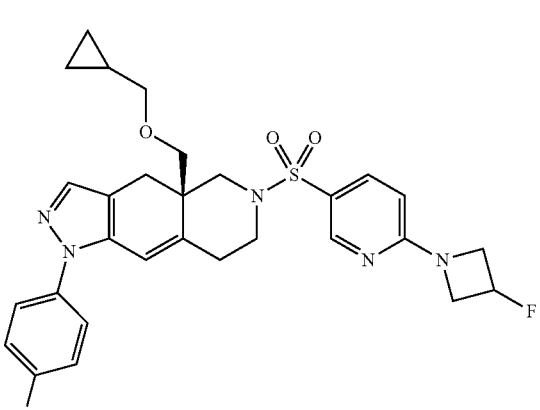 | +++ | +++ |

TABLE 1-continued

Activity Data for example compounds of the present invention

| Example No. | Compound Structure | GR Binding K$_i$ | GR Functional K$_i$ |
|---|---|---|---|
| Example 31 | 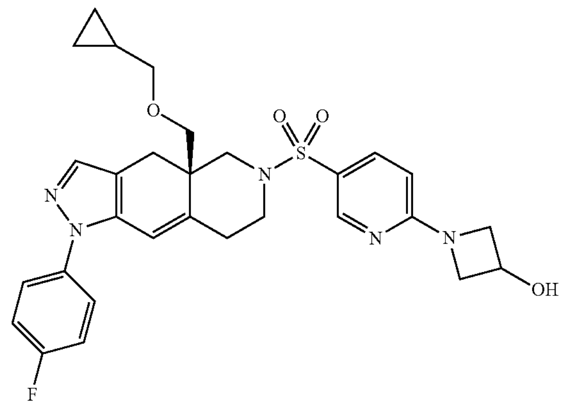 [SMILES: O=S(=O)(c1ccc(N2CC(O)C2)nc1)N1CCC2=Cc3c(cnn3-c3ccc(F)cc3)C[C@]2(COCC2CC2)C1] | ++ | ++ |
| Example 32 | 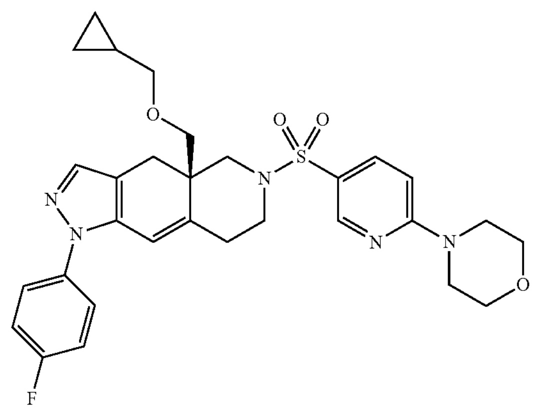 [SMILES: O=S(=O)(c1ccc(N2CCOCC2)nc1)N1CCC2=Cc3c(cnn3-c3ccc(F)cc3)C[C@]2(COCC2CC2)C1] | ++ | +++ |
| Example 33 | 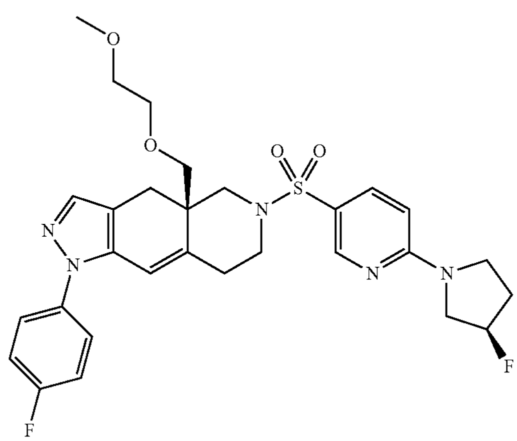 [SMILES: COCCOC[C@]12Cc3cnn(-c4ccc(F)cc4)c3C=C1CCN(S(=O)(=O)c1ccc(N3CC[C@@H](F)C3)nc1)C2] | ++ | +++ |

TABLE 1-continued

Activity Data for example compounds of the present invention

| Example No. | Compound Structure | GR Binding $K_i$ | GR Functional $K_i$ |
|---|---|---|---|
| Example 34 | 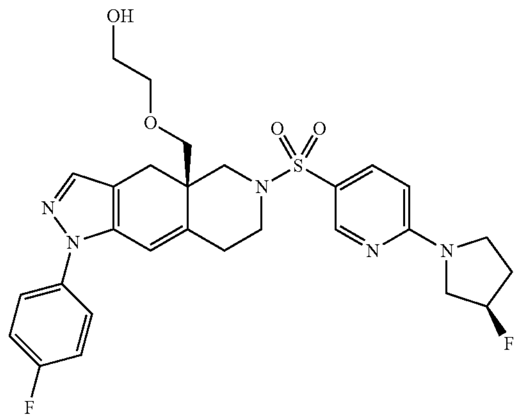 [SMILES: O=S(=O)(c1ccc(N2CC[C@@H](F)C2)nc1)N1CCC2=Cc3c(cnn3-c3ccc(F)cc3)C[C@]2(COCCO)C1] | + | + |
| Example 35 | 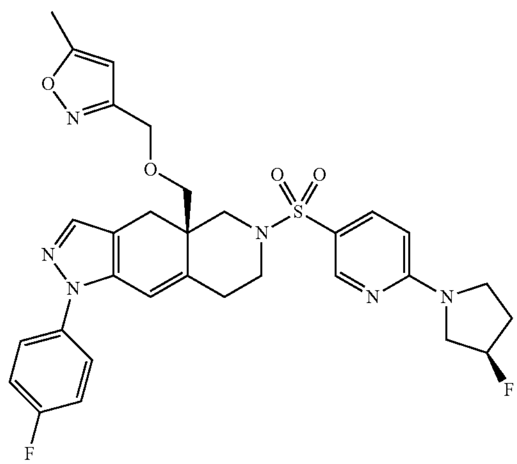 [SMILES: Cc1cc(COC[C@]23Cc4cnn(-c5ccc(F)cc5)c4C=C2CCN(S(=O)(=O)c2ccc(N4CC[C@@H](F)C4)nc2)C3)no1] | + | ++ |
| Example 36 | 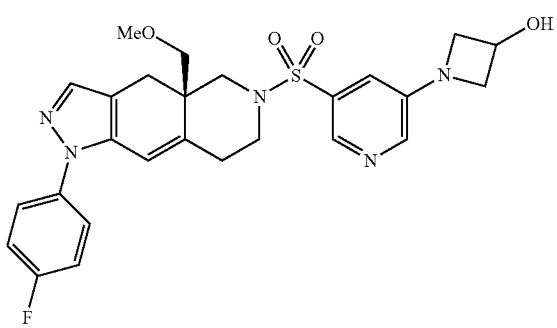 [SMILES: COC[C@]12Cc3cnn(-c4ccc(F)cc4)c3C=C1CCN(S(=O)(=O)c1cncc(N3CC(O)C3)c1)C2] | ++ | + |
| Example 37 | 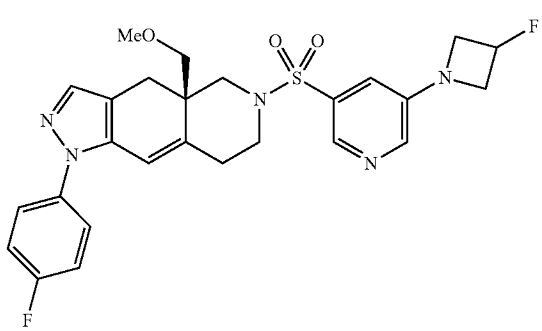 [SMILES: COC[C@]12Cc3cnn(-c4ccc(F)cc4)c3C=C1CCN(S(=O)(=O)c1cncc(N3CC(F)C3)c1)C2] | ++ | +++ |

TABLE 1-continued

Activity Data for example compounds of the present invention

| Example No. | Compound Structure | GR Binding $K_i$ | GR Functional $K_i$ |
|---|---|---|---|
| Example 38 | 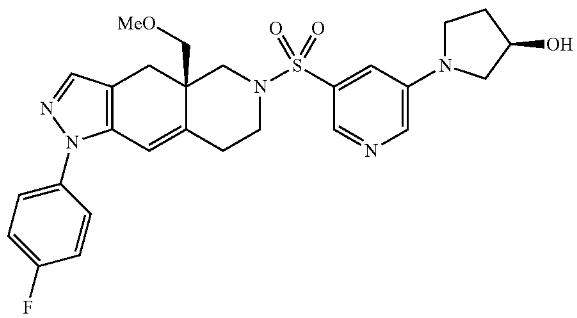 [SMILES: COC[C@]12Cc3cnn(-c4ccc(F)cc4)c3C=C1CCN(S(=O)(=O)c1cncc(N3CC[C@@H](O)C3)c1)C2] | ++ | ++ |
| Example 39 | 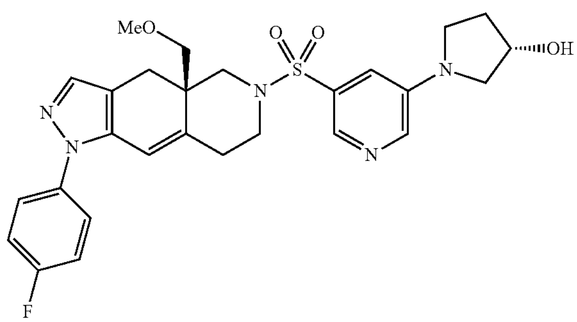 [SMILES: COC[C@]12Cc3cnn(-c4ccc(F)cc4)c3C=C1CCN(S(=O)(=O)c1cncc(N3CC[C@H](O)C3)c1)C2] | ++ | + |
| Example 40 | 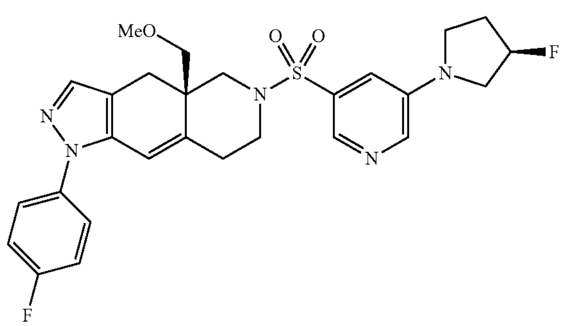 [SMILES: COC[C@]12Cc3cnn(-c4ccc(F)cc4)c3C=C1CCN(S(=O)(=O)c1cncc(N3CC[C@@H](F)C3)c1)C2] | + | +++ |
| Example 41 | 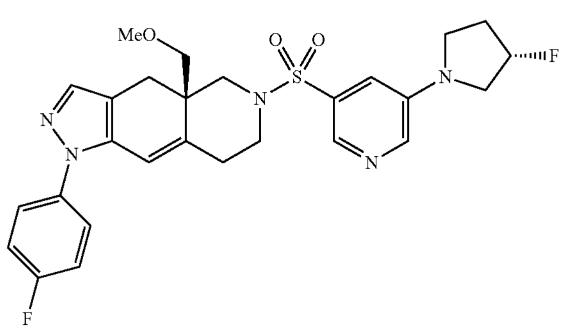 [SMILES: COC[C@]12Cc3cnn(-c4ccc(F)cc4)c3C=C1CCN(S(=O)(=O)c1cncc(N3CC[C@H](F)C3)c1)C2] | ++ | +++ |

TABLE 1-continued
Activity Data for example compounds of the present invention
| Example No. | Compound Structure | GR Binding $K_i$ | GR Functional $K_i$ |
|---|---|---|---|
| Example 42 | 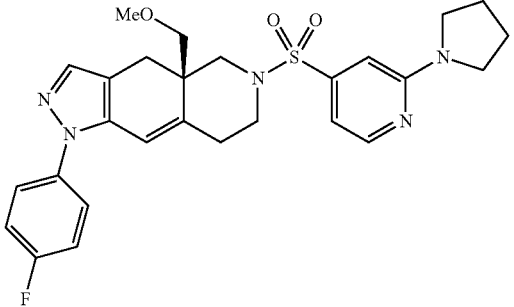 [SMILES: COC[C@]12Cc3cnn(-c4ccc(F)cc4)c3C=C1CCN(S(=O)(=O)c1ccnc(N3CCCC3)c1)C2] | + | +++ |
| Example 43 | 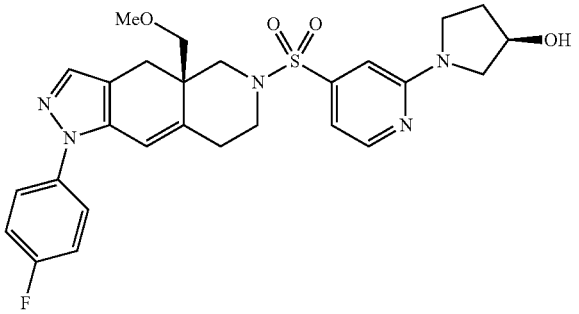 [SMILES: COC[C@]12Cc3cnn(-c4ccc(F)cc4)c3C=C1CCN(S(=O)(=O)c1ccnc(N3CC[C@@H](O)C3)c1)C2] | + | + |
| Example 44 | 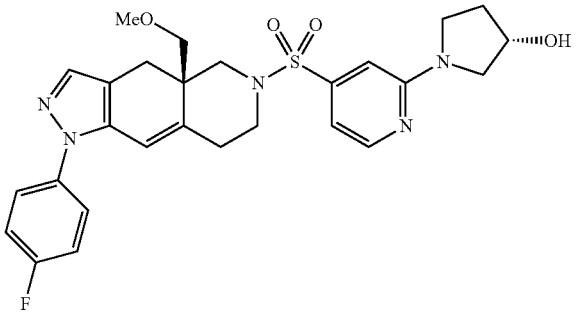 [SMILES: COC[C@]12Cc3cnn(-c4ccc(F)cc4)c3C=C1CCN(S(=O)(=O)c1ccnc(N3CC[C@H](O)C3)c1)C2] | + | + |
| Example 45 | 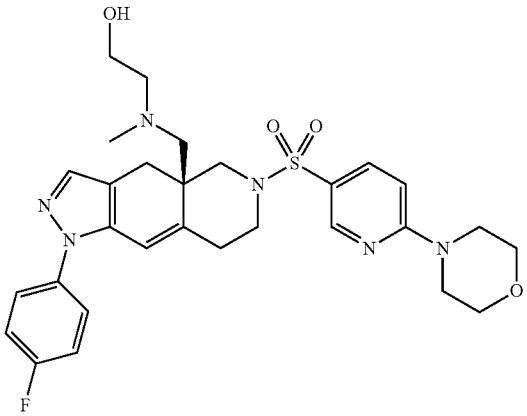 [SMILES: CN(CCO)C[C@]12Cc3cnn(-c4ccc(F)cc4)c3C=C1CCN(S(=O)(=O)c1ccc(N3CCOCC3)nc1)C2] | + | ++ |

TABLE 1-continued
Activity Data for example compounds of the present invention
| Example No. | Compound Structure | GR Binding $K_i$ | GR Functional $K_i$ |
|---|---|---|---|
| Example 46 | 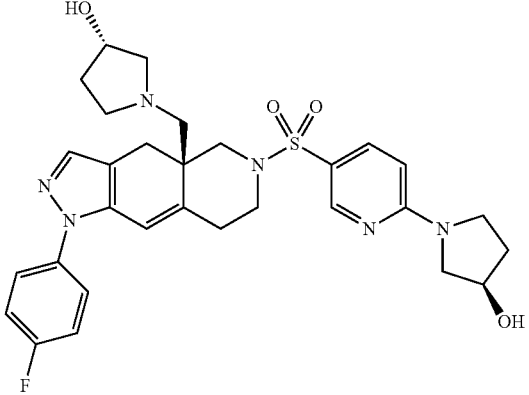 [SMILES: O=S(=O)(c1ccc(N2CC[C@@H](O)C2)nc1)N1CCC2=Cc3c(cnn3-c3ccc(F)cc3)C[C@]2(CN2CC[C@H](O)C2)C1] | + | nt |
| Example 47 | 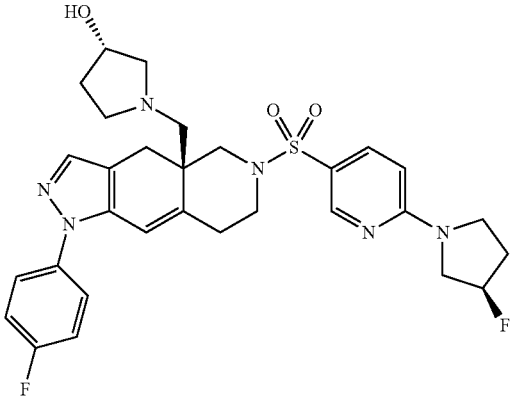 [SMILES: O=S(=O)(c1ccc(N2CC[C@@H](F)C2)nc1)N1CCC2=Cc3c(cnn3-c3ccc(F)cc3)C[C@]2(CN2CC[C@H](O)C2)C1] | + | + |
| Example 48 | 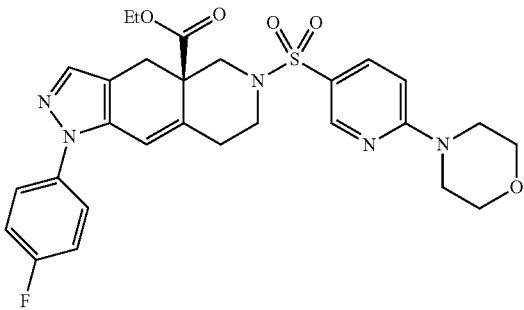 [SMILES: CCOC(=O)[C@]12Cc3cnn(-c4ccc(F)cc4)c3C=C1CCN(S(=O)(=O)c1ccc(N3CCOCC3)nc1)C2] | ++ | ++ |
| Example 49 | 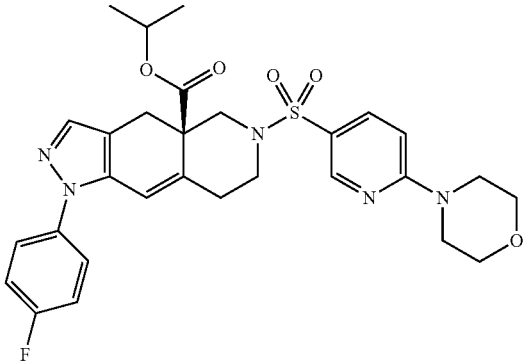 [SMILES: CC(C)OC(=O)[C@]12Cc3cnn(-c4ccc(F)cc4)c3C=C1CCN(S(=O)(=O)c1ccc(N3CCOCC3)nc1)C2] | +++ | ++ |

TABLE 1-continued

Activity Data for example compounds of the present invention

| Example No. | Compound Structure | GR Binding K$_i$ | GR Functional K$_i$ |
|---|---|---|---|
| Example 50 | 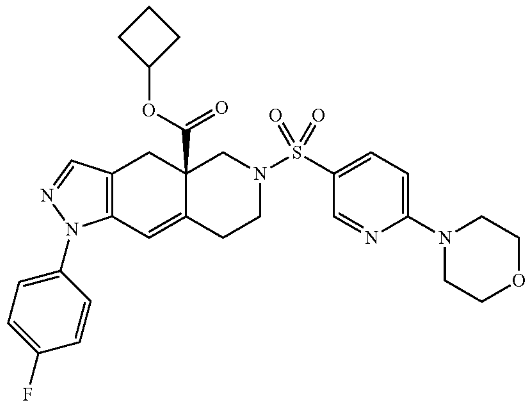 [SMILES: O=C(OC1CCC1)[C@]12Cc3cnn(-c4ccc(F)cc4)c3C=C1CCN(S(=O)(=O)c1ccc(N3CCOCC3)nc1)C2] | ++ | +++ |
| Example 51 | 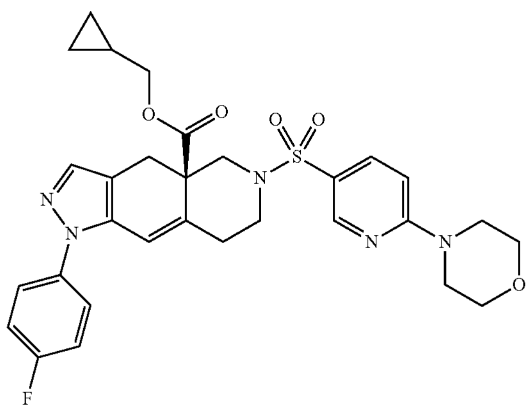 [SMILES: O=C(OCC1CC1)[C@]12Cc3cnn(-c4ccc(F)cc4)c3C=C1CCN(S(=O)(=O)c1ccc(N3CCOCC3)nc1)C2] | ++ | +++ |
| Example 52 | 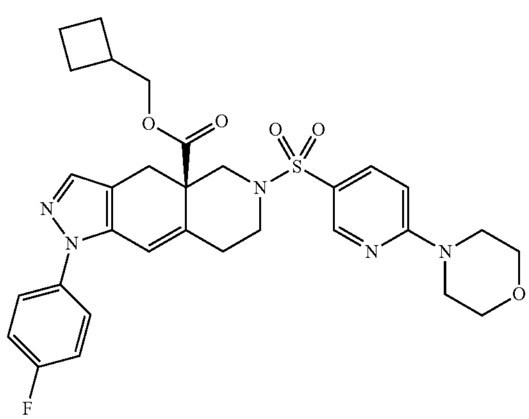 [SMILES: O=C(OCC1CCC1)[C@]12Cc3cnn(-c4ccc(F)cc4)c3C=C1CCN(S(=O)(=O)c1ccc(N3CCOCC3)nc1)C2] | ++ | +++ |

TABLE 1-continued

Activity Data for example compounds of the present invention

| Example No. | Compound Structure | GR Binding $K_i$ | GR Functional $K_i$ |
|---|---|---|---|
| Example 53 | 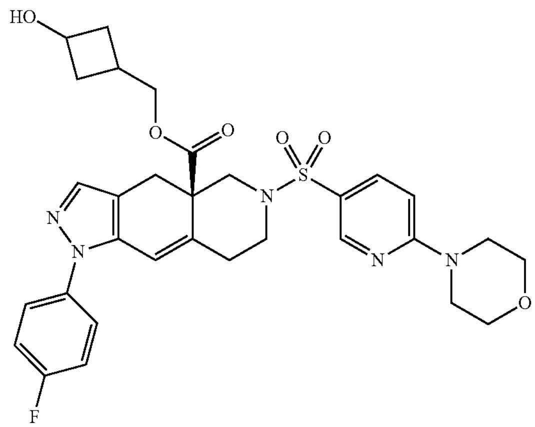 [SMILES: O=C(OCC1CC(O)C1)[C@]12Cc3cnn(-c4ccc(F)cc4)c3C=C1CCN(S(=O)(=O)c1ccc(N3CCOCC3)nc1)C2] | + | ++ |
| Example 54 | 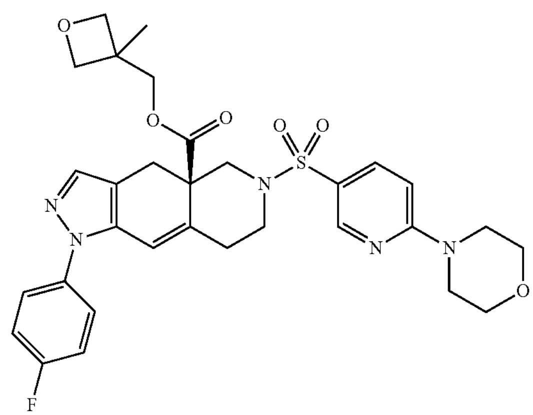 [SMILES: CC1(COC(=O)[C@]23Cc4cnn(-c5ccc(F)cc5)c4C=C2CCN(S(=O)(=O)c2ccc(N4CCOCC4)nc2)C3)COC1] | + | + |
| Example 55 | 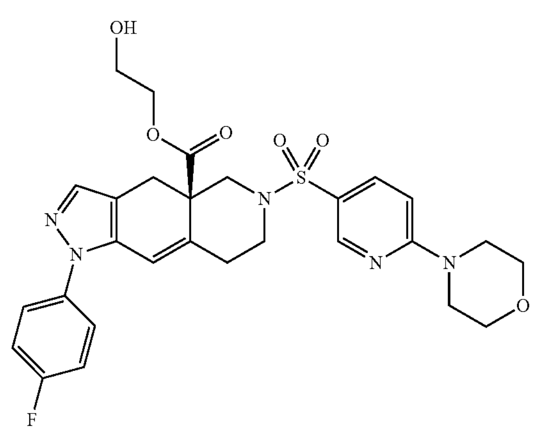 [SMILES: O=C(OCCO)[C@]12Cc3cnn(-c4ccc(F)cc4)c3C=C1CCN(S(=O)(=O)c1ccc(N3CCOCC3)nc1)C2] | + | + |

TABLE 1-continued
Activity Data for example compounds of the present invention
| Example No. | Compound Structure | GR Binding $K_i$ | GR Functional $K_i$ |
|---|---|---|---|
| Example 56 | 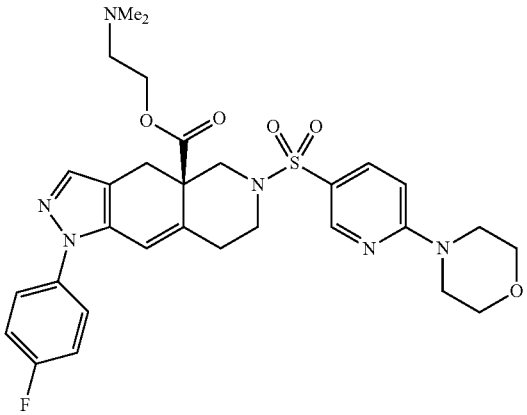 [SMILES: CN(C)CCOC(=O)[C@]12Cc3cnn(-c4ccc(F)cc4)c3C=C1CCN(S(=O)(=O)c1ccc(N3CCOCC3)nc1)C2] | + | + |
| Example 57 | 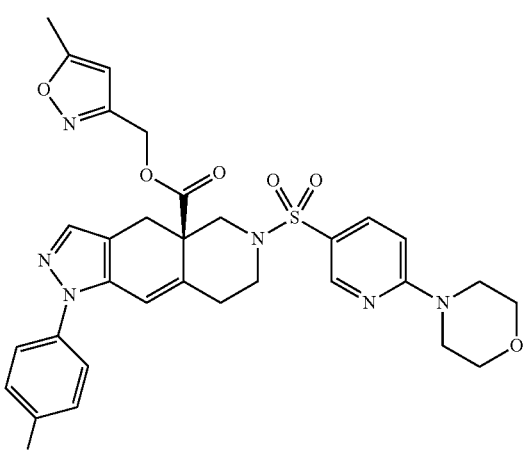 | ++ | ++ |
| Example 58 | 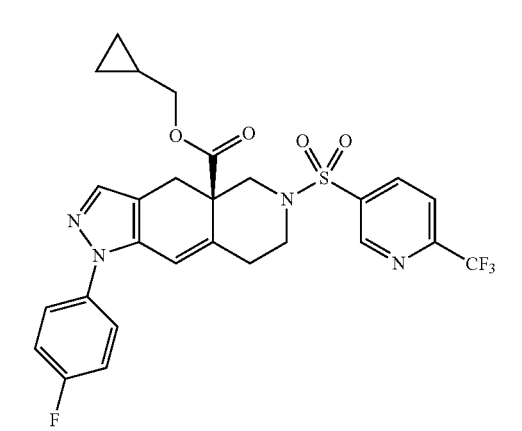 [SMILES: O=C(OCC1CC1)[C@]12Cc3cnn(-c4ccc(F)cc4)c3C=C1CCN(S(=O)(=O)c1ccc(C(F)(F)F)nc1)C2] | ++ | +++ |

TABLE 1-continued

Activity Data for example compounds of the present invention

| Example No. | Compound Structure | GR Binding K$_i$ | GR Functional K$_i$ |
|---|---|---|---|
| Example 59 | 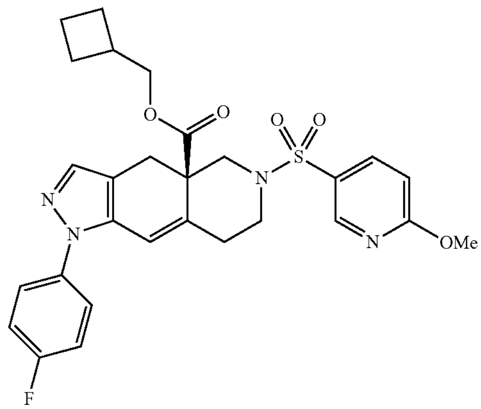 [SMILES: COc1ccc(S(=O)(=O)N2CCC3=Cc4c(cnn4-c4ccc(F)cc4)C[C@]3(C(=O)OCC3CCC3)C2)cn1] | ++ | +++ |
| Example 60 | 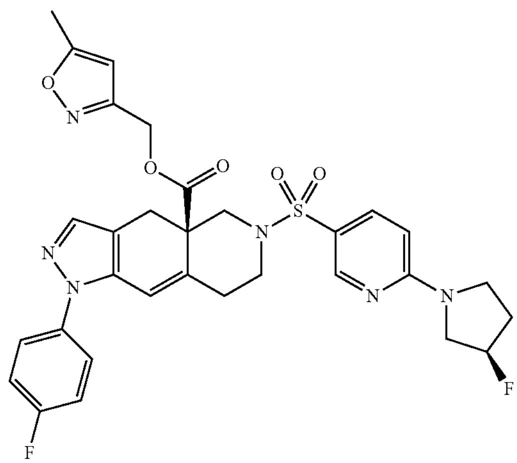 [SMILES: Cc1cc(COC(=O)[C@]23Cc4cnn(-c5ccc(F)cc5)c4C=C2CCN(S(=O)(=O)c2ccc(N4CC[C@@H](F)C4)nc2)C3)no1] | ++ | ++ |
| Example 61 | 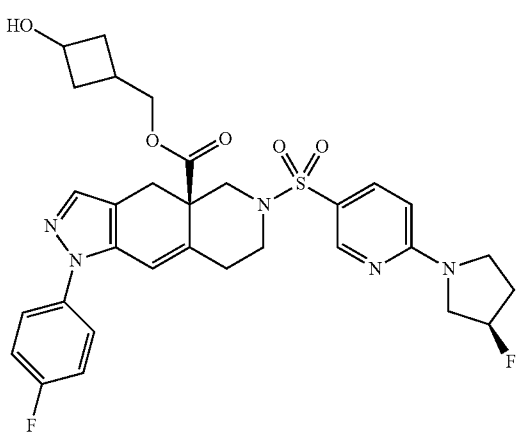 [SMILES: O=C(OCC1CC(O)C1)[C@]12Cc3cnn(-c4ccc(F)cc4)c3C=C1CCN(S(=O)(=O)c1ccc(N3CC[C@@H](F)C3)nc1)C2] | + | ++ |

TABLE 1-continued

Activity Data for example compounds of the present invention

| Example No. | Compound Structure | GR Binding $K_i$ | GR Functional $K_i$ |
|---|---|---|---|
| Example 62 | (structure) | + | + |
| Example 63 | (structure) | + | ++ |
| Example 64 | (structure) | ++ | +++ |

In Table 1, GR Binding compounds with a $K_i$ value of less than 0.5 nM are designated with +++; compounds with a $K_i$ value between 0.5 nM and 1.0 nM are designated with ++; and compounds with a $K_i$ value greater than 1.0 nM are designated with +. GR Functional compounds with a $K_i$ value of less than 10 nM are designated with +++, compounds with a $K_i$ value between 10 nM and 50 nM are designated with ++; and compounds with a $K_i$ value greater than 50 nM are designated with +.

VIII. Examples $^1$H NMR spectra were recorded at ambient temperature using a Varian Unity Inova spectrometer (400 MHz) with a 5 mm inverse detection triple resonance probe for detection of $^1$H, $^{13}$C and $^{31}$P or a Bruker Avance DRX spectrometer (400 MHz) with a 5 mm inverse detection triple resonance TXI probe.

Mass Spectrometry (LCMS) experiments to determine retention times and associated mass ions were performed using the following methods:

Method A: experiments were performed using Waters Quattro Micro triple quadrupole mass spectrometer with positive and negative ion electrospray and ELS/Diode array detection using a Higgins Clipeus 5 micron C18 100×3.0 mm column and a 1 mL/minute flow rate. The initial solvent system was 85% water containing 0.1% formic acid (solvent A) and 15% methanol containing 0.1% formic acid (solvent B) for the first minute followed by a gradient up to 5% solvent A and 95% solvent B over the next 12 minutes. The final solvent system was held constant for a further 7 minutes.

Method B: experiments were performed using a Waters Platform LC quadrupole mass spectrometer with positive and negative ion electrospray and ELS/Diode array detection using a Phenomenex Luna 3 micron C18 (2) 30×4.6 mm column and a 2 mL/minute flow rate. The solvent system was 95% water containing 0.1% formic acid (solvent A) and 5% acetonitrile containing 0.1% formic acid (solvent B) for the first 50 seconds followed by a gradient up to 5% solvent A and 95% solvent B over the next 4 minutes. The final solvent system was held constant for a further 1 minute.

Method C: experiments were performed using Waters Micromass ZQ2000 quadrupole mass spectrometer with positive and negative ion electrospray and ELS/Diode array detection using a Higgins Clipeus 5 micron C18 100×3.0 mm column and a 1 mL/minute flow rate. The initial solvent system was 95% water containing 0.1% formic acid (solvent A) and 5% acetonitrile containing 0.1% formic acid (solvent B) for the first minute followed by a gradient up to 5% solvent A and 95% solvent B over the next 14 minutes. The final solvent system was held constant for a further 5 minutes.

Method D: experiments were performed using a Waters ZMD quadrupole mass spectrometer with positive and negative ion electrospray and ELS/Diode array detection using a Luna 3 micron C18 (2) 30×4.6 mm column and a 2 mL/minute flow rate. The initial solvent system was 95% water containing 0.1% formic acid (solvent A) and 5% acetonitrile containing 0.1% formic acid (solvent B) for the first 50 seconds followed by a gradient up to 5% solvent A and 95% solvent B over the next 4 minutes. The final solvent system was held constant for a further 1 minute.

Method E: experiments were performed using a Finnigan AQA single quadrupole mass spectrometer with positive ion electrospray and ELS/Diode array detection using a Luna 3 micron C18 (2) 30×4.6 mm column and a 2 mL/minute flow rate. The initial solvent system was 95% water containing 0.1% formic acid (solvent A) and 5% acetonitrile containing 0.1% formic acid (solvent B) for the first 50 seconds followed by a gradient up to 5% solvent A and 95% solvent B over the next 4 minutes. The final solvent system was held constant for a further 1 minute.

Method F: experiments were performed using a Waters ZQ mass spectrometer with positive and negative ion electrospray and diode array detection using an Acquity HPLC BEH C18 100×2.1 mm column and a 0.4 ml/minute flow rate. The initial solvent system was 95% water containing 0.1% formic acid (solvent A) and 5% acetonitrile containing 0.1% formic acid (solvent B) for the first 0.4 min followed by a gradient up to 5% solvent A and 95% solvent B over the next 5.6 minutes. The final solvent system was held constant for a further 0.8 minutes.

Method G: experiments were performed using a Waters ZMD mass spectrometer with positive and negative ion electrospray and diode array detection using a Phenomenex Luna C18 (2) 3μ, 30×4.6 mm at 2.0 ml/minute flow rate. The initial solvent system was 95% water containing 0.1% formic acid (solvent A) and 5% acetonitrile containing 0.1% formic acid (solvent B) for the first 0.5 min followed by a gradient up to 5% solvent A and 95% solvent B over the next 4.0 minutes. The final solvent system was held constant for a further 1.0 minute.

Example 1

(R)-4a-Ethoxymethyl-1-(4-fluorophenyl)-6-[[6-(4-morpholinyl)-3-pyridinyl]sulfonyl]-1,4,7,8-tetrahydro-1,2,6-triazacyclopenta[b]naphthalene

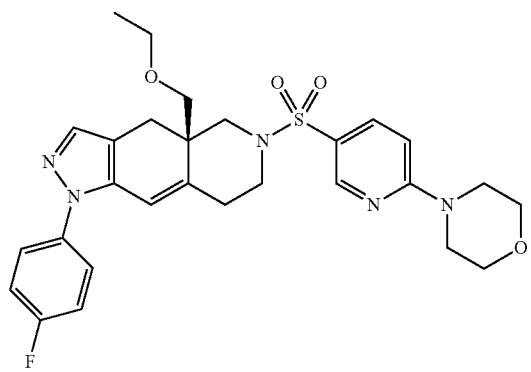 [SMILES: CCOC[C@]12Cc3cnn(-c4ccc(F)cc4)c3C=C1CCN(S(=O)(=O)c1ccc(N3CCOCC3)nc1)C2]

Preparation 1a. (R)-7-[1-Hydroxymeth-(Z)-ylidene]-6-oxo-4,6,7,8-tetrahydro-3H-isoquinoline-2,8a-dicarboxylic acid 2-tert-butyl ester 8a-methyl ester A solution of diisopropylamine (4.0 mL) in diethyl ether (70 mL) under nitrogen at −40° C. was treated with a 1.6 M solution of n-butyllithium (16 mL), and the resulting solution was cooled to −78° C. and treated with a solution of (R)-6-oxo-2,3,4,6,7,8-hexahydro-1H-naphthalene-2,8a-dicarboxylic acid 2-tert-butyl ester 8a-methyl ester (5.0 g) in diethyl ether (25 mL). The resulting solution was stirred at −78° C. for 15 minutes and treated with trifluoroethyl formate (6.0 mL). After a further 1.5 hours at −78° C., the solution was diluted with 2.0 M aqueous hydrochloric acid solution (20 mL). The phases were separated, and the organic phase was washed with water and extracted with an aqueous potassium carbonate solution. The aqueous potassium carbonate phase was acidified with 1.0 M aqueous hydrochloric acid solution and extracted with diethyl ether. The organic phase was dried over sodium sulfate and concentrated under reduced pressure to afford the title compound as an orange oil (3.8 g). $^1$H NMR (CDCl$_3$): δ 13.84-13.52 (bs, 1H), 7.58-7.51 (s, 1H), 6.09-6.06 (s, 1H), 4.69-4.59 (d, 1H, J=13 Hz), 4.41-4.05 (m, 1H), 3.67 (s, 3H), 2.95-2.66 (m, 4H), 2.49-2.34 (m, 2H), 1.45 (s, 9H).

Preparation 1b. (R)-1-(4-Fluorophenyl)-1,4,7,8-tetrahydro-1,2,6-triazacyclopenta[b]naph-thalene-4a,6-dicarboxylic acid 6-tert-butyl ester 4a-methyl ester A mixture of (R)-7-[1-hydroxymeth-(Z)-ylidene]-6-oxo-4,6,7,8-tetrahydro-3H-isoquinoline-2,8a-dicarboxylic acid 2-tert-butyl ester 8a-methyl ester (3.8 g), 4-fluorophenylhydrazine hydrochloride (2.7 g), sodium acetate (1.4 g) and acetic acid (30 mL) was stirred at room temperature for 1 hour. The mixture was concentrated under reduced pressure, and the residue was partitioned between diethyl ether and 2.0

M aqueous hydrochloric acid solution. The organic phase was washed with water, aqueous potassium carbonate solution and brine, and then dried over sodium sulfate. The solvent was removed under reduced pressure, and the residue was triturated with a mixture of cyclohexane and diethyl ether to afford the title compound as a yellow solid (3.7 g). $^1$H NMR (CDCl$_3$): δ 7.48-7.39 (m, 3H), 7.21-7.12 (m, 2H), 6.45-6.41 (s, 1H), 4.69-4.55 (d, 1H, J=13 Hz), 4.32-3.98 (m, 1H), 3.64 (s, 3H), 3.51-3.33 (m, 1H), 3.00-2.71 (m, 3H), 2.59-2.51 (d, 1H, J=16 Hz), 2.48-2.34 (m, 1H), 1.46 (s, 9H).

Preparation 1c. (R)-1-(4-Fluorophenyl)-6-(6-morpholin-4-ylpyridine-3-sulfonyl)-1,4,5,6,7,8-hexahydro-1,2,6-triazacyclopenta[b]naphthalene-4a-carboxylic acid methyl ester A solution of (R)-1-(4-fluorophenyl)-1,4,7,8-tetrahydro-1,2,6-triazacyclopenta[b]naphthalene-4a,6-dicarboxylic acid 6-tert-butyl ester 4a-methyl ester (16 g) in methanol (50 mL) was treated with a 4.0 M solution of hydrochloric acid in dioxane (50 mL), and the resulting solution was stirred at room temperature for 1 hour. The solution was concentrated under reduced pressure, and the residue was suspended in dichloromethane, cooled to 0° C. and treated sequentially with N,N-diisopropylethylamine (33 mL) and 6-morpholin-4-yl-pyridine-3-sulfonyl chloride (10 g). The resulting solution was stirred at room temperature for 1 hour, concentrated under reduced pressure and the residue partitioned between diethyl ether and 2.0 M aqueous hydrochloric acid solution. The organic phase was washed with saturated aqueous potassium carbonate solution, water and brine, and then dried over sodium sulfate. The solvent was removed under reduced pressure, and the residue was triturated to afford the title compound as a cream solid (15 g). The triturition liquors were purified by column chromatography on silica gel, eluting with a mixture of dichloromethane and diethyl ether (1:20 to 1:10 by volume), to afford the title compound (2.6 g). $^1$H NMR (CDCl$_3$): δ 8.54-8.51 (d, 1H, J=2.6 Hz), 7.79-7.74 (dd, 1H, J=9.0, 2.5 Hz), 7.45-7.39 (m, 2H), 7.38-7.37 (s, 1H), 7.19-7.13 (m, 2H), 6.64-6.59 (d, 1H, J=9.2 Hz), 6.43-6.39 (s, 1H), 4.38-4.32 (dd, 1H, J=11, 1.9 Hz), 3.89-3.83 (m, 1H), 3.82-3.77 (m, 4H), 3.71 (s, 3H), 3.68-3.63 (m, 4H), 3.33-3.26 (d, 1H, J=16 Hz), 2.96-2.84 (m, 1H), 2.62-2.54 (d, 1H, J=16 Hz), 2.51-2.37 (m, 3H).

Preparation 1d. [(R)-1-(4-Fluorophenyl)-6-[[6-(4-morpholinyl)-3-pyridinyl]sulfonyl]-1,4,7,8-tetrahydro-1,2,6-triazacyclopenta[b]naphthalen-4a-yl]methanol A solution of (R)-1-(4-fluorophenyl)-6-(6-morpholin-4-ylpyridine-3-sulfonyl)-1,4,5,6,7,8-hexahydro-1,2,6-triazacyclopenta[b]naphthalene-4a-carboxylic acid methyl ester (17 g) in dichloromethane (300 mL) under nitrogen at −78° C. was treated with a 1.0 M solution of diisobutylaluminium hydride in toluene (123 mL). After 1 hour at −78° C., the solution was diluted with water and the phases separated. The organic phase was dried over sodium sulfate and concentrated under reduced pressure. The residue was triturated with diethyl ether to afford the title compound as a white solid (16.7 g). $^1$H NMR (CDCl$_3$): δ 8.56-8.53 (d, 1H, J=2.4 Hz), 7.81-7.77 (dd, 1H, J=9.0, 2.4 Hz), 7.44-7.38 (m, 3H), 7.19-7.12 (m, 3H), 6.65-6.60 (d, 1H, J=9.0 Hz), 6.31-6.28 (d, 1H, J=2.5 Hz), 4.08-4.03 (dd, 1H, J=12, 2.4 Hz), 3.99-3.92 (m, 1H), 3.84-3.79 (m, 4H), 3.69-3.64 (m, 4H), 3.37-3.30 (m, 1H), 3.14-3.08 (d, 1H, J=16 Hz), 2.82-2.70 (m, 1H), 2.58-2.48 (m, 1H), 2.42-3.34 (m, 1H), 2.28-2.16 (m, 3H).

Preparation 1e. (R)-4a-Ethoxymethyl-1-(4-fluorophenyl)-6-[[6-(4-morpholinyl)-3-pyridinyl]-sulfonyl]-1,4,7,8-tetrahydro-1,2,6-triazacyclopenta[b]naphthalene A suspension of sodium hydride (1.5 g) in tetrahydrofuran (20 mL) at room temperature was treated sequentially with a solution of [(R)-1-(4-fluorophenyl)-6-[[6-(4-morpholinyl)-3-pyridinyl]sulfonyl]-1,4,7,8-tetrahydro-1,2,6-triaza-cyclopent-a[b]naphthalen-4a-yl]methanol (8.0 g) in tetrahydrofuran (60 mL) and iodoethane (3.7 mL), and the resulting mixture was stirred at 50° C. for 1 hour. The mixture was cooled to room temperature and partitioned between ethyl acetate and 1.0 M aqueous hydrochloric acid solution. The aqueous phase was extracted with ethyl acetate, and the combined organic phase was washed with aqueous sodium thiosulfate solution, aqueous potassium carbonate solution, water and brine, and then dried over sodium sulfate. The solvent was removed under reduced pressure, and the residue was purified by column chromatography on silica gel, eluting with a mixture of dichloromethane and diethyl ether (1:20 to 1:10 by volume), to afford a cream foam (7.5 g). The cream foam was crystallized from industrial methylated spirits to afford the title compound as a white solid (6.3 g). LCMS (Method A): 552 (M+H)$^+$, Retention time 5.0 minutes. $^1$H NMR (CDCl$_3$): δ 8.53-8.49 (d, 1H, J=2.4 Hz), 7.79-7.73 (dd, 1H, J=9.2, 2.5 Hz), 7.41-7.33 (m, 3H), 7.15-7.07 (t, 2H, J=8.0 Hz), 6.62-6.55 (d, 1H, J=9.0 Hz), 6.25-6.21 (d, 1H, J=2.3 Hz), 4.15-4.08 (dd, 1H, J=12, 2.3 Hz), 3.89-3.80 (m, 1H), 3.80-3.73 (m, 4H), 3.67-3.59 (m, 4H), 3.52-3.35 (m, 3H), 3.14-3.02 (m, 2H), 2.74-2.61 (m, 1H), 2.41-2.29 (m, 2H), 2.20-2.04 (dd, 2H, J=34, 16 Hz), 1.19-1.11 (t, 3H, J=7.0 Hz).

Example 2

(R)-4a-Ethoxymethyl-1-(4-fluorophenyl)-6-[[3-pyridinyl]sulfonyl]-1,4,7,8-tetrahydro-1,2,6-triazacyclopenta[b]naphthalene

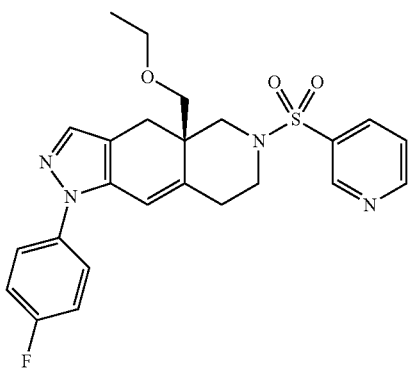 [SMILES: CCOC[C@]12Cc3cnn(-c4ccc(F)cc4)c3C=C1CCN(S(=O)(=O)c1cccnc1)C2]

Preparation 2a. (R)-1-(4-Fluorophenyl)-4a-hydroxymethyl-1,4,4a,5,7,8-hexahydro-1,2,6-triazacyclopenta[b]naphthalene-6-carboxylic acid tert-butyl ester The title compound was prepared by the method of Preparation 1d using (R)-1-(4-fluorophenyl)-1,4,7,8-tetrahydro-1, 2,6-triazacyclopenta[b]naphthalene-4a,6-dicarboxylic acid 6-tert-butyl ester 4a-methyl ester. LCMS (Method B): 400 (M+H)+, Retention time 3.8 minutes.

Preparation 2b. (R)-4a-Ethoxymethyl-1-(4-fluorophenyl)-1,4,4a,5,7,8-hexahydro-1,2,6-triazacyclopenta[b]naphthalene-6-carboxylic acid tert-butyl ester A solution of (R)-1-(4-fluorophenyl)-4a-hydroxymethyl-1,4,4a,5,7,8-hexahydro-1,2,6-triazacyclopenta[b]naphthalene-6-carboxylic acid tert-butyl ester (0.25 g) in tetrahydrofuran (2.5 mL) under argon at room temperature was treated sequentially with sodium hydride (0.072 g, 60% dispersion in mineral oil) and iodoethane (0.15 mL), and the resulting mixture was stirred at 50° C. for 2 hour. The solution was cooled to room temperature, diluted with ethyl acetate, washed with saturated aqueous ammonium chloride solution, water and brine, and dried over sodium sulfate. The solvent was removed under reduced pressure, and the residue was purified by column chromatography on silica gel, eluting with a mixture of dichloromethane and ethyl acetate (9:1 by volume), to afford the title compound as an amber gum (0.21 g). LCMS (Method E): 428 (M+H)+, Retention time 4.7 minutes.

Preparation 2c. (R)-4a-Ethoxymethyl-1-(4-fluorophenyl)-6-[[3-pyridinyl]sulfonyl]-1,4,7,8-tetrahydro-1,2,6-triazacyclopenta[b]naphthalene The title compound was prepared by the method of Preparation 1c using (R)-4a-ethoxymethyl-1-(4-fluorophenyl)-1,4,4a,5,7,8-hexahydro-1,2,6-triaza-cyclopenta[b]naphthalene-6-carboxylic acid tert-butyl ester and pyridine-3-sulfonyl chloride. LCMS (Method C): 469 (M+H)+, Retention time 11.1 minutes.

Example 3

(R)-4a-Ethoxymethyl-1-(4-fluorophenyl)-6-[[2H-pyrido[3.2-b]-1,4-oxazin-7-yl]sulfonyl]-1,4,7,8-tetrahydro-1,2,6-triazacyclopenta[b]naphthalene

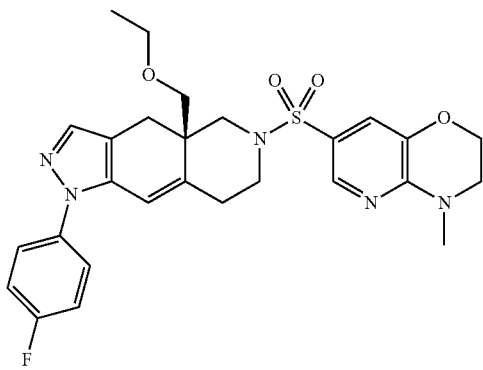 [SMILES: CCOC[C@]12Cc3cnn(-c4ccc(F)cc4)c3C=C1CCN(S(=O)(=O)c1cnc3c(c1)OCCN3C)C2]

The title compound was prepared by the method of Preparation 1c using (R)-4a-ethoxymethyl-1-(4-fluorophenyl)-1,4,4a,5,7,8-hexahydro-1,2,6-triazacyclopenta[b]naphthalene-6-carboxylic acid tert-butyl ester and 4-methyl-3,4-dihydro-2H-pyrido[3,2-b][1,4]oxazine-7-sulfonyl chloride. LCMS (Method C): 540 (M+H)+, Retention time 11.9 minutes.

Example 4

(R)-4a-Ethoxymethyl-1-(4-fluorophenyl)-6-[[6-(1-pyrrolidinyl)-3-pyridinyl]sulfonyl]-1,4,7,8-tetrahydro-1,2,6-triazacyclopenta naphthalene

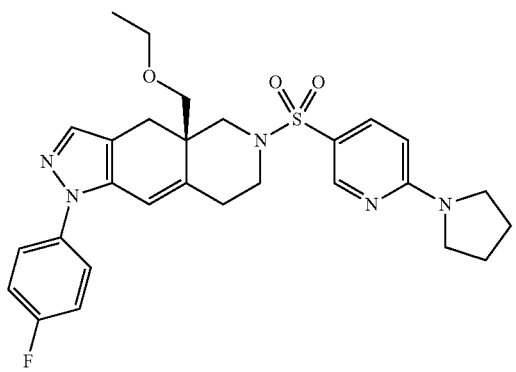 [SMILES: CCOC[C@]12Cc3cnn(-c4ccc(F)cc4)c3C=C1CCN(S(=O)(=O)c1ccc(N3CCCC3)nc1)C2]

Preparation 4a. (R)-6-(6-Chloropyridine-3-sulfonyl)-4a-ethoxymethyl-1-(4-fluorophenyl)-4,4a,5,6,7,8-hexahydro-1H-1,2,6-triazacyclopenta[b]naphthalene The title compound was prepared by the method of Preparation 1c using (R)-4a-ethoxymethyl-1-(4-fluorophenyl)-1,4,4a,5,7,8-hexahydro-1,2,6-triazacyclopenta[b]naphthalene-6-carboxylic acid tert-butyl ester and 6-chloropyridine-3-sulfonyl chloride. LCMS (Method B): 503 (M+H)+, Retention time 4.1 minutes.

Preparation 4b. (R)-4a-Ethoxymethyl-1-(4-fluorophenyl)-6-[[6-(1-pyrrolidinyl)-3-pyridinyl]sulfonyl]-1,4,7,8-tetrahydro-1,2,6-triazacyclopenta[b]naphthalene A solution of (R)-6-(6-chloropyridine-3-sulfonyl)-4a-ethoxymethyl-1-(4-fluorophenyl)-4,4a,5,6,7,8-hexahydro-1H-1,2,6-triazacyclopenta[b]naphthalene (0.013 g) and pyrrolidine (0.025 mL) in acetonitrile was heated at 100° C. in a microwave reactor for 10 minutes. The solution was concentrated under reduced pressure, and the residue was purified by column chromatography on silica gel, eluting with a mixture of dichloromethane and ethyl acetate (5:1 by volume), to afford the title compound as a clear gum (0.0080 g). LCMS (Method B): 538 (M+H)+, Retention time 4.0 minutes.

Example 5

(R)-1-(4-Fluorophenyl)-4a-methoxymethyl-6-[[6-(1-pyrrolidinyl)-3-pyridinyl]sulfonyl]-1,4,7,8-tetrahydro-1,2,6-triazacyclopenta[b]naphthalene

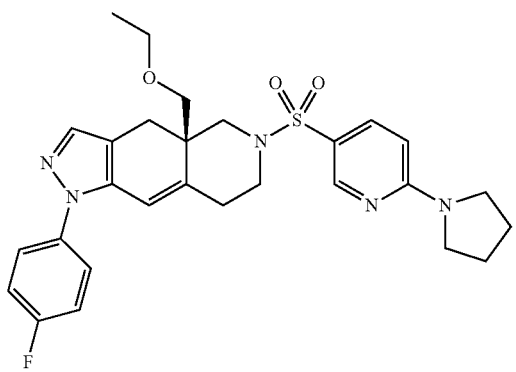 [SMILES: CCOC[C@]12Cc3cnn(-c4ccc(F)cc4)c3C=C1CCN(S(=O)(=O)c1ccc(N3CCCC3)nc1)C2]

Preparation 5a. (R)-1-(4-Fluorophenyl)-4a-methoxymethyl-1,4,4a,5,7,8-hexahydro-1,2,6-triazacyclopenta[b]naphthalene-6-carboxylic acid tert-butyl ester The title compound was prepared by the method of Preparation 2b using (R)-1-(4-fluorophenyl)-4a-hydroxymethyl-1,4,4a,5,7,8-hexahydro-1,2,6-triazacyclopenta[b]naphthalene-6-carboxylic acid tert-butyl ester and iodomethane. LCMS (Method D): 414 (M+H)+, Retention time 4.3 minutes.

Preparation 5b. (R)-6-(6-Chloropyridine-3-sulfonyl)-1-(4-fluorophenyl)-4a-methoxymethyl-4,4a,5,6,7,8-hexahydro-1H-1,2,6-triaza-cyclopenta[b]naphthalene The title compound was prepared by the method of Preparation 2b using (R)-1-(4-fluorophenyl)-4a-methoxymethyl-1,4,4a,5,7,8-hexahydro-1,2,6-triazacyclopenta[b]naphthalene-6-carboxylic acid tert-butyl ester and 6-chloropyridine-3-sulfonyl chloride. LCMS (Method B): 489 (M+H)+, Retention time 3.9 minutes.

Preparation 5c. (R)-1-(4-Fluorophenyl)-4a-methoxymethyl-6-[[6-(1-pyrrolidinyl)-3-pyridinyl]sulfonyl]-1,4,7,8-tetrahydro-1,2,6-triazacyclopenta[b]naphthalene The title compound was prepared by the method of Preparation 4b using (R)-6-(6-chloropyridine-3-sulfonyl)-1-(4-fluorophenyl)-4a-methoxymethyl-4,4a,5,6,7,8-hexahydro-1H-1,2,6-triazacyclopenta[b]naphthalene and pyrrolidine. LCMS (Method C): 524 (M+H)+, Retention time 11.6 minutes.

Example 6

(R)-6-[[6-(1-Azetidinyl)-3-pyridinyl]sulfonyl]-4a-ethoxymethyl-1-(4-fluorophenyl)-1,4,7,8-tetrahydro-1,2,6-triazacyclopenta[b]naphthalene

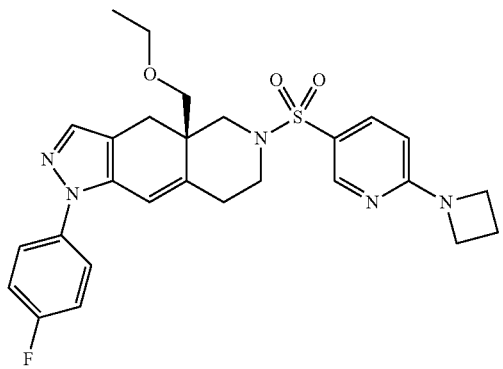 [SMILES: CCOC[C@]12Cc3cnn(-c4ccc(F)cc4)c3C=C1CCN(S(=O)(=O)c1ccc(N3CCC3)nc1)C2]

The title compound was prepared by the method of Preparation 4b using (R)-6-(6-chloropyridine-3-sulfonyl)-4a-ethoxymethyl-1-(4-fluorophenyl)-4,4a,5,6,7,8-hexahydro-1H-1,2,6-triazacyclopenta[b]naphthalene and azetidine. LCMS (Method C): 524 (M+H)+, Retention time 11.6 minutes.

Example 7

(R)-4a-Ethoxymethyl-1-(4-fluorophenyl)-6-[[6-methylamino-3-pyridinyl]sulfonyl]-1,4,7,8-tetrahydro-1,2,6-triazacyclopenta[b]naphthalene

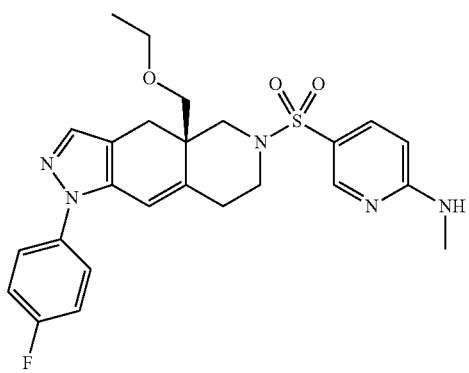 [SMILES: CCOC[C@]12Cc3cnn(-c4ccc(F)cc4)c3C=C1CCN(S(=O)(=O)c1ccc(NC)nc1)C2]

The title compound was prepared by the method of Preparation 4b using (R)-6-(6-chloropyridine-3-sulfonyl)-4a-ethoxymethyl-1-(4-fluorophenyl)-4,4a,5,6,7,8-hexahydro-1H-1,2,6-triazacyclopenta[b]naphthalene and methylamine. LCMS (Method B): 498 (M+H)+, Retention time 3.6 minutes.

Example 8

(R)-6-[[6-Dimethylamino-3-pyridinyl]sulfonyl]-4a-ethoxymethyl-1-(4-fluorophenyl)-1,4,7,8-tetrahydro-1,2,6-triazacyclopenta[b]naphthalene

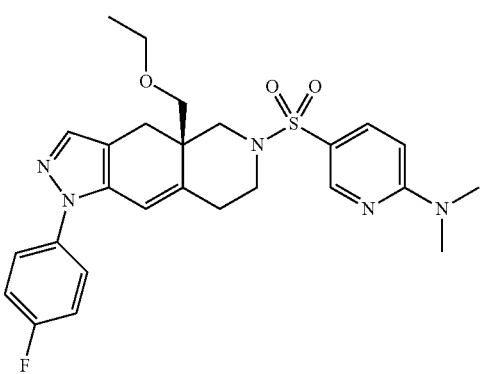 [SMILES: CCOC[C@]12Cc3cnn(-c4ccc(F)cc4)c3C=C1CCN(S(=O)(=O)c1ccc(N(C)C)nc1)C2]

The title compound was prepared by the method of Preparation 4b using (R)-6-(6-chloropyridine-3-sulfonyl)-4a-ethoxymethyl-1-(4-fluorophenyl)-4,4a,5,6,7,8-hexahydro- 1H-1,2,6-triazacyclopenta[b]naphthalene and dimethylamine. LCMS (Method C): 512 (M+H)+, Retention time 12.1 minutes.

Example 9

(R)-1-(4-Fluorophenyl)-4a-methoxymethyl-6-[[6-methylamino-3-pyridinyl]sulfonyl]-1,4,7,8-tetrahydro-1,2,6-triazacyclopenta[b]naphthalene

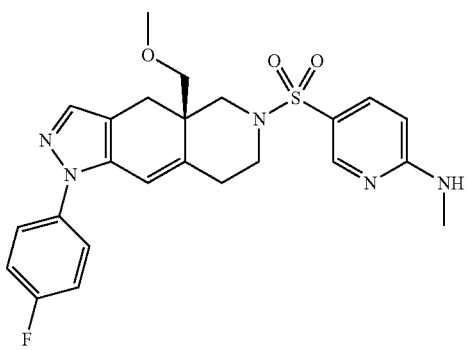 [SMILES: CNc1ccc(S(=O)(=O)N2CCC3=Cc4c(cnn4-c4ccc(F)cc4)C[C@]3(COC)C2)cn1]

The title compound was prepared by the method of Preparation 4b using (R)-6-(6-chloropyridine-3-sulfonyl)-1-(4-fluorophenyl)-4a-methoxymethyl-4,4a,5,6,7,8-hexahydro-1H-1,2,6-triazacyclopenta[b]naphthalene and methylamine. LCMS (Method C): 484 (M+H)+, Retention time 9.8 minutes.

Example 10

(R)-6-[[6-Dimethylamino-3-pyridinyl]sulfonyl]-1-(4-fluorophenyl)-4a-methoxymethyl-1,4,7,8-tetrahydro-1,2,6-triazacyclopenta[b]naphthalene

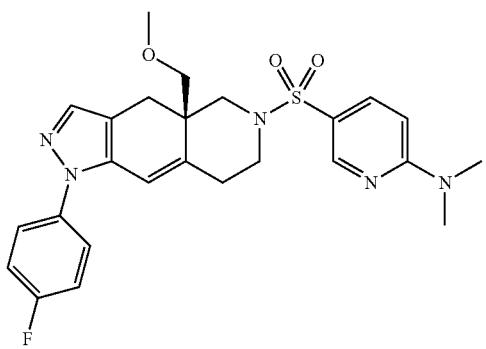 [SMILES: COC[C@]12Cc3cnn(-c4ccc(F)cc4)c3C=C1CCN(S(=O)(=O)c1ccc(N(C)C)nc1)C2]

The title compound was prepared by the method of Preparation 4b using (R)-6-(6-chloropyridine-3-sulfonyl)-1-(4-fluorophenyl)-4a-methoxymethyl-4,4a,5,6,7,8-hexahydro-1H-1,2,6-triazacyclopenta[b]naphthalene and dimethylamine. LCMS (Method C): 498 (M+H)+, Retention time 11.4 minutes.

Example 11

(R)-6-[[6-(1-Azetidinyl)-3-pyridinyl]sulfonyl]-1-(4-fluorophenyl)-4a-methoxymethyl-1,4,7,8-tetrahydro-1,2,6-triazacyclopenta[b]naphthalene

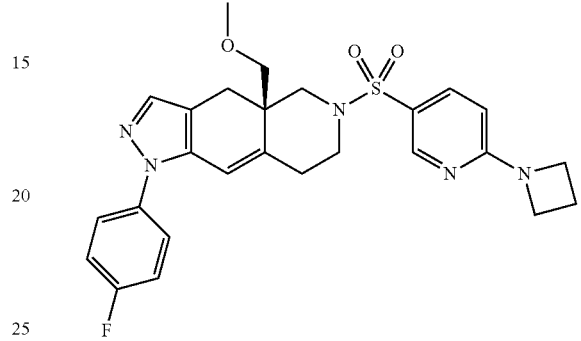

The title compound was prepared by the method of Preparation 4b using (R)-6-(6-chloropyridine-3-sulfonyl)-1-(4-fluorophenyl)-4a-methoxymethyl-4,4a,5,6,7,8-hexahydro-1H-1,2,6-triazacyclopenta[b]naphthalene and azetidine. LCMS (Method C): 510 (M+H)+, Retention time 10.9 minutes.

Example 12

(R)-1-(4-Fluorophenyl)-4a-methoxymethyl-6-(5-morpholin-4-ylpyridine-3-sulfonyl)-4,4a,5,6,7,8-hexahydro-1H-1,2,6-triazacyclopenta[b]naphthalene

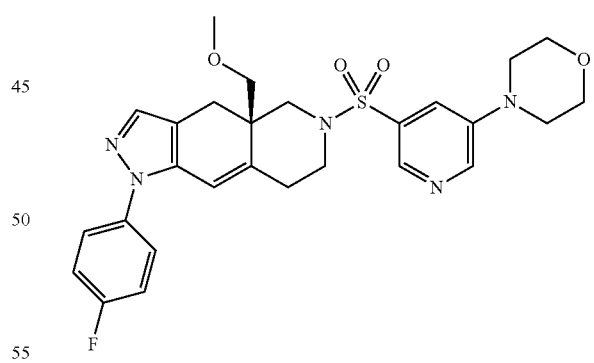

Preparation 12a. (R)-1-(4-Fluorophenyl)-4a-methoxymethyl-1,4,4a,5,7,8-hexahydro-1,2,6-triazacyclopenta[b]naphthalene-6-carboxylic acid tert-butyl ester The title compound was prepared by the method of Preparation 2b using (R)-1-(4-fluoro-phenyl)-4a-hydroxymethyl-1,4,4a,5,7,8-hexahydro-1,2,6-triazacyclopenta[b]naphthalene-6-carboxylic acid tert-butyl ester and iodomethane. $^1$H NMR (CDCl$_3$): δ 7.47-7.40 (m, 3H), 7.19-7.12 (m, 2H), 6.32-6.29 (d, 1H, J=2.2 Hz), 4.45-4.30 (d, 1H, J=14 Hz), 4.27-3.92 (bs, 1H), 3.29 (s, 3H), 3.19-3.13 (d, 1H, J=9.1 Hz), 3.09-2.97 (d, 2H, J=16 Hz), 2.92-2.65 (m, 2H), 2.59-2.46 (m, 1H), 2.40-2.20 (m, 2H), 1.49 (s, 9H).

Preparation 12b. (R)-6-(5-Bromopyridine-3-sulfonyl)-1-(4-fluorophenyl)-4a-methoxymethyl-4,4a,5,6,7,8-hexahydro-1H-1,2,6-triazacyclopenta[b]naphthalene The title compound was prepared by the method of Preparation 1c using (R)-1-(4-Fluorophenyl)-4a-methoxymethyl-1,4,4a,5,7,8-hexahydro-1,2,6-triazacyclopenta[b]naphthalene-6-carboxylic acid tert-butyl ester and 5-bromopyridine-3-sulfonyl chloride. LCMS (Method D): 533 (M+H)$^+$, Retention time 4.1 minutes.

Preparation 12c. (R)-1-(4-Fluorophenyl)-4a-methoxymethyl-6-(5-morpholin-4-ylpyridine-3-sulfonyl)-4,4a,5,6,7,8-hexahydro-1H-1,2,6-triazacyclopenta[b]naphthalene A mixture of (R)-6-(5-bromopyridine-3-sulfonyl)-1-(4-fluorophenyl)-4a-methoxymethyl-4,4a,5,6,7,8-hexahydro-1H-1,2,6-triazacyclopenta[b]naphthalene (0.15 g), (±)-2,2'-bis(diphenylphosphino)-1,1'-binaphthyl (0.035 g), tris(dibenzylideneacetone)dipalladium (0.026 g), sodium tert-butoxide (0.049 g), morpholine and tetrahydrofuran was heated at 100° C. in a microwave reactor for 30 minutes. The mixture was filtered through Celite, and the pad was washed with ethyl acetate. The filtrate was concentrated under reduced pressure, and the residue was purified by column chromatography on silica gel, eluting with a mixture of cyclohexane and ethyl acetate (4:1 by volume), to afford a yellow oil. The yellow oil was purified by preparative reverse-phase HPLC, eluting with a mixture of methanol and water containing 0.1% formic acid (9:20 to 4:3 by volume) to afford the title compound as a white solid (0.097 g). LCMS (Method C): 540 (M+H)$^+$, Retention time 10.6 minutes.

Example 13

(R)-6-(5-Azetidin-1-ylpyridine-3-sulfonyl)-1-(4-fluorophenyl)-4a-methoxymethyl-4,4a,5,6,7,8-hexahydro-1H-1,2,6-triazacyclopenta[b]naphthalene

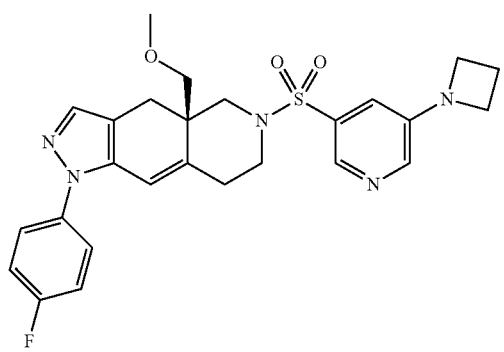 [SMILES: COC[C@]12Cc3cnn(-c4ccc(F)cc4)c3C=C1CCN(S(=O)(=O)c1cncc(N3CCC3)c1)C2]

The title compound was prepared by the method of Preparation 12c using (R)-6-(5-bromopyridine-3-sulfonyl)-1-(4-fluorophenyl)-4a-methoxymethyl-4,4a,5,6,7,8-hexahydro-1H-1,2,6-triazacyclopenta[b]naphthalene and azetidine. LCMS (Method C): 510 (M+H)$^+$, Retention time 11.3 minutes.

Example 14

(R)-1-(4-Fluorophenyl)-4a-methoxymethyl-6-(6-morpholin-4-yl-pyridine-3-sulfonyl)-4,4a,5,6,7,8-hexahydro-1H-1,2,6-triazacyclopenta[b]naphthalene

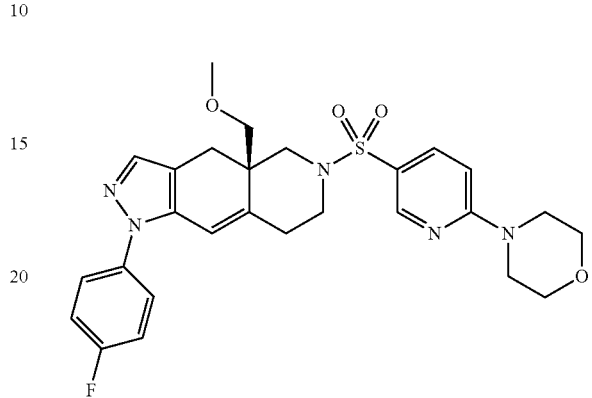

Method A.

A suspension of sodium hydride (1.5 g, 60% dispersion in mineral oil) in tetrahydrofuran (20 mL) at room temperature was treated sequentially with a solution of [(R)-1-(4-fluorophenyl)-6-[[6-(4-morpholinyl)-3-pyridinyl]sulfonyl]-1,4,7,8-tetrahydro-1,2,6-triazacyclopenta[b]naphthalen-4a-yl]methanol (8.0 g) in tetrahydrofuran (60 mL) and iodomethane (2.9 mL), and the resulting mixture was stirred at 50° C. for 1 hour. The mixture was cooled to room temperature and partitioned between ethyl acetate and 1.0 M aqueous hydrochloric acid solution. The aqueous phase was extracted with ethyl acetate, and the combined organic phase was washed with aqueous sodium thiosulfate solution, aqueous potassium carbonate solution, water and brine, and then dried over sodium sulfate. The solvent was removed under reduced pressure, and the residue was purified by column chromatography on silica gel, eluting with a mixture of dichloromethane and diethyl ether (1:19 to 1:9 by volume), and then by crystallization from industrial methylated spirits to afford the title compound as a white solid (6.7 g). $^1$H NMR (CDCl$_3$): δ 8.53-8.49 (d, 1H, J=2.3 Hz), 7.79-7.74 (dd, 1H, J=9.2, 2.5 Hz), 7.40-7.34 (m, 3H), 7.15-7.08 (m, 2H), 6.61-6.57 (d, 1H, J=9.3 Hz), 6.26-6.23 (d, 1H, J=2.1 Hz), 4.11-4.06 (dd, 1H, J=12, 2.1 Hz), 3.89-3.82 (m, 1H), 3.79-3.73 (m, 4H), 3.65-3.59 (m, 4H), 3.39-3.34 (d, 1H, J=8.9 Hz), 3.32 (s, 3H), 3.11-3.02 (m, 2H), 2.73-2.61 (m, 1H), 2.41-2.30 (m, 2H), 2.20-2.21 (dd, 2H, J=33, 16 Hz).

Method B.

A mixture of (R)-6-(6-chloropyridine-3-sulfonyl)-1-(4-fluorophenyl)-4a-methoxymethyl-4,4a,5,6,7,8-hexahydro-1H-1,2,6-triazacyclopenta[b]naphthalene (174.0 g, 356 mmol), potassium carbonate (240.0 g) and morpholine (156.0 g, 1735 mmol) in acetonitrile (880 mL) was heated to 70° C. for 3 h. The mixture was cooled to 20-25° C., diluted with dichloromethane (1.5 L), and quenched with water (1.0 L). The layers were separated, and the organic layer was washed with water (2×1.0 L), dried over MgSO$_4$, and filtered. The filtrate was concentrated to an oil (265 g). Ethanol (1.5 L) was added, and the resulting solution was concentrated to afford a thick slurry that was filtered, and washed with ethanol. Crystallization from ethyl acetate/heptane afforded 106 g of the title compound: mp 174° C.

Example 15

(R)-4a-Difluoromethoxymethyl-1-(4-fluorophenyl)-6-(6-morpholin-4-yl-pyridine-3-sulfonyl)-4,4a,5,6,7,8-hexahydro-1H-1,2,6-triazacyclopenta[b]naphthalene

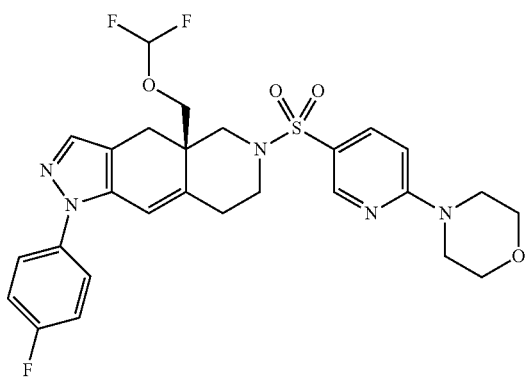 [SMILES: O=S(=O)(c1ccc(N2CCOCC2)nc1)N1CCC2=Cc3c(cnn3-c3ccc(F)cc3)C[C@]2(COC(F)F)C1]

A mixture of [(R)-1-(4-fluorophenyl)-6-[[6-(4-morpholinyl)-3-pyridinyl]sulfonyl]-1,4,7,8-tetrahydro-1,2,6-triazacyclopenta[b]naphthalen-4a-yl]methanol (0.21 g), copper iodide (0.0080 g) and acetonitrile under argon was treated with 2-(fluorosulfonyl)difluoroacetic acid (0.062 mL), and the resulting mixture was heated at 50° C. for 30 hours. The mixture was cooled to room temperature, partitioned between water and ethyl acetate and the aqueous phase extracted with ethyl acetate. The combined organic phase was dried over sodium sulfate and concentrated under reduced pressure. The residue was purified by column chromatography on silica gel, eluting with a mixture of cyclohexane and ethyl acetate (1:0 to 1:1 by volume), and then by preparative reverse-phase HPLC, eluting with a mixture of acetonitrile and water containing 0.1% formic acid (1:1 to 7:3 by volume) to afford the title compound as a white solid (0.021 g). LCMS (Method C): 576 (M+H)$^+$, Retention time 11.6 minutes.

Example 16

(R)-6-(6-Azetidin-1-yl-pyridine-3-sulfonyl)-1-(4-fluorophenyl)-4a-(oxazol-2-ylmethoxymethyl)-4,4a,5,6,7,8-hexahydro-1H-1,2,6-triazacyclopenta[b]naphthalene

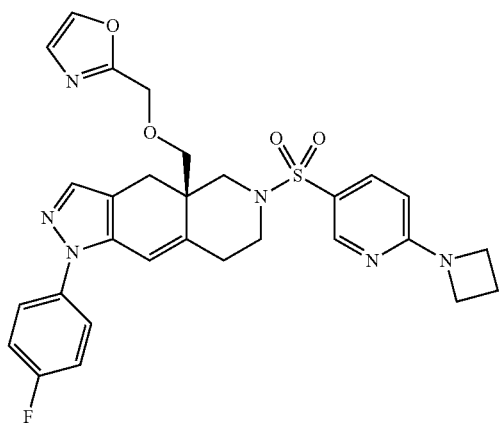 [SMILES: O=S(=O)(c1ccc(N2CCC2)nc1)N1CCC2=Cc3c(cnn3-c3ccc(F)cc3)C[C@]2(COCc2ncco2)C1]

Preparation 16a. (R)-6-(6-Chloropyridine-3-sulfonyl)-1-(4-fluorophenyl)-1,4,5,6,7,8-hexahydro-1,2,6-triazacyclopenta[b]naphthalene-4a-carboxylic acid methyl ester The title compound was prepared by the method of Preparation 2b using (R)-1-(4-fluoro-phenyl)-1,4,7,8-tetrahydro-1,2,6-triazacyclopenta[b]naphthalene-4a,6-dicarboxylic acid 6-tert-butyl ester 4a-methyl ester. LCMS (Method B): 503 (M+H)$^+$, Retention time 3.8 minutes.

Preparation 16b. (R)-6-(6-Azetidin-1-yl-pyridine-3-sulfonyl)-1-(4-fluorophenyl)-1,4,5,6,7,8-hexahydro-1,2,6-triaza-cyclopenta[b]naphthalene-4a-carboxylic acid methyl ester The title compound was prepared by the method of Preparation 4b using (R)-6-(6-chloropyridine-3-sulfonyl)-1-(4-fluorophenyl)-1,4,5,6,7,8-hexahydro-1,2,6-triazacyclopenta[b]na-phthalene-4a-carboxylic acid methyl ester and azetidine. LCMS (Method B): 524 (M+H)$^+$, Retention time 3.5 minutes.

Preparation 16c. [(R)-6-(6-Azetidin-1-yl-pyridine-3-sulfonyl)-1-(4-fluorophenyl)-1,4,5,6,7,8-hexahydro-1,2,6-triazacyclopenta[b]naphthalen-4a-yl]methanol The title compound was prepared by the method of Preparation 1d using (R)-6-(6-azetidin-1-yl-pyridine-3-sulfonyl)-1-(4-fluorophenyl)-1,4,5,6,7,8-hexahydro-1,2,6-triaza-cyclopenta[b]naphtha-lene-4a-carboxylic acid methyl ester. LCMS (Method D): 496 (M+H)$^+$, Retention time 3.2 minutes.

Preparation 16d. (R)-6-(6-Azetidin-1-yl-pyridine-3-sulfonyl)-1-(4-fluorophenyl)-4a-(oxazol-2-yl-methoxymethyl)-4,4a,5,6,7,8-hexahydro-1H-1,2,6-triazacyclopenta[b]naphthalene The title compound was prepared by the method of Preparation 2b using [(R)-6-(6-azetidin-1-yl-pyridine-3-sulfonyl)-1-(4-fluorophenyl)-1,4,5,6,7,8-hexahydro-1,2,6-triazacyclopenta[b]naphthal-en-4a-yl]methanol and 2-chloromethyloxazole. LCMS (Method C): 577 (M+H)$^+$, Retention time 10.2 minutes.

Example 17

(R)-6-(6-Azetidin-1-ylpyridine-3-sulfonyl)-4a-difluoromethoxymethyl-1-(4-fluorophenyl)-4,4a,5,6,7,8-hexahydro-1H-1,2,6-triazacyclopenta[b]naphthalene

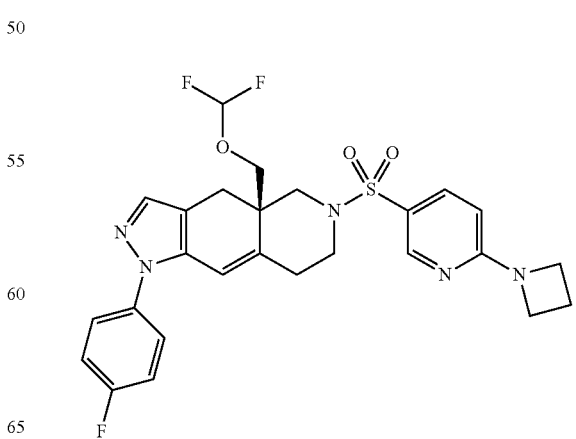

The title compound was prepared by the method of Preparation 15a using [(R)-6-(6-azetidin-1-yl-pyridine-3-sulfonyl)-1-(4-fluorophenyl)-1,4,5,6,7,8-hexahydro-1,2,6-triazacyclopenta[b]naphth-alen-4a-yl]methanol. LCMS (Method D): 546 (M+H)+, Retention time 3.8 minutes.

Example 18

(R)-1-(4-Fluorophenyl)-4a-methoxymethyl-6-[[6-(1-piperazinyl)-3-pyridinyl]sulfonyl]-1,4,7,8-tetrahydro-1,2,6-triazacyclopenta[b]naphthalene

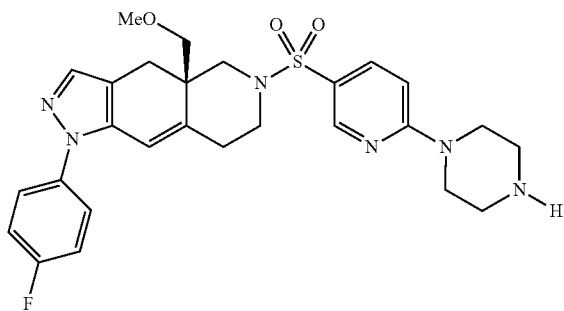 [SMILES: COC[C@]12Cc3cnn(-c4ccc(F)cc4)c3C=C1CCN(S(=O)(=O)c1ccc(N3CCNCC3)nc1)C2]

The title compound was prepared by the method of Preparation 4b using (R)-6-(6-chloropyridine-3-sulfonyl)-1-(4-fluorophenyl)-4a-methoxymethyl-4,4a,5,6,7,8-hexahydro-1H-1,2,6-triazacyclopenta[b]naphthalene and piperazine. LCMS (Method C): 539 (M+H)+, Retention time 7.4 minutes.

Example 19

(R)-1-(4-Fluorophenyl)-4a-methoxymethyl-6-[[6-(1-(4-methylpiperazinyl))-3-pyridinyl]sulfonyl]-1,4,7,8-tetrahydro-1,2,6-triazacyclopenta[b]naphthalene

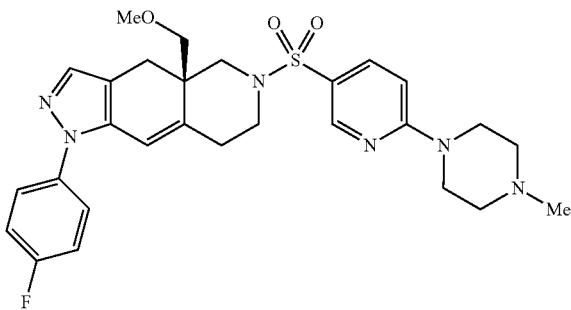 [SMILES: COC[C@]12Cc3cnn(-c4ccc(F)cc4)c3C=C1CCN(S(=O)(=O)c1ccc(N3CCN(C)CC3)nc1)C2]

The title compound was prepared by the method of Preparation 4b using (R)-6-(6-chloropyridine-3-sulfonyl)-1-(4-fluorophenyl)-4a-methoxymethyl-4,4a,5,6,7,8-hexahydro-1H-1,2,6-triazacyclopenta[b]naphthalene and 4-methylpiperazine. LCMS (Method C): 553 (M+H)+, Retention time 7.4 minutes.

Example 20

(R)-1-(4-Fluorophenyl)-6-[6-((R)-3-fluoropyrrolidin-1-yl)-pyridine-3-sulfonyl]-4a-methoxymethyl-4,4a,5,6,7,8-hexahydro-1H-1,2,6-triaza-cyclopenta[b]naphthalene

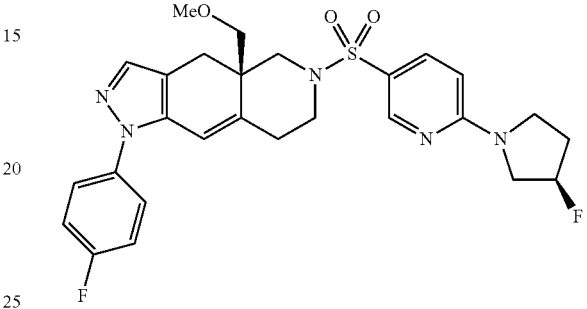

A solution of (R)-6-(6-chloropyridine-3-sulfonyl)-4a-methoxymethyl-1-(4-fluorophenyl)-4,4a,5,6,7,8-hexahydro-1H-1,2,6-triazacyclopenta[b]naphthalene (0.098 g), diisopropylethylamine (0.194 g) and (R)-3-fluoropyrrolidine hydrochloride in acetonitrile was heated at 130° C. in a microwave reactor for 45 minutes. The solution was diluted with ethyl acetate, washed with water followed by brine, dried over sodium sulfate, filtered and the filtrate concentrated under reduced pressure. The residue was purified by column chromatography on silica gel, eluting with ethyl acetate in cyclohexane (0 to 3:2 by volume), to afford the title compound as a white solid (0.089 g). LCMS (Method F): 542 (M+H)+, Retention time 5.0 minutes Example 21

(R)-1-{5-[(R)-1-(4-Fluorophenyl)-4a-methoxymethyl-1,4,4a,5,6,7,8-hexahydro-1,2,6-triaza-cyclopenta[b]naphthalene-6-sulfonyl]-pyridin-2-yl}-pyrrolidin-3-ol The title compound was prepared by the method of Example 20 using (R)-6-(6-chloropyridine-3-sulfonyl)-4a-methoxymethyl-1-(4-fluorophenyl)-4,4a,5,6,7,8-hexahydro-1H-1,2,6-triazacyclopenta[b]naphthalene, diisopropylethy-

Example 22

(S)-1-{5-[(R)-1-(4-Fluorophenyl)-4a-methoxymethyl-1,4,4a,5,6,7,8-hexahydro-1,2,6-triaza-cyclopenta[b]naphthalene-6-sulfonyl]-pyridin-2-yl}-pyrrolidin-3-ol

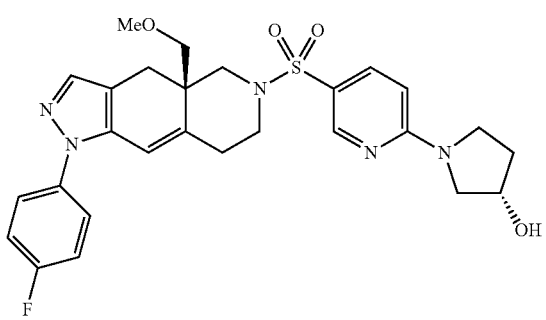 [SMILES: COC[C@]12Cc3cnn(-c4ccc(F)cc4)c3C=C1CCN(S(=O)(=O)c1ccc(N3CC[C@H](O)C3)nc1)C2]

The title compound was prepared by the method of Example 20 using (R)-6-(6-chloropyridine-3-sulfonyl)-4a-methoxymethyl-1-(4-fluorophenyl)-4,4a,5,6,7,8-hexahydro-1H-1,2,6-triazacyclopenta[b]naphthalene, diisopropylethylamine and (R)-3-hydroxypyrrolidine hydrochloride. LCMS (Method F): 540 (M+H)⁺, Retention time 4.3 minutes.

Example 23

(R)-1-(4-Fluorophenyl)-4a-methoxymethyl-6-[(1S,4S)-6-(2-oxa-5-aza-bicyclo[2.2.1]hept-5-yl)pyridine-3-sulfonyl]-4,4a,5,6,7,8-hexahydro-1H-1,2,6-triaza-cyclopenta[b]naphthalene

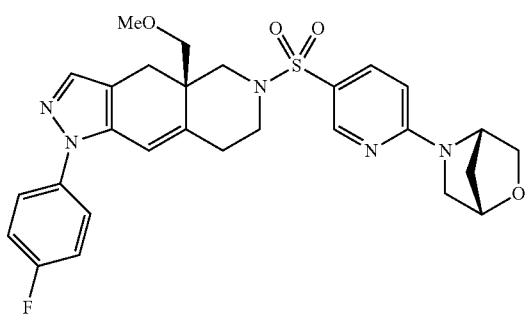 [SMILES: COC[C@]12Cc3cnn(-c4ccc(F)cc4)c3C=C1CCN(S(=O)(=O)c1ccc(N3C[C@@H]4C[C@H]3CO4)nc1)C2]

The title compound was prepared by the method of Example 20 using (R)-6-(6-chloropyridine-3-sulfonyl)-4a-methoxymethyl-1-(4-fluorophenyl)-4,4a,5,6,7,8-hexahydro-1H-1,2,6-triazacyclopenta[b]naphthalene, diisopropylethylamine and (1S,4S)-2-oxa-5-azabicyclo[2.2.1]heptane hydrochloride. LCMS (Method F): 552 (M+H)⁺, Retention time 4.7 minutes.

Example 24

(R)-1-(4-Fluorophenyl)-4a-methoxymethyl-6-(6-trifluoromethylpyridine-3-sulfonyl)-4,4a,5,6,7,8-hexahydro-1H-1,2,6-triaza-cyclopenta[b]naphthalene

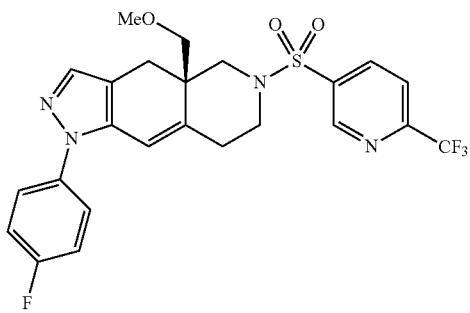 [SMILES: COC[C@]12Cc3cnn(-c4ccc(F)cc4)c3C=C1CCN(S(=O)(=O)c1ccc(C(F)(F)F)nc1)C2]

The title compound was prepared by the method of Preparation 1c using (R)-4a-methoxymethyl-1-(4-fluorophenyl)-1,4,4a,5,6,7,8-hexahydro-1H-1,2,6-triazacyclopenta[b]naphthalene-6-carboxylic acid tert-butyl ester and 6-(trifluoromethyl)pyridine-3-sulfonyl chloride. LCMS (Method F): 523 (M+H)⁺, Retention time 5.4 minutes.

Example 25

(R)-4a-Cyclopropylmethoxymethyl-1-(4-fluorophenyl)-6-(6-pyrrolidin-1-yl-pyridine-3-sulfonyl)-4,4a,5,6,7,8-hexahydro-1H-1,2,6-triaza-cyclopenta[b]naphthalene

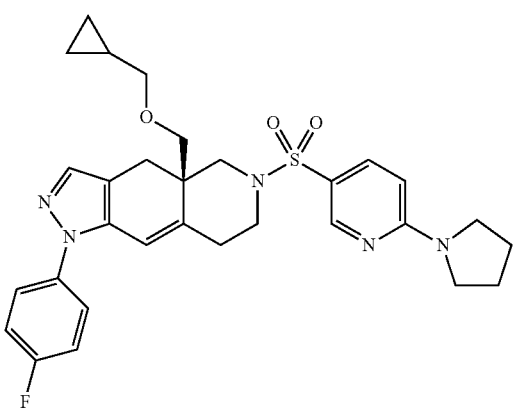 [SMILES: O=S(=O)(c1ccc(N2CCCC2)nc1)N1CCC2=Cc3c(cnn3-c3ccc(F)cc3)C[C@]2(COCC2CC2)C1]

Preparation 25a. (R)-1-(4-Fluorophenyl)-4a-hydroxymethyl-1,4,4a,5,6,7,8-hexahydro-1,2,6-triaza-cyclopenta[b]naphthalene-6-carboxylic acid tert-butyl ester A solution of (R)-1-(4-fluorophenyl)-1,4,7,8-tetrahydro-1,2,6-triaza-cyclopenta[b]naphthalene-4a,6-carboxylic acid-6-tert-butyl ester-4a-methyl ester (5.2 g) in dichloromethane (150 mL) under nitrogen at −78° C. was treated with a 1.0 M solution of diisobutylaluminium hydride in dichloromethane (48.8 mL). After 1 hour at −78° C., the solution was diluted with water and warmed to room temperature. Solid sodium bicarbonate was added and the suspension stirred for 10 minutes. Solid sodium sulfate was added and the suspension stirred for 20 minutes. The granular solids were removed by filtration, washed with ethyl acetate and the filtrate concentrated under reduced pressure. The residue was dissolved in methanol (100 mL) at 4° C. and treated with sodium borohydride (0.92 g) for 1 hour whilst allowing the temperature to rise. The solvent was evaporated under reduced pressure and the residue dissolved in ethyl acetate. The organic phase was washed with water and brine, dried over sodium sulfate, filtered to remove solids and the filtrate concentrated under reduced pressure. The residue was triturated with cyclohexane to afford the title compound as a white solid (2.95 g). LCMS (Method G): 400.1 (M+H)$^+$, Retention time 3.68 minutes.

Preparation 25b. (R)-4a-Cyclopropylmethoxyoxymethyl-1-(4-fluorophenyl)-1,4,4a,5,6,7,8-hexahydro-1,2,6-triaza-cyclopenta[b]naphthalene-6-carboxylic acid tert-butyl ester A solution of (R)-1-(4-fluorophenyl)-4a-hydroxymethyl-1,4,4a,5,6,7,8-hexahydro-1,2,6-triaza-cyclopenta[b]naphthalene-6-carboxylic acid tert-butyl ester (0.49 g) in tetrahydrofuran (10 mL) was treated with 50% (w/v) aqueous sodium hydroxide solution (5 mL), tetrabutylammonium hydrogensulfate (0.21 g), tetrabutylammonium iodide (0.91 g) and cyclopropylmethyl bromide (0.33 g) at 40° C. for 6 hours. Further tetrabutylammonium hydrogensulfate (0.21 g), tetrabutylammonium iodide (0.91 g) and cyclopropylmethyl bromide (0.33 g) were added and the reaction mixture stirred at 40° C. for 16 hours. The reaction mixture was diluted with water and the phases separated. The organic phase was dried over sodium sulfate and concentrated under reduced pressure. The residue was purified by column chromatography on silica gel, eluting with ethyl acetate in cyclohexane (0 to 1:4 by volume) to afford the title compound as an opaque glass on standing (0.42 g). LCMS (Method G): 454.2 (M+H)$^+$, Retention time 4.46 minutes.

Preparation 25c. (R)-6-(6-Chloropyridine-3-sulfonyl)-4a-cyclopropylmethoxyoxymethyl-1-(4-fluorophenyl)-1,4,4a,5,6,7,8-hexahydro-1,2,6-triaza-cyclopenta[b]naphthalene The title compound was prepared by the method of Preparation 1c using (R)-4a-cyclopropylmethoxyoxymethyl-1-(4-fluorophenyl)-1,4,4a,5,6,7,8-hexahydro-1,2,6-triaza-cyclopenta[b]naphthalene-6-carboxylic acid tert-butyl ester and 2-chloropyridyl-5-sulfonyl chloride. LCMS (Method G): 529.3/531.2 (chlorine isotope pattern) (M+H)$^+$, Retention time 4.23 minutes.

Preparation 25d. (R)-4a-Cyclopropylmethoxymethyl-1-(4-fluorophenyl)-6-(6-pyrrolidin-1-yl-pyridine-3-sulfonyl)-4,4a,5,6,7,8-hexahydro-1H-1,2,6-triaza-cyclopenta[b]naphthalene The title compound was prepared by the method of Preparation 4b using (R)-6-(6-chloropyridine-3-sulfonyl)-4a-cyclopropyl methoxyoxymethyl-1-(4-fluorophenyl)-1,4,4a,5,6,7,8-hexahydro-1,2,6-triaza-cyclopenta[b]naphthalene and pyrrolidine. $^1$H NMR (400 MHz, CHCl$_3$-d): δ 8.53 (d, 1H), 7.73 (dd, 1H), 7.45-7.35 (m, 3H), 7.14 (t, 2H), 6.36 (d, 1H), 6.26 (s, 1H), 4.15 (d, 1H), 3.87 (t, 1H), 3.59-3.43 (m, 4H), 3.30 (dd, 2H), 3.22-3.12 (m, 2H), 2.72-2.63 (m, 1H), 2.40-2.29 (m, 2H), 2.18 (d, 1H), 2.09-1.99 (m, 4H), 1.02 (d, 1H), 0.50-0.45 (m, 2H), 0.21-0.19 (m, 2H).

Example 26

(R)-4a-Cyclopropylmethoxymethyl-1-(4-fluorophenyl)-6-(6-((R)-3-fluoro-pyrrolidin-1-yl)-pyridine-3-sulfonyl)-4,4a,5,6,7,8-hexahydro-1H-1,2,6-triaza-cyclopenta[b]naphthalene

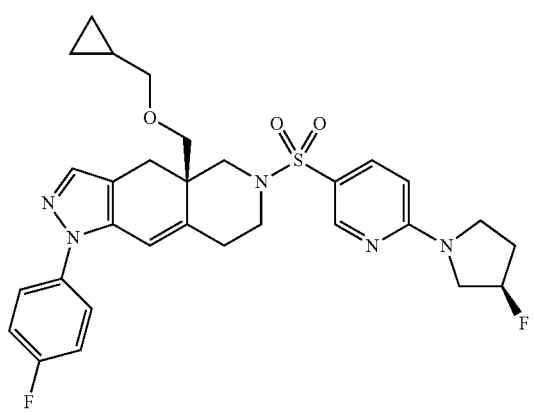 [SMILES: O=S(=O)(c1ccc(N2CC[C@@H](F)C2)nc1)N1CCC2=Cc3c(cnn3-c3ccc(F)cc3)C[C@]2(COCC2CC2)C1]

The title compound was prepared by the method of Example 20 using (R)-6-(6-chloropyridine-3-sulfonyl)-4a-cyclopropyl methoxyoxymethyl-1-(4-fluorophenyl)-1,4,4a,5,6,7,8-hexahydro-1,2,6-triaza-cyclopenta[b]naphthalene, diisopropylethylamine and (R)-3-fluoropyrrolidine hydrochloride. LCMS (Method F): 582 (M+H)$^+$, Retention time 5.5 minutes.

Example 27

(R)-4a-Cyclopropylmethoxymethyl-1-(4-fluorophenyl)-6-(6-((S)-3-fluoropyrrolidin-1-yl)-pyridine-3-sulfonyl)-4,4a,5,6,7,8-hexahydro-1H-1,2,6-triaza-cyclopenta[b]naphthalene

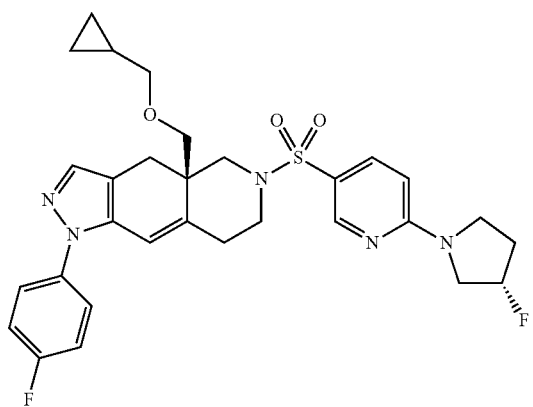 [SMILES: O=S(=O)(c1ccc(N2CC[C@H](F)C2)nc1)N1CCC2=Cc3c(cnn3-c3ccc(F)cc3)C[C@]2(COCC2CC2)C1]

The title compound was prepared by the method of Example 20 using (R)-6-(6-chloropyridine-3-sulfonyl)-4a-cyclopropyl methoxyoxymethyl-1-(4-fluorophenyl)-1,4,4a, 5,6,7,8-hexahydro-1,2,6-triaza-cyclopenta[b]naphthalene, diisopropylethylamine and (S)-3-fluoropyrrolidine hydrochloride. LCMS (Method F): 582 (M+H)+, Retention time 5.5 minutes.

Example 28

(R)-1-{5-[(R)-4a-Cyclopropylmethoxymethyl-1-(4-fluorophenyl)-1,4,4a,5,6,7,8-hexahydro-1,2,6-triaza-cyclopenta[b]naphthalene-6-sulfonyl]pyridine-2-yl}-pyrrolidine-3-ol

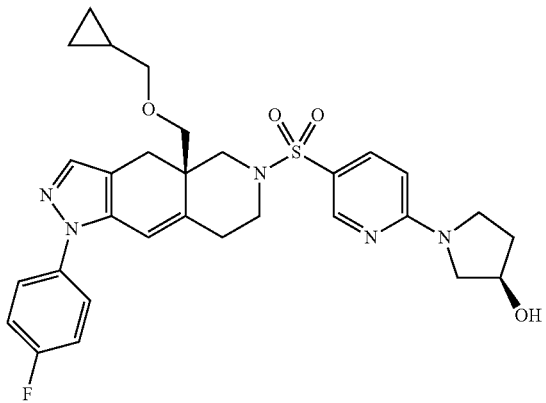 [SMILES: O=S(=O)(c1ccc(N2CC[C@@H](O)C2)nc1)N1CCC2=Cc3c(cnn3-c3ccc(F)cc3)C[C@]2(COCC2CC2)C1]

The title compound was prepared by the method of Example 20 using (R)-6-(6-chloropyridine-3-sulfonyl)-4a-cyclopropyl methoxyoxymethyl-1-(4-fluorophenyl)-1,4,4a,5,6,7,8-hexahydro-1,2,6-triaza-cyclopenta[b]naphthalene, diisopropylethylamine and (R)-3-hydroxypyrrolidine hydrochloride. The title compound was purified by preparative reverse-phase HPLC eluting with a mixture of acetonitrile and water containing 0.1% formic acid (9:11 to 3:1 by volume). LCMS (Method F): 580 (M+H)+, Retention time 4.8 minutes.

Example 29

(S)-1-{5-[(R)-4a-Cyclopropylmethoxymethyl-1-(4-fluorophenyl)-1,4,4a,5,6,7,8-hexahydro-1,2,6-triaza-cyclopenta[b]naphthalene-6-sulfonyl]pyridine-2-yl}-pyrrolidine-3-ol

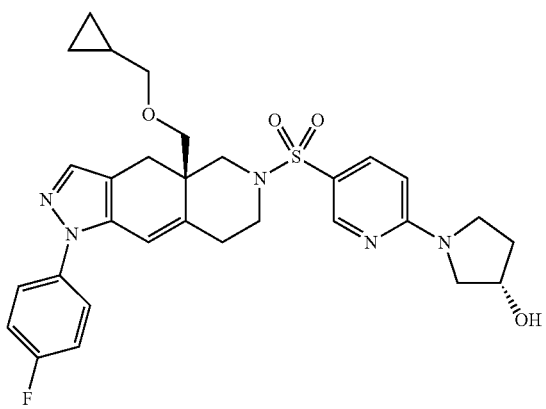 [SMILES: O=S(=O)(c1ccc(N2CC[C@H](O)C2)nc1)N1CCC2=Cc3c(cnn3-c3ccc(F)cc3)C[C@]2(COCC2CC2)C1]

The title compound was prepared by the method of Example 20 using (R)-6-(6-chloropyridine-3-sulfonyl)-4a-cyclopropyl methoxyoxymethyl-1-(4-fluorophenyl)-1,4,4a,5,6,7,8-hexahydro-1,2,6-triaza-cyclopenta[b]naphthalene, diisopropylethylamine and (S)-3-hydroxypyrrolidine hydrochloride. The title compound was purified by preparative reverse-phase HPLC eluting with a mixture of acetonitrile and water containing 0.1% formic acid (9:11 to 3:1 by volume). LCMS (Method F): 580 (M+H)+, Retention time 4.8 minutes.

Example 30

(R)-4a-Cyclopropylmethoxymethyl-6-[6-(3-fluoro-azetin-1-yl)-pyridine-3-sulfonyl]-1-(4-fluorophenyl)-1,4,4a,5,6,7,8-hexahydro-1H-1,2,6-triaza-cyclopenta[b]naphthalene

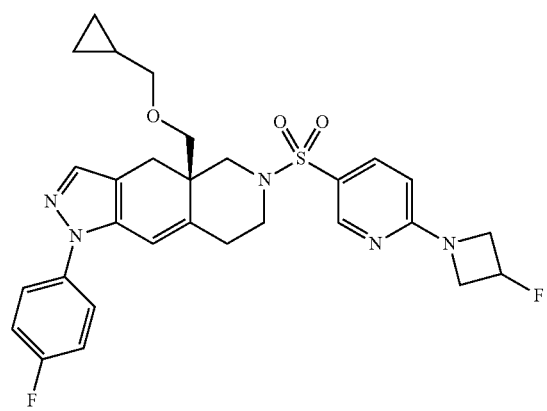 [SMILES: O=S(=O)(c1ccc(N2CC(F)C2)nc1)N1CCC2=Cc3c(cnn3-c3ccc(F)cc3)C[C@]2(COCC2CC2)C1]

The title compound was prepared by the method of Example 20 using (R)-6-(6-chloropyridine-3-sulfonyl)-4a-cyclopropyl methoxyoxymethyl-1-(4-fluorophenye-1,4,4a,5,6,7,8-hexahydro-1,2,6-triaza-cyclopenta[b]naphthalene, diisopropylethylamine and 3-fluoroazetidine hydrochloride. The title compound was purified by preparative reverse-phase HPLC eluting with a mixture of acetonitrile and water containing 0.1% formic acid (3:5 to 9:1 by volume). LCMS (Method F): 568 (M+H)+, Retention time 5.4 minutes.

Example 31

1-{5-[(R)-4a-Cyclopropylmethoxymethyl-1-(4-fluorophenyl)-1,4,4a,5,6,7,8-hexahydro-1,2,6-triaza-cyclopenta[b]naphthalene-6-sulfonyl]-pyridin-2-yl}-azetidin-3-ol

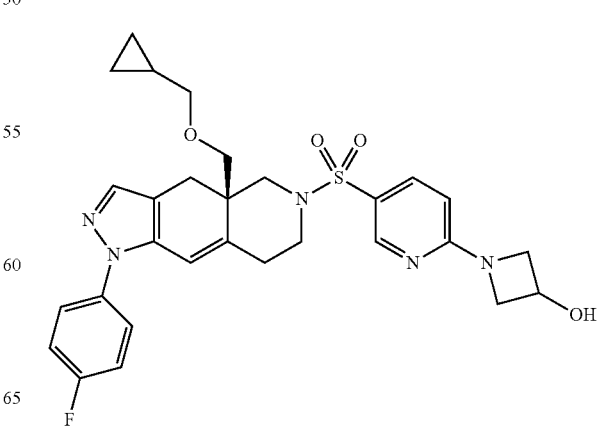

The title compound was prepared by the method of Example 20 using (R)-6-(6-chloropyridine-3-sulfonyl)-4a-cyclopropyl methoxyoxymethyl-1-(4-fluorophenye-1,4,4a,5,6,7,8-hexahydro-1,2,6-triaza-cyclopenta[b]naphthalene, diisopropylethylamine and 3-hydroxyazetidine hydrochloride. The title compound was purified by preparative reverse-phase HPLC eluting with a mixture of acetonitrile and water containing 0.1% formic acid (3:2 to 9:1 by volume). LCMS (Method F): 566 (M+H)+, Retention time 4.7 minutes.

Example 32

(R)-4a-Cyclopropylmethoxymethyl-1-(4-fluorophenyl)-6-(6-morpholin-4-yl-pyridine-3-sulfonyl)-4,4a,5,6,7,8-hexahydro-1H-1,2,6-triaza-cyclopenta[b]naphthalene

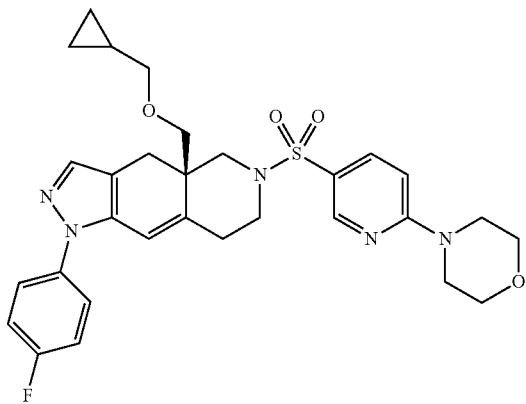 [SMILES: O=S(=O)(c1ccc(N2CCOCC2)nc1)N1CCC2=Cc3c(cnn3-c3ccc(F)cc3)C[C@]2(COCC2CC2)C1]

The title compound was prepared by the method of Preparation 25b using [(R)-1-(4-fluorophenyl)-6-[[6-(4-morpholinyl)-3-pyridinyl]sulfonyl]-1,4,7,8-tetrahydro-1,2,6-triazacyclopenta[b]naphthalen-4a-yl]methanol and cyclopropylmethyl bromide. ¹H NMR (400 MHz, CHCl₃-d): δ 8.54 (d, 1H), 7.80 (dd, 1H), 7.51-7.39 (m, 3H), 7.14 (t, 2H), 6.62 (d, 1H), 4.17 (dd, 1H), 3.80 (t, 4H), 3.65 (t, 4H), 3.45 (d, 1H), 3.30 (dd, 2H), 3.27-3.14 (m, 2H), 2.75-2.65 (m, 1H), 2.43-2.33 (m, 2H), 2.21-2.10 (m, 1H), 2.10 (d, 1H), 1.12-1.01 (m, 1H), 0.49 (dd, 2H), 0.26-0.15 (m, 2H).

Example 33

(R)-1-(4-Fluorophenyl)-6-[6-((R)-3-fluoropyrrolidin-1-yl)-pyridine-3-sulfonyl]-4a-(2-methoxyethoxymethyl)-4,4a,5,6,7,8-hexahydro-1H-1,2,6-triaza-cyclopenta[b]naphthalene

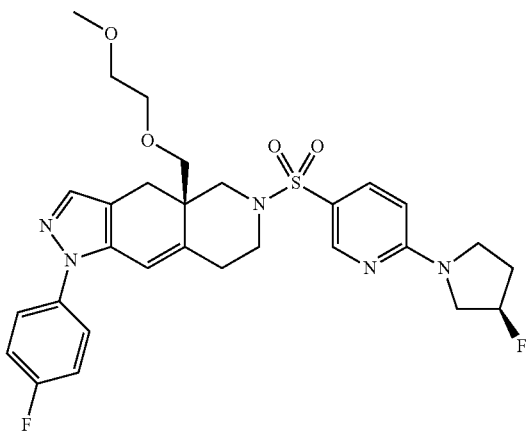 [SMILES: COCCOC[C@]12Cc3cnn(-c4ccc(F)cc4)c3C=C1CCN(S(=O)(=O)c1ccc(N3CC[C@@H](F)C3)nc1)C2]

Preparation 33a. (R)-1-(4-Fluorophenyl)-4a-(2-methoxyethoxymethyl)-1,4,4a,5,6,7,8-hexahydro-1,2,6-triaza-cyclopenta[b]naphthalene-6-carboxylic acid tert-butyl ester The title compound was prepared by the method of Preparation 2b using (R)-1-(4-fluorophenyl)-4a-hydroxymethyl-1,4,4a,5,6,7,8-hexahydro-1,2,6-triaza-cyclopenta[b]naphthalene-6-carboxylic acid tert-butyl ester and 1-iodo-2-methoxyethane. LCMS (Method G): 458.2 (M+H)+, Retention time 4.10 minutes.

Preparation 33b. (R)-6-(6-Chloropyridine-3-sulfonyl)-1-(4-fluorophenyl)-4a-(2-methoxyethoxymethyl)-4,4a,5,6,7,8-hexahydro-1,2,6-triaza-cyclopenta[b]naphthalene The title compound was prepared by the method of Preparation 1c using (R)-1-(4-fluorophenyl)-4a-(2-methoxyethoxymethyl)-1,4,4a,5,6,7,8-hexahydro-1,2,6-triaza-cyclopenta[b]naphthalene-6-carboxylic acid tert-butyl ester and 2-chloropyridyl-5-sulfonyl chloride. LCMS (Method G): 533.3 (M+H)+, Retention time 3.69 minutes.

Preparation 33c. (R)-1-(4-Fluorophenyl)-6-[6-((R)-3-fluoropyrrolidin-1-yl)-pyridine-3-sulfonyl]-4a-(2-methoxyethoxymethyl)-4,4a,5,6,7,8-hexahydro-1H-1,2,6-triaza-cyclopenta[b]naphthalene The title compound was prepared by the method of Example 20 using (R)-6-(6-chloropyridine-3-sulfonyl)-1-(4-fluorophenyl)-4a-(2-methoxyethoxymethyl)-4,4a,5,6,7,8-hexahydro-1,2,6-triaza-cyclopenta[b]naphthalene and (R)-3-fluoropyrrolidine. ¹H NMR (400 MHz, CHCl₃-d): δ 8.55-8.44 (m, 1H), 7.50-7.39 (m, 3H), 7.19-7.11 (m, 2H), 6.41 (d, 1H), 6.27 (d, 1H), 5.46 (s, 1H), 5.33 (s, 1H), 4.15 (dd, 1H), 3.87 (dd, 2H), 3.73 (d, 1H), 3.68-3.55 (m, 7H), 3.38 (s, 3H), 3.25 (d, 1H), 3.14 (d, 1H), 2.80-2.69 (m, 1H), 2.39-2.25 (m, 3H), 2.17-2.03 (m, 3H).

Example 34

2-{(R)-1-(4-Fluorophenyl)-6-[6-((R)-3-fluoropyrrolidin-1-yl)-1,4,5,6,7,8-hexahydro-1,2,6-triaza-cyclopenta[b]naphthalene-4a-ylmethoxy}ethanol

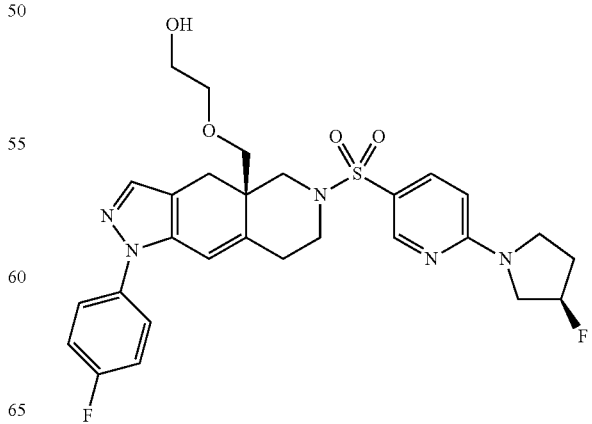

Preparation 34a. (R)-4a-[2-(tert-Butyl-dimethyl-silanyloxy)-ethoxymethyl]-1-(4-fluorophenyl)-1,4,4a,5,6,7,8-hexahydro-1,2,6-triaza-cyclopenta[b]naphthalene-6-carboxylic acid tert-butyl ester The title compound was prepared by the method of Preparation 1e using (R)-1-(4-fluorophenyl)-1,4,4a,5,6,7,8-hexahydro-1,2,6-triaza-cyclopenta[b]naphthalene-6-carboxylic acid tert-butyl ester and (2-bromo-ethoxy)-tert-butyl dimethylsilane. LCMS (Method G): 558.3 (M+H)$^+$, Retention time 5.38 minutes.

Preparation 34b. 2-[(R)-6-(6-Chloropyridine-3-sulfonyl)-1-(4-fluorophenyl)-1,4,5,6,7,8-hexahydro-1,2,6-triaza-cyclopenta[b]naphthalene-4a-ylmethoxy]-ethanol The title compound was prepared by the method of Preparation 1c using (R)-4a-[2-(tert-butyl-dimethyl-silanyloxy)-ethoxymethyl]-1-(4-fluorophenyl)-1,4,4a,5,6,7,8-hexahydro-1,2,6-triaza-cyclopenta[b]naphthalene-6-carboxylic acid tert-butyl ester and 2-chloropyridyl-5-sulfonyl chloride. LCMS (Method G): 519.2 (M+H)$^+$, Retention time 3.47 minutes.

Preparation 34c. 2-{(R)-1-(4-Fluorophenyl)-6-[6-((R)-3-fluoropyrrolidin-1-yl)-pyridine-3-sulphonyl]-1,4,5,6,7,8-hexahydro-1,2,6-triaza-cyclopenta[b]naphthalene-4a-ylmethoxy}-ethanol The title compound was prepared by the method of Example 20 using 2-[(R)-6-(6-chloropyridine-3-sulfonyl)-1-(4-fluorophenyl)-1,4,5,6,7,8-hexahydro-1,2,6-triaza-cyclopenta[b]naphthalene-4a-ylmethoxy]-ethanol and (R)-3-fluoropyrrolidine. $^1$H NMR (400 MHz, CHCl$_3$-d): δ 8.55 (d, 1H), 7.78 (dd, 1H), 7.51-7.40 (m, 3H), 7.15 (t, 2H), 6.41 (d, 1H), 6.28 (s, 1H), 5.40 (d, 1H), 4.26 (d, 1H), 3.91 (s, 2H), 3.74-3.61 (m, 6H), 3.55 (d, 1H), 3.48 (d, 1H), 3.21 (d, 1H), 3.13 (d, 1H), 2.49-2.38 (m, 2H), 2.21 (d, 1H), 2.07 (d, 1H).

Example 35

(R)-1-(4-Fluorophenyl)-6-[6-((R)-3-fluoropyrrolidin-1-yl)-pyridine-3-sulfonyl]-4a-(5-methyl-isoxazol-3-ylmethoxymethyl)-4,4a,5,6,7,8-hexahydro-1H-1,2,6-triaza-cyclopenta[b]naphthalene

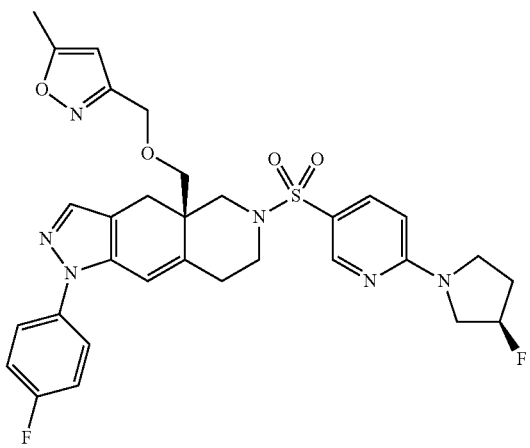 [SMILES: Cc1cc(COC[C@]23Cc4cnn(-c5ccc(F)cc5)c4C=C2CCN(S(=O)(=O)c2ccc(N4CC[C@@H](F)C4)nc2)C3)no1]

Preparation 35a. (R)-1-(4-Fluorophenyl)-4a-(5-methyl-isoxazol-3-ylmethoxymethyl)-1,4,4a,5,6,7,8-hexahydro-1,2,6-triaza-cyclopenta[b]naphthalene-6-carboxylic acid tert-butyl ester The title compound was prepared by the method of Preparation 1e using (R)-1-(4-fluorophenyl)-1,4,4a,5,6,7,8-hexahydro-1,2,6-triaza-cyclopenta[b]naphthalene-6-carboxylic acid tert-butyl ester and 3-bromomethyl-5-methylisoxazole. LCMS (Method G): 495 (M+H)$^+$, Retention time 4.02 minutes.

Preparation 35b. (R)-6-(6-Chloropyridine-3-sulfonyl)-1-(4-fluorophenyl)-4a-(5-methyl-isoxazol-3-ylmethoxymethyl)-4,4a,5,6,7,8-hexahydro-1H-1,2,6-triaza-cyclopenta[b]naphthalene The title compound was prepared by the method of Preparation 1c using (R)-1-(4-fluorophenyl)-4a-(5-methyl-isoxazol-3-ylmethoxymethyl)-1,4,4a,5,6,7,8-hexahydro-1,2,6-triaza-cyclopenta[b]naphthalene-6-carboxylic acid tert-butyl ester and 2-chloropyridyl-5-sulfonyl chloride. LCMS (Method G): 570.1 (M+H)$^+$, Retention time 3.82 minutes.

Preparation 35c. (R)-1-(4-Fluorophenyl)-6-[6-((R)-3-fluoropyrrolidin-1-yl)-pyridine-3-sulfonyl]-4a-(5-methyl-isoxazol-3-ylmethoxymethyl)-4,4a,5,6,7,8-hexahydro-1H-1,2,6-triaza-cyclopenta[b]naphthalene The title compound was prepared by the method of Example 20 using (R)-6-(6-chloropyridine-3-sulfonyl)-1-(4-fluorophenyl)-4a-(5-methyl-isoxazol-3-ylmethoxymethyl)-4,4a,5,6,7,8-hexahydro-1H-1,2,6-triaza-cyclopenta[b]naphthalene and (R)-3-fluoropyrrolidine. $^1$H NMR (400 MHz, CHCl$_3$-d): δ 8.55 (d, 1H), 7.77 (dd, 1H), 7.49-7.37 (m, 3H), 7.14 (t, 2H), 6.41 (d, 1H), 6.35-6.20 (m, 2H), 5.40 (d, 1H), 4.62-4.48 (m, 2H), 4.19 (dd, 1H), 3.78-3.70 (m, 3H), 3.51 (d, 1H), 3.18-3.10 (m, 2H), 2.69-2.60 (m, 1H), 2.42 (d, 3H), 2.21 (d, 1H), 2.10 (d, 1H).

Example 36

1-{5-[(R)-1-(4-Fluorophenyl)-4a-methoxymethyl-1,4,4a,5,6,7,8-hexahydro-1,2,6-triaza-cyclopenta[b]naphthalene-6-sulfonyl]-pyridin-3-yl}-azetidin-3-ol

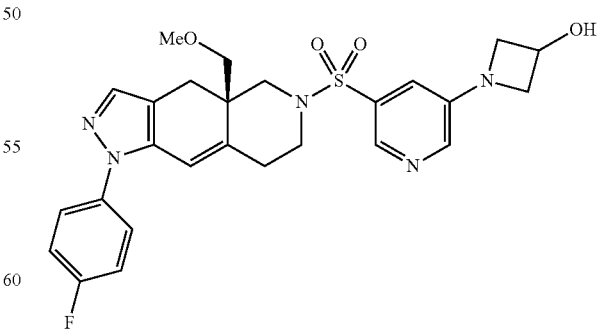

The title compound was prepared by the method of Preparation 12c using (R)-6-(5-bromopyridine-3-sulfonyl)-1-(4-fluorophenyl)-4a-methoxymethyl-4,4a,5,6,7,8-hexahydro-1H-1,2,6-triazacyclopenta[b]naphthalene and 3-hydroxyazetidine hydrochloride. LCMS (Method F): 526 (M+H)+, Retention time 4.2 minutes.

Example 37

(R)-6-[5-(3-Fluoroazetidin-1-yl)-pyridine-3-sulfonyl]-1-(4-fluorophenyl)-4a-methoxymethyl-4,4a,5,6,7,8-hexahydro-1H-1,2,6-triaza-cyclopenta[b]naphthalene

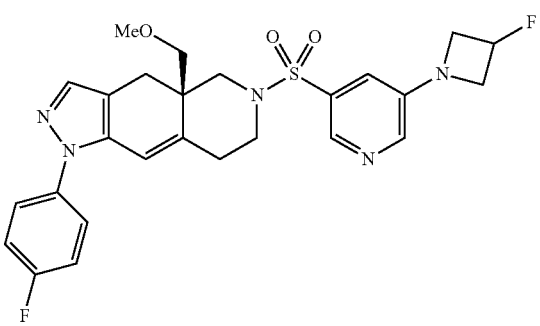 [SMILES: COC[C@]12Cc3cnn(-c4ccc(F)cc4)c3C=C1CCN(S(=O)(=O)c1cncc(N3CC(F)C3)c1)C2]

The title compound was prepared by the method of Preparation 12c using (R)-6-(5-bromopyridine-3-sulfonyl)-1-(4-fluorophenyl)-4a-methoxymethyl-4,4a,5,6,7,8-hexahydro-1H-1,2,6-triazacyclopenta[b]naphthalene and 3-hydroxyazetidine hydrochloride. LCMS (Method F): 528 (M+H)+, Retention time 4.9 minutes.

Example 38

(R)-1-{5-[(R)-1-(4-Fluorophenyl)-4a-methoxymethyl-1,4,4a,5,6,7,8-hexahydro-1,2,6-triaza-cyclopenta[b]naphthalene-6-sulfonyl]pyridine-3-yl}-pyrrolidine-3-ol

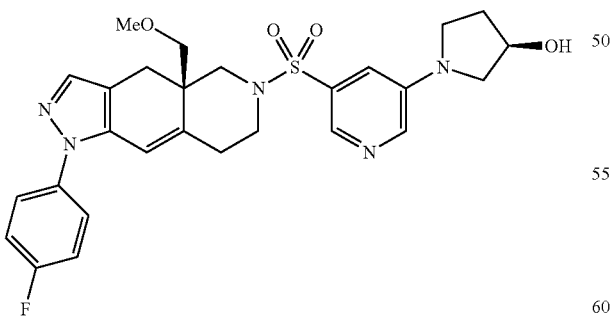

The title compound was prepared by the method of Preparation 12c using (R)-6-(5-bromopyridine-3-sulfonyl)-1-(4-fluorophenyl)-4a-methoxymethyl-4,4a,5,6,7,8-hexahydro-1H-1,2,6-triazacyclopenta[b]naphthalene and (R)-3-hydroxypyrrolidine hydrochloride. LCMS (Method F): 540 (M+H)+, Retention time 4.2 minutes.

Example 39

(S)-1-{5-[(R)-1-(4-Fluorophenyl)-4a-methoxymethyl-1,4,4a,5,6,7,8-hexahydro-1,2,6-triaza-cyclopenta[b]naphthalene-6-sulfonyl]pyridine-3-yl}-pyrrolidine-3-ol

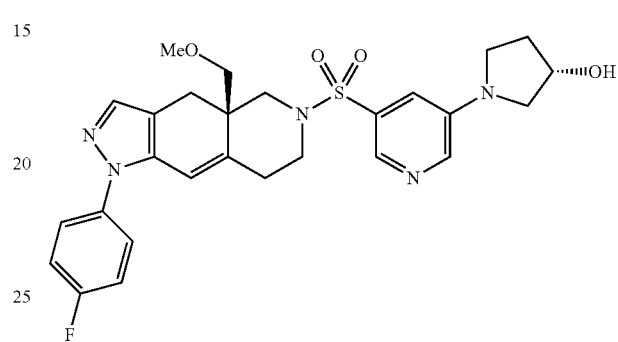

The title compound was prepared by the method of Preparation 12c using (R)-6-(5-bromopyridine-3-sulfonyl)-1-(4-fluorophenyl)-4a-methoxymethyl-4,4a,5,6,7,8-hexahydro-1H-1,2,6-triazacyclopenta[b]naphthalene and (S)-3-hydroxypyrrolidine hydrochloride. LCMS (Method F): 540 (M+H)+, Retention time 4.2 minutes.

Example 40

(R)-1-(4-Fluorophenyl)-6-[5-((R)-3-fluoropyrrolidin-1-yl)-pyridine-3-sulfonyl]-4a-methoxymethyl-4,4a,5,6,7,8-hexahydro-1H-1,2,6-triaza-cyclopenta[b]naphthalene

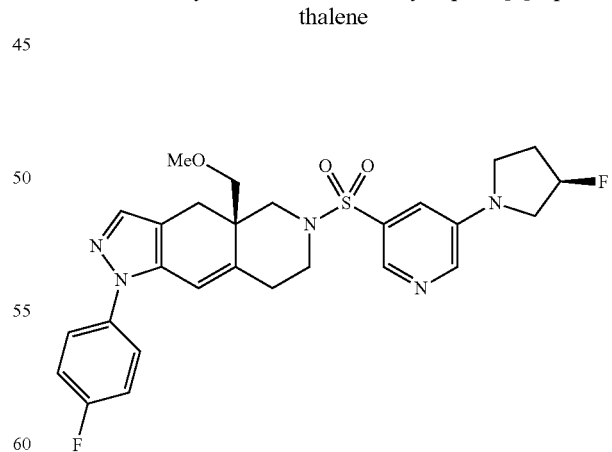

The title compound was prepared by the method of Preparation 12c using (R)-6-(5-bromopyridine-3-sulfonyl)-1-(4-fluorophenyl)-4a-methoxymethyl-4,4a,5,6,7,8-hexahydro-1H-1,2,6-triazacyclopenta[b]naphthalene and (R)-3- fluoropyrrolidine hydrochloride. LCMS (Method F): 542 (M+H)⁺, Retention time 4.9 minutes.

Example 41

(R)-1-(4-Fluorophenyl)-6-[5-((S)-3-fluoropyrrolidin-1-yl)-pyridine-3-sulfonyl]-4a-methoxymethyl-4,4a,5,6,7,8-hexahydro-1H-1,2,6-triaza-cyclopenta[b]naphthalene

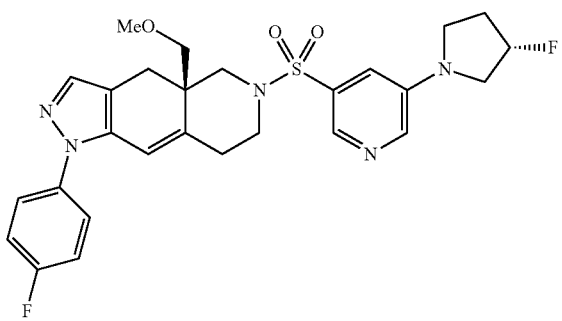 [SMILES: COC[C@]12Cc3cnn(-c4ccc(F)cc4)c3C=C1CCN(S(=O)(=O)c1cncc(N3CC[C@H](F)C3)c1)C2]

The title compound was prepared by the method of Preparation 12c using (R)-6-(5-bromopyridine-3-sulfonyl)-1-(4-fluorophenyl)-4a-methoxymethyl-4,4a,5,6,7,8-hexahydro-1H-1,2,6-triazacyclopenta[b]naphthalene and (S)-3-fluoropyrrolidine hydrochloride. LCMS (Method F): 542 (M+H)⁺, Retention time 4.9 minutes.

Example 42

(R)-1-(4-Fluorophenyl)-4a-methoxymethyl-6-(2-pyrrolidin-1-yl-pyridine-4-sulfonyl)-4,4a,5,6,7,8-hexahydro-1H-1,2,6-triaza-cyclopenta[b]naphthalene

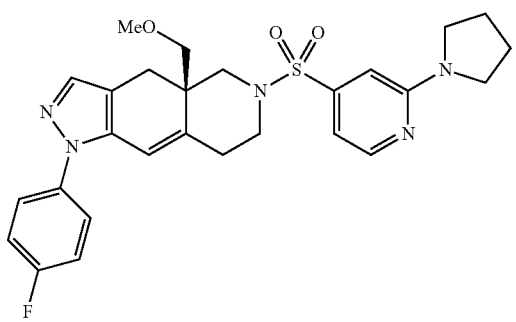 [SMILES: COC[C@]12Cc3cnn(-c4ccc(F)cc4)c3C=C1CCN(S(=O)(=O)c1ccnc(N3CCCC3)c1)C2]

Preparation 42a. 2-Chloropyridine-4-sulfonyl chloride

A solution of 4-amino-2-chloropyridine (1.29 g) in trifluoroacetic acid (10 mL) and concentrated hydrochloric acid (5 mL) at 4° C. was treated with a solution of sodium nitrite (2.07 g) in water (7.5 mL) and stirred at 0° C. for 1 hour where some precipitation occurred. The precipitate was removed by filtration into a pre-cooled (−15° C.) round-bottomed flask. The cooled filtrate was added dropwise to a pre-cooled (0° C.) suspension of copper (I) chloride (0.1 g) and copper (II) chloride (0.67 g) in acetic acid containing dissolved sulphur dioxide (60 mL) (prepared by bubbling sulphur dioxide gas through glacial acetic acid at room temperature for 30 minutes: approximately 28 g of sulphur dioxide dissolves in 100 g glacial acetic acid). The reaction mixture was stirred at 0° C. for 1.5 hours. The reaction mixture was diluted with dichloromethane, extracted with ice-water, saturated sodium hydrogen carbonate solution and brine. The organic extracts were dried over sodium sulfate and filtered to remove solids. The filtrate was concentrated under reduced pressure to provide a yellow-brown oil. The material obtained was used immediately without further purification.

Preparation 42b. (R)-1-(4-Fluorophenyl)-4a-methoxymethyl-1,4,4a,5,6,7,8-hexahydro-1,2,6-triaza-cyclopenta[b]naphthalene-6-carboxylic acid tert-butyl ester The title compound was prepared by the method of Preparation 2b using (R)-1-(4-fluorophenye-4a-hydroxymethyl-1,4,4a,5,6,7,8-hexahydro-1,2,6-triaza-cyclopenta[b]naphthalene-6-carboxylic acid tert-butyl ester and iodomethane. LCMS (Method G): 414.2 (M+H)⁺, Retention time 4.12 minutes.

Preparation 42c. (R)-6-(2-Chloropyridine-4-sulfonyl)-1-(4-fluorophenyl)-4a-methoxymethyl-4,4a,5,6,7,8-hexahydro-1H-1,2,6-triaza-cyclopenta[b]naphthalene The title compound was prepared by the method of Preparation 1c using (R)-1-(4-fluorophenyl)-4a-methoxymethyl-1,4,4a,5,6,7,8-hexahydro-1,2,6-triaza-cyclopenta[b]naphthalene-6-carboxylic acid tert-butyl ester and 2-chloropyridine-4-sulfonyl chloride. LCMS (Method G): 490.1 (M+H)⁺, Retention time 3.90 minutes.

Preparation 42d. (R)-1-(4-Fluorophenyl)-4a-methoxymethyl-6-(2-pyrrolidin-1-yl-pyridine-4-sulfonyl)-4,4a,5,6,7,8-hexahydro-1H-1,2,6-triaza-cyclopenta[b]naphthalene The title compound was prepared by the method of Preparation 4b using (R)-6-(2-chloropyridine-4-sulfonyl)-1-(4-fluorophenyl)-4a-methoxymethyl-4,4a,5,6,7,8-hexahydro-1H-1,2,6-triaza-cyclopenta[b]naphthalene and pyrrolidine. ¹H NMR (400 MHz, CHCl₃-d): δ 8.30 (d, 1H), 7.44-7.36 (m, 3H), 7.15 (t, 2H), 6.76 (dd, 1H), 6.65 (s, 1H), 6.29 (d, 1H), 4.24-4.13 (m, 1H), 3.91 (dd, 1H), 3.49 (t, 4H), 3.36 (s, 4H), 3.16-3.07 (m, 2H), 2.78-2.68 (m, 1H), 2.59-2.51 (m, 1H), 2.38 (d, 1H), 2.28-2.20 (m, 2H), 2.05 (t, 4H).

Example 43

(R)-1-{4-[(R)-1-(4-Fluorophenyl)-4a-methoxymethyl-1,4,4a,5,6,7,8-hexahydro-1,2,6-triaza-cyclopenta[b]naphthalene-6-sulfonyl]-pyridin-2-yl}-pyrrolidin-3-ol

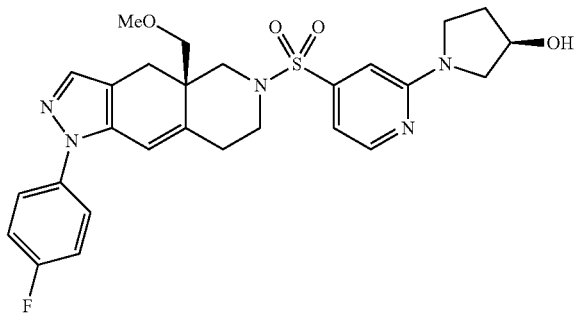 [SMILES: COC[C@]12Cc3cnn(-c4ccc(F)cc4)c3C=C1CCN(S(=O)(=O)c1ccnc(N3CC[C@@H](O)C3)c1)C2]

The title compound was prepared by the method of Preparation 4b using (R)-6-(2-chloropyridine-4-sulfonyl)-1-(4-fluorophenyl)-4a-methoxymethyl-4,4a,5,6,7,8-hexahydro-1H-1,2,6-triaza-cyclopenta[b]naphthalene and pyrrolidine cyclopenta[b]naphthalene and (R)-3-hydroxypyrrolidine hydrochloride. LCMS (Method F): 540 (M+H)$^+$, Retention time 4.0 minutes.

Example 44

(S)-1-{4-[(R)-1-(4-Fluorophenyl)-4a-methoxymethyl-1,4,4a,5,6,7,8-hexahydro-1,2,6-triaza-cyclopenta[b]naphthalene-6-sulfonyl]-pyridin-2-yl}-pyrrolidin-3-ol

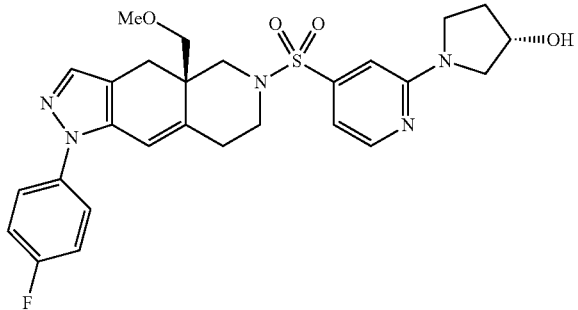 [SMILES: COC[C@]12Cc3cnn(-c4ccc(F)cc4)c3C=C1CCN(S(=O)(=O)c1ccnc(N3CC[C@H](O)C3)c1)C2]

The title compound was prepared by the method of Preparation 4b using (R)-6-(2-chloropyridine-4-sulfonyl)-1-(4-fluorophenyl)-4a-methoxymethyl-4,4a,5,6,7,8-hexahydro-1H-1,2,6-triaza-cyclopenta[b]naphthalene and pyrrolidine cyclopenta[b]naphthalene and (R)-3-hydroxypyrrolidine hydrochloride. LCMS (Method F): 540 (M+H)$^+$, Retention time 4.0 minutes.

Example 45

2-{[(S)-1-(4-Fluorophenyl)-6-[6-morpholin-4-yl-pyridine-3-sulfonyl)-1,4,5,6,7,8-hexahydro-1,2,6-triaza-cyclopenta[b]naphthalene-4a-ylmethyl]-methyl-amino}-ethanol

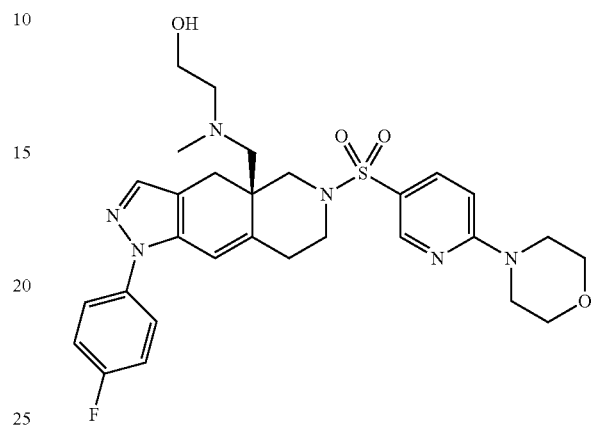

The title compound was prepared by the method of Preparation 62 using (R)-1-(4-fluorophenyl)-6-[6-morpholin-4-yl-pyridine-3-sulfonyl)-1,4,5,6,7,8-hexahydro-1,2,6-triaza-cyclopenta[b]naphthalene-4a-carbaldehyde and 2-methylamino ethanol. LCMS (Method F): 583 (M+H)$^+$, Retention time 3.2 minutes.

Example 46

(S)-1-{(S)-1-(4-Fluorophenyl)-6-[6-((R)-3-hydroxy-pyrrolidin-3-ol)-pyridine-3-sulfonyl]-1,4,5,6,7,8-hexahydro-1,2,6-triaza-cyclopenta[b]naphthalene-4a-ylmethyl}-pyrrolidin-3-ol

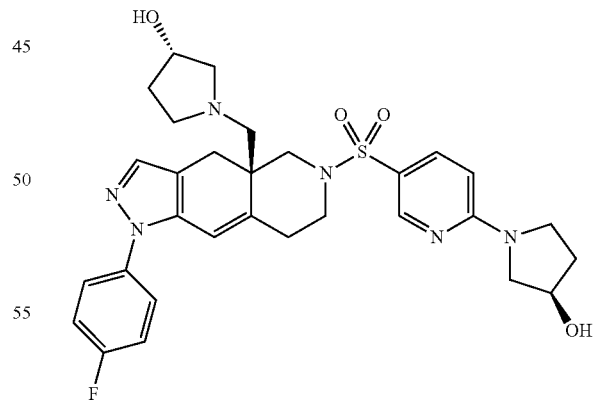

Preparation 46a. (R)-1-(4-Fluorophenyl)-4a-formyl-1,4,4a,5,6,7,8-hexahydro-1,2,6-triaza-cyclopenta[b]naphthalene-6-carboxylic acid tert-butyl ester A solution of oxalyl chloride (0.28 g) in dichloromethane at −70° C. was treated with dimethylsulphoxide (0.37 g) in dichloromethane (3 mL) for 15 minutes. The reaction mixture was allowed to warm to −18° C. and then treated with a solution of (R)-1-(4-fluorophenyl)-4a-hydroxymethyl-1,4,4a,5,6,7,8-hexahydro-1,2,6-triaza-cyclopenta[b]naphthalene-6-carboxylic acid tert-butyl ester (0.51 g) in dichloromethane (5 mL). The reaction mixture was stirred at −18° C. for 45 minutes. Triethylamine (0.51 g) was added and the reaction mixture stirred at room temperature for 30 minutes. The reaction mixture was washed with water, dried over sodium sulfate and concentrated under reduced pressure. The residue was purified by column chromatography on silica gel, eluting with ethyl acetate in cyclohexane (0 to 1 by volume) to give the title compound (0.42 g) $^1$H NMR (300 MHz, CHCl$_3$-d): δ 9.47 (s, 1H), 7.54-7.43 (m, 3H), 7.18 (t, 2H), 6.51 (s, 1H), 3.21 (d, 1H), 2.87 (s, 3H), 2.64 (d, 2H), 2.48 (s, 1H), 1.45 (d, 9H).

Preparation 46b. (S)-1-(4-Fluorophenyl)-4a-((S)-3-hydroxy-pyrrolidin-1-ylmethyl)-1,4,4a,5,6,7,8-hexahydro-1,2,6-triaza-cyclopenta[b]naphthalene-6-carboxylic acid tert-butyl ester The title compound was prepared by the method of Preparation 62 using (R)-1-(4-fluorophenyl)-4a-formyl-1,4,4a,5,6,7,8-hexahydro-1,2,6-triaza-cyclopenta[b]naphthalene-6-carboxylic acid tert-butyl ester and (S)-pyrrolidin-3-ol. LCMS (Method G): 468.1 (M+H)$^+$, Retention time 2.5 minutes.

Preparation 46c. (S)-1-[(S)-6-(6-Chloropyridine-3-sulfonyl)-1-(4-fluorophenyl)-1,4,5,6,7,8-hexahydro-1,2,6-triaza-cyclopenta[b]naphthalene-4a-ylmethyl]-pyrrolidin-3-ol The title compound was prepared by the method of Preparation 1c using (S)-1-(4-fluorophenyl)-4a-((S)-3-hydroxy-pyrrolidin-1-ylmethyl)-1,4,4a,5,6,7,8-hexahydro-1,2,6-triaza-cyclopenta[b]naphthalene-6-carboxylic acid tert-butyl ester and 2-chloropyridyl-5-sulfonyl chloride. LCMS (Method G): 544.1 (M+H)$^+$, Retention time 2.42 minutes.

Preparation 46d. (S)-1-{(S)-1-(4-Fluorophenyl)-6-[6-((R)-3-hydroxy-pyrrolidin-3-ol)-pyridine-3-sulfonyl]-1,4,5,6,7,8-hexahydro-1,2,6-triaza-cyclopenta[b]naphthalene-4a-ylmethyl}-pyrrolidin-3-ol The title compound was prepared by the method of Example 20 using (S)-1-[(S)-6-(6-chloropyridine-3-sulfonyl)-1-(4-fluorophenyl)-1,4,5,6,7,8-hexahydro-1,2,6-triaza-cyclopenta[b]naphthalene-4a-ylmethyl]-pyrrolidin-3-ol and (R)-3-pyrrolidinol. $^1$H NMR (400 MHz, CHCl$_3$-d): δ 8.52 (d, 1H), 8.33 (s, 1H), 7.75 (dd, 1H), 7.54-7.42 (m, 2H), 7.16 (t, 2H), 6.40 (d, 1H), 6.30 (d, 1H), 4.64 (s, 1H), 4.50 (s, 4H), 4.42 (s, 1H), 4.27 (d, 1H), 3.90 (t, 1H), 3.65 (s, 3H), 3.40 (q, 1H), 3.32 (d, 1H), 3.17-3.03 (m, 3H), 2.88-2.70 (m, 1H), 2.69-2.59 (m, 2H), 2.45-2.30 (m, 3H), 2.22-2.10 (m, 3H), 1.98-1.90 (m, 1H).

Example 47

(S)-1-{(S)-1-(4-Fluorophenyl)-6-[6-((R)-3-fluoro-pyrrolidin-1-yl)-pyridine-3-sulfonyl]-1,4,5,6,7,8-hexahydro-1,2,6-triaza-cyclopenta[b]naphthalene-4a-ylmethyl}-pyrrolidin-3-ol

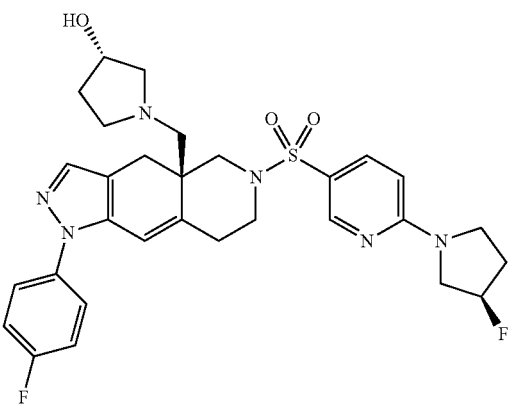 [SMILES: O=S(=O)(c1ccc(N2CC[C@@H](F)C2)nc1)N1CCC2=Cc3c(cnn3-c3ccc(F)cc3)C[C@]2(CN2CC[C@H](O)C2)C1]

The title compound was prepared by the method of Example 20 using (S)-1-[(S)-6-(6-chloropyridine-3-sulfonyl)-1-(4-fluorophenyl)-1,4,5,6,7,8-hexahydro-1,2,6-triaza-cyclopenta[b]naphthalene-4a-ylmethyl]-pyrrolidin-3-ol and (R)-3-fluoropyrrolidine. LCMS (Method G): 597 (M+H)$^+$, Retention time 3.30 minutes.

Example 48

(R)-1-(4-Fluorophenyl)-6-(6-morpholin-4-yl-pyridine-3-sulfonyl)-1,4,5,6,7,8-hexahydro-1,2,6-triaza-cyclopenta[b]naphthalene-4a-carboxylic acid ethyl ester

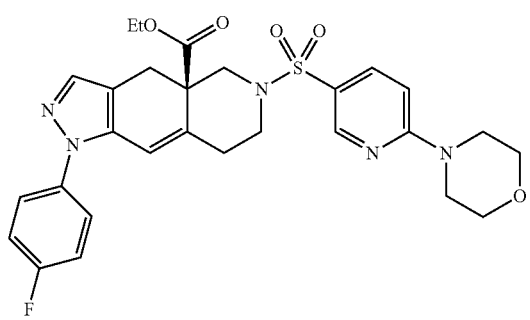 [SMILES: CCOC(=O)[C@]12Cc3cnn(-c4ccc(F)cc4)c3C=C1CCN(S(=O)(=O)c1ccc(N3CCOCC3)nc1)C2]

Preparation 48a. (R)-1-(4-Fluorophenyl)-6-(6-morpholin-4-yl-pyridine-3-sulfonyl)-1,4,5,6,7,8-hexahydro-1,2,6-triaza-cyclopenta[b]naphthalene-4a-carboxylic acid A solution of (R)-1-(4-fluorophenyl)-6-(6-morpholin-4-yl-pyridine-3-sulfonyl)-1,4,5,6,7,8-hexahydro-1,2,6-triaza-cyclopenta[b]naphthalene-4a-carboxylic acid methyl ester (0.3 g) in tetrahydrofuran (10 mL) and water (10 mL) was treated with lithium hydroxide monohydrate (0.11 g) at 60° C. for 16 hours. The cooled mixture was diluted with ethyl acetate and 1.0 M aqueous hydrochloric acid solution. The aqueous phase was washed with ethyl acetate, the combined organic phases were washed with brine and dried over sodium sulfate. The solvent was removed under reduced pressure to afford the title compound as a foam (0.3 g). LCMS (Method G): 540.4 (M+H)+, Retention time 3.16 minutes.

Preparation 48b. (R)-1-(4-Fluorophenyl)-6-(6-morpholin-4-yl-pyridine-3-sulfonyl]-1,4,5,6,7,8-hexahydro-1,2,6-triaza-cyclopenta[b]naphthalene-4a-carbonyl chloride A solution of (R)-1-(4-fluorophenyl)-6-(6-morpholin-4-yl-pyridine-3-sulfonyl]-1,4,5,6,7,8-hexahydro-1,2,6-triaza-cyclopenta[b]naphthalene-4a-carboxylic acid (0.29 g) in dry dichloromethane (9 mL) was treated with oxalyl chloride (0.21 g) for 30 minutes. One drop of N,N-dimethylformamide was added and the reaction mixture stirred for a further 2 hours. The reaction mixture was concentrated under reduced pressure and the product used without further purification.

Preparation 48c. (R)-1-(4-Fluorophenyl)-6-(6-morpholin-4-yl-pyridine-3-sulfonyl]-1,4,5,6,7,8-hexahydro-1,2,6-triaza-cyclopenta[b]naphthalene-4a-carboxylic acid ethyl ester A solution of (R)-1-(4-fluorophenyl)-6-(6-morpholin-4-yl-pyridine-3-sulfonyl]-1,4,5,6,7,8-hexahydro-1,2,6-triaza-cyclopenta[b]naphthalene-4a-carbonyl chloride (0.1 g) in dry dichloromethane (5 mL) was treated with absolute ethanol (0.2 g) and triethylamine (0.1 g) for 16 hours. The reaction mixture was concentrated under reduced pressure and the residue purified by column chromatography on silica gel, eluting with ethyl acetate in cyclohexane (1:4 to 2:3 by volume) to afford the title compound as a white solid (0.057 g). $^1$H NMR (400 MHz, CHCl$_3$-d): δ 8.53 (d, 1H), 7.77 (dd, 1H), 7.48-7.36 (m, 3H), 7.19-7.11 (m, 2H), 6.61 (d, 1H), 6.40 (d, 1H), 4.37 (d, 1H), 4.17 (qd, 2H), 3.80 (t, 5H), 3.66 (t, 4H), 3.29 (d, 1H), 2.95-2.86 (m, 1H), 2.57 (d, 1H), 2.44-2.34 (m, 3H), 1.25 (t, 3H).

Example 49

(R)-1-(4-Fluorophenyl)-6-(6-morpholin-4-yl-pyridine-3-sulfonyl]-1,4,5,6,7,8-hexahydro-1,2,6-triaza-cyclopenta[b]naphthalene-4a-carboxylic acid isopropyl ester

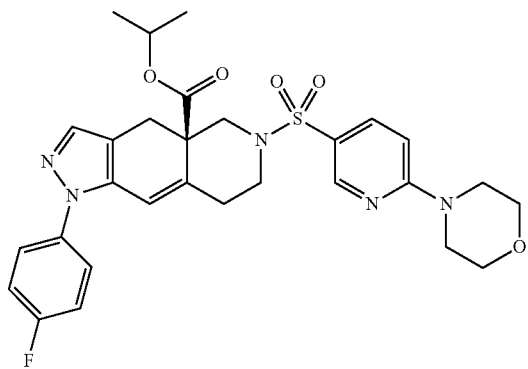 [SMILES: CC(C)OC(=O)[C@]12Cc3cnn(-c4ccc(F)cc4)c3C=C1CCN(S(=O)(=O)c1ccc(N3CCOCC3)nc1)C2]

The title compound was prepared by the method of Preparation 48c using (R)-1-(4-fluorophenyl)-6-(6-morpholin-4-yl-pyridine-3-sulfonyl]-1,4,5,6,7,8-hexahydro-1,2,6-triaza-cyclopenta[b]naphthalene-4a-carbonyl chloride and propan-2-ol. LCMS (Method F): 582 (M+H)+, Retention time 5.1 minutes.

Example 50

(R)-1-(4-Fluorophenyl)-6-(6-morpholin-4-yl-pyridine-3-sulfonyl]-1,4,5,6,7,8-hexahydro-1,2,6-triaza-cyclopenta[b]naphthalene-4a-carboxylic acid cyclobutyl ester

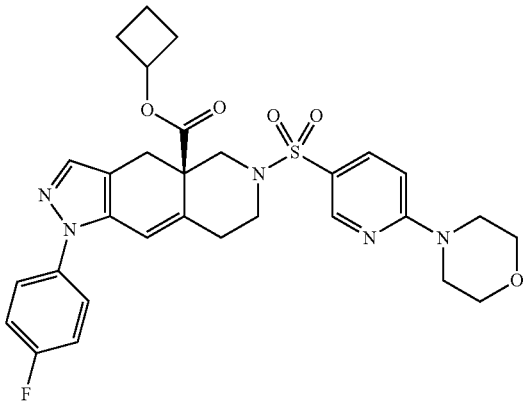 [SMILES: O=C(OC1CCC1)[C@]12Cc3cnn(-c4ccc(F)cc4)c3C=C1CCN(S(=O)(=O)c1ccc(N3CCOCC3)nc1)C2]

Preparation 50a. (R)-1-(4-Fluorophenyl)-6-(6-morpholin-4-yl-pyridine-3-sulfonyl]-1,4,5,6,7,8-hexahydro-1,2,6-triaza-cyclopenta[b]naphthalene-4a-carboxylic acid cyclobutyl ester (R)-1-(4-Fluorophenyl)-6-(6-morpholin-4-yl-pyridine-3-sulfonyl]-1,4,5,6,7,8-hexahydro-1,2,6-triaza-cyclopenta[b]naphthalene-4a-carbonyl chloride (0.12 g), triethylamine (0.11 g) and cyclobutanol (0.24 g) were heated in a microwave apparatus at 110° C. for 3 hours. The reaction mixture was concentrated under reduced pressure and the residue purified by column chromatography on silica gel, eluting with ethyl acetate in dichloromethane (1:4 to 2:3 by volume) followed by preparative reverse-phase HPLC eluting with a mixture of acetonitrile and water containing 0.1% formic acid (1:1 to 4:1 by volume) to give the title compound as a white solid (0.023 g). $^1$H NMR (400 MHz, CHCl$_3$-d): δ 8.53 (d, 1H), 7.78 (dd, 1H), 7.47-7.35 (m, 3H), 7.19-7.11 (m, 2H), 6.62 (d, 1H), 6.40 (d, 1H), 4.95 (t, 1H), 4.38 (dd, 1H), 3.81 (t, 5H), 3.66 (t, 4H), 3.29 (d, 1H), 2.99-2.90 (m, 1H), 2.57 (d, 1H), 2.48-2.28 (m, 5H), 2.16-2.05 (m, 2H), 1.87-1.77 (m, 1H), 1.66-1.52 (m, 1H).

Example 51

(R)-1-(4-Fluorophenyl)-6-(6-morpholin-4-yl-pyridine-3-sulfonyl]-1,4,5,6,7,8-hexahydro-1,2,6-triaza-cyclopenta[b]naphthalene-4a-carboxylic acid cyclopropylmethyl ester

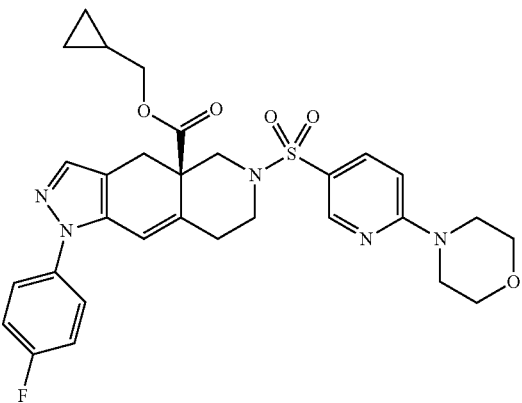 [SMILES: O=C(OCC1CC1)[C@]12Cc3cnn(-c4ccc(F)cc4)c3C=C1CCN(S(=O)(=O)c1ccc(N3CCOCC3)nc1)C2]

Preparation 51a. (R)-1-(4-Fluorophenyl)-1,4,7,8-hexahydro-1,2,6-triaza-cyclopenta[b]naphthalene-4a,6-dicarboxylic acid 6-tert-butyl ester The title compound was prepared by the method of Preparation 48a using (R)-1-(4-fluorophenyl)-1,4,7,8-hexahydro-1,2,6-triaza-cyclopenta[b]naphthalene-4a,6-dicarboxylic acid 6-tert-butyl ester 4a-methyl ester. LCMS (Method G): 414.2 (M+H)$^+$, Retention time 3.4 minutes.

Preparation 51b. (R)-1-(4-Fluorophenyl)-1,4,7,8-hexahydro-1,2,6-triaza-cyclopenta[b]naphthalene-4a,6-dicarboxylic acid 6-tert-butyl ester 4a-cyclopropylmethyl ester A solution of (R)-1-(4-fluorophenyl)-1,4,7,8-hexahydro-1,2,6-triaza-cyclopenta[b]naphthalene-4a,6-dicarboxylic acid 6-tert-butyl ester (0.1 g) in N,N-dimethylformamide was treated with cesium carbonate (0.16 g) and cyclopropylmethyl bromide (0.16 g) at room temperature for 16 hours. The reaction mixture was diluted with water and extracted with ethyl acetate. The organic phase was washed with brine, dried over sodium sulfate and concentrated under reduced pressure. The residue was purified by column chromatography on silica gel, eluting with ethyl acetate in dichloromethane (1:19 to 1:9 by volume) to give the title compound (0.1 g). LCMS (Method G): 468.6 (M+H)$^+$, Retention time 4.5 minutes.

Preparation 51c. (R)-6-(6-Chloropyridine-3-sulfonyl)-1-(4-fluorophenyl)-1,4,5,6,7,8-hexahydro-1,2,6-triaza-cyclopenta[b]naphthalene-4a-carboxylic acid cyclopropylmethyl ester The title compound was prepared by the method of Preparation 1c using (R)-1-(4-fluorophenyl)-1,4,7,8-hexahydro-1,2,6-triaza-cyclopenta[b]naphthalene-4a,6-dicarboxylic acid 6-tert-butyl ester 4a-cyclopropylmethyl ester and 2-chloropyridyl-5-sulfonyl chloride to give the title compound (0.11 g). LCMS (Method G): 543.0 (M+H)$^+$, Retention time 4.0 minutes.

Preparation 51d. (R)-1-(4-Fluorophenyl)-6-(6-morpholin-4-yl-pyridine-3-sulfonyl]-1,4,5,6,7,8-hexahydro-1,2,6-triaza-cyclopenta[b]naphthalene-4a-carboxylic acid cyclopropylmethyl ester The title compound was prepared by the method of Example 20 using (R)-6-(6-chloropyridine-3-sulfonyl)-1-(4-fluorophenyl)-1,4,5,6,7,8-hexahydro-1,2,6-triaza-cyclopenta[b]naphthalene-4a-carboxylic acid cyclopropylmethyl ester and morpholine to give the title compound (0.063 g). $^1$H NMR (400 MHz, CHCl$_3$-d): δ 8.53 (d, 1H), 7.78 (dd, 1H), 7.49-7.40 (m, 3H), 7.16 (t, 2H), 6.61 (d, 1H), 6.41 (d, 1H), 4.40 (dd, 1H), 3.95-3.85 (m, 2H), 3.81 (t, 5H), 3.66 (t, 4H), 3.31 (d, 1H), 2.95-2.87 (m, 1H), 2.58 (d, 1H), 2.49-2.41 (m, 3H), 1.20-1.10 (m, 1H), 0.57-0.48 (m, 2H), 0.33-0.22 (m, 2H).

Example 52

(R)-1-(4-Fluorophenyl)-6-(6-morpholin-4-yl-pyridine-3-sulfonyl]-1,4,5,6,7,8-hexahydro-1,2,6-triaza-cyclopenta[b]naphthalene-4a-carboxylic acid cyclobutylmethyl ester

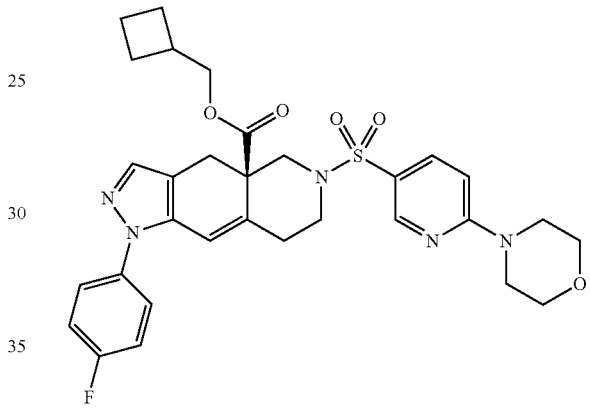

The title compound was prepared by the method of Preparation 48c using (R)-1-(4-fluorophenyl)-6-(6-morpholin-4-yl-pyridine-3-sulfonyl]-1,4,5,6,7,8-hexahydro-1,2,6-triaza-cyclopenta[b]naphthalene-4a-carbonyl chloride and cyclobutanol. LCMS (Method F): 608 (M+H)$^+$, Retention time 5.4 minutes.

Example 53

(R)-1-(4-Fluorophenyl)-6-(6-morpholin-4-yl-pyridine-3-sulfonyl]-1,4,5,6,7,8-hexahydro-1,2,6-triaza-cyclopenta[b]naphthalene-4a-carboxylic acid 3-hydroxycyclobutylmethyl ester

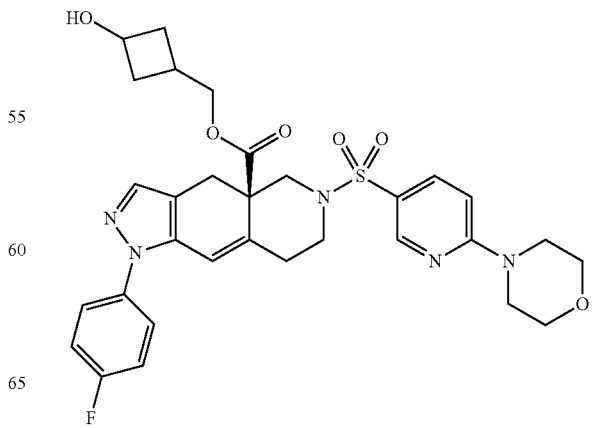

Preparation 53a. (3-Benzyloxy-cyclobutyl)-methanol 3-benzyloxy-cyclobutanecarboxylic acid (1.67 g) in dry tetrahydrofuran (100 mL) was treated with borane-dimethylsulfide complex (1.3 mL) at 50° C. for 16 hours. Water (4 mL) and saturated sodium hydrogen carbonate (3 mL) were added and the mixture was extracted with ethyl acetate. The organic extracts were washed with brine, dried over sodium sulfate and concentrated under reduced pressure. The residue was purified by column chromatography on silica gel, eluting with ethyl acetate in cyclohexane (0 to 1:1 by volume) to give the title compound (1.46 g). $^1$H NMR (400 MHz, CHCl$_3$-d): δ 7.29 (d, 5H), 4.36 (d, 2H), 4.08 (t, 1H), 3.91-3.82 (m, 1H), 3.53 (t, 2H), 2.39-2.30 (m, 1H), 2.33-2.22 (m, 1H), 2.10-2.02 (m, 2H), 1.72-1.63 (m, 1H).

Preparation 53b. (3-Benzyloxy-cyclobutylmethoxy)-tert-butyl-dimethylsilane (3-Benzyloxy-cyclobutyl)-methanol (1.46 g) in N,N-dimethylformamide was treated at 0° C. with imidazole (1.55 g) and tert-butyldimethylsilyl chloride (1.37 g) and allowed to warm to room temperature over 16 hours. The reaction mixture was extracted with ethyl acetate, the organic extracts were washed with brine, dried over sodium sulfate and concentrated under reduced pressure. The residue was purified by column chromatography on silica gel, eluting with ethyl acetate in cyclohexane (0 to 1:9 by volume) to give the title compound (2.24 g).

Preparation 53c. 3-(tert-Butyldimethyl silanoxymethyl)-cyclobutanol (3-Benzyloxy-cyclobutylmethoxy)-tert-butyl-dimethylsilane (2.13 g) in tetrahydrofuran (78 mL) containing 10% palladium-on-carbon was stirred under an atmosphere of hydrogen for 2 hours. Solids were removed by filtration and the filtrate concentrated under reduced pressure to give the title compound (1.56 g).

Preparation 53d. tert-Butyl dimethyl-[3-(tetrahydro-pyran-2-yloxy)-cyclobutylmethoxy]-silane 3-(tert-Butyl dimethylsilanoxymethyl)-cyclobutanol (1.46 g) in dry dichloromethane was treated with dihydropyran (1.7 g) and toluenesulphonic acid (0.01 g) for 3 hours. The reaction mixture was diluted with dichloromethane, the organic extracts were washed with brine, dried over sodium sulfate and concentrated under reduced pressure. The residue was purified by column chromatography on silica gel, eluting with ethyl acetate in cyclohexane (0 to 1:9 by volume) to give the title compound (1.62 g).

Preparation 53e. [3-(Tetrahydro-pyran-2-yloxy)-cyclobutyl]-methanol tert-Butyl dimethyl-[3-(tetrahydropyran-2-yloxy)-cyclobutylmethoxy]-silane (1.62 g) was dissolved in tetrahydrofuran (11 mL) and treated with a solution of 1.0M tetrabutylammonium fluoride in tetrahydrofuran (8.08 mL) for 2 hours. The reaction mixture was diluted with dichloromethane and the mixture was washed with brine, dried over sodium sulfate and concentrated under reduced pressure. The residue was purified by column chromatography on silica gel, eluting with ethyl acetate in cyclohexane (0 to 2:3 by volume) to give the title compound (0.84 g). $^1$H NMR (300 MHz, CHCl$_3$-d): δ 4.62-4.54 (m, 1H), 4.29-4.20 (m, 1H), 3.88 (d, 1H), 3.68-3.60 (m, 2H), 3.53-3.42 (m, 1H), 2.30-2.20 (m, 2H), 2.19-2.08 (m, 2H), 1.86-1.72 (m, 3H), 1.58-1.47 (m, 4H), 1.34 (s, 1H).

Preparation 53f. (R)-1-(4-Fluorophenyl)-6-(6-morpholin-4-yl-pyridine-3-sulfonyl]-1,4,5,6,7,8-hexahydro-1,2,6-triaza-cyclopenta[b]naphthalene-4a-carboxylic acid 3-(tetrahydropyran-2yloxy)-cyclobutylmethyl ester The title compound was prepared by the method of Preparation 48c using (R)-1-(4-fluorophenyl)-6-(6-morpholin-4-yl-pyridine-3-sulfonyl]-1,4,5,6,7,8-hexahydro-1,2,6-triaza-cyclopenta[b]naphthalene-4a-carbonyl chloride and [3-(tetrahydro-pyran-2-yloxy)-cyclobutyl]-methanol. LCMS (Method G): 624.1 (M+H)$^+$, Retention time 4.06 minutes.

Preparation 53g. (R)-1-(4-Fluorophenyl)-6-(6-morpholin-4-yl-pyridine-3-sulfonyl]-1,4,5,6,7,8-hexahydro-1,2,6-triaza-cyclopenta[b]naphthalene-4a-carboxylic acid 3-hydroxycyclobutylmethyl ester A solution of (R)-1-(4-fluorophenyl)-6-(6-morpholin-4-yl-pyridine-3-sulfonyl]-1,4,5,6,7,8-hexahydro-1,2,6-triaza-cyclopenta[b]naphthalene-4a-carboxylic acid 3-(tetrahydro-pyran-2yloxy)-cyclobutylmethyl ester in tetrahydrofuran (0.6 mL) was treated with 4.0 M hydrogen chloride in dioxan (1.0 mL) for 30 minutes. The reaction mixture was evaporated under reduced pressure, the residue dissolved in dichloromethane and the solution washed with 2.0M sodium carbonate solution and brine. The organic extracts were dried over sodium sulfate and concentrated under reduced pressure. The residue was purified by preparative reverse-phase HPLC eluting with a mixture of acetonitrile and water containing 0.1% formic acid (2:3 to 85:15 by volume) to give the title compound as a white solid (0.007 g). $^1$H NMR (400 MHz, CHCl$_3$-d): δ 8.52 (d, 1H), 7.77 (dd, 1H), 7.40-7.30 (m, 3H), 7.18-7.10 (m, 2H), 6.62 (d, 1H), 6.42 (d, 1H), 4.38-4.30 (m, 2H), 4.11 (dd, 2H), 3.80 (t, 5H), 3.66 (t, 4H), 3.27 (d, 1H), 2.88-2.80 (m, 1H), 2.58 (d, 1H), 2.48-2.34 (m, 4H), 2.18-2.06 (m, 4H).

Example 54

(R)-1-(4-Fluorophenyl)-6-(6-morpholin-4-yl-pyridine-3-sulfonyl]-1,4,5,6,7,8-hexahydro-1,2,6-triaza-cyclopenta[b]naphthalene-4a-carboxylic acid 3-methyloxetan-3-ylmethyl ester

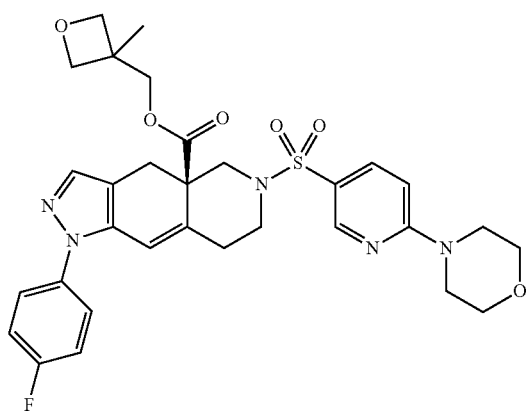 [SMILES: CC1(COC(=O)[C@]23Cc4cnn(-c5ccc(F)cc5)c4C=C2CCN(S(=O)(=O)c2ccc(N4CCOCC4)nc2)C3)COC1]

Preparation 54a. (R)-1-(4-Fluorophenyl)-6-(6-morpholin-4-yl-pyridine-3-sulfonyl]-1,4,5,6,7,8-hexahydro-1,2,6-triaza-cyclopenta[b]naphthalene-4a-carboxylic acid The title compound was prepared by the method of Preparation 48a using (R)-1-(4-fluorophenyl)-6-(6-morpholin-4-yl-pyridine-3-sulfonyl]-1,4,5,6,7,8-hexahydro-1,2,6-triaza-cyclopenta[b]naphthalene-4a-carboxylic acid methyl ester. LCMS (Method G): 540.2 (M+H)+, Retention time 3.10 minutes.

Preparation 54b. (R)-1-(4-Fluorophenyl)-6-(6-morpholin-4-yl-pyridine-3-sulfonyl]-1,4,5,6,7,8-hexahydro-1,2,6-triaza-cyclopenta[b]naphthalene-4a-carboxylic acid 3-methyloxetan-3-ylmethyl ester A solution of (R)-1-(4-fluorophenyl)-6-(6-morpholin-4-yl-pyridine-3-sulfonyl]-1,4,5,6,7,8-hexahydro-1,2,6-triaza-cyclopenta[b]naphthalene-4a-carboxylic acid (0.09 g) in N,N-dimethylformamide (1 mL) was treated with cesium carbonate (0.16 g) and 3-methyl-3-methylbromo-oxetane (0.14 g) at room temperature for 30 minutes. The reaction mixture was diluted with water and the precipitate collected by filtration and dried under vacuum. The solid was purified by preparative reverse-phase HPLC eluting with a mixture of methanol and water containing 0.1% formic acid (3:2 to 4:1 by volume) to give the title compound as a white solid (0.02 g). $^1$H NMR (400 MHz, CHCl$_3$-d): δ 8.53 (d, 1H), 7.78 (dd, 1H), 7.49-7.41 (m, 3H), 7.16 (t, 2H), 6.62 (d, 1H), 6.45 (s, 1H), 4.49-4.38 (m, 3H), 4.34 (dd, 2H), 4.15 (s, 2H), 3.81 (t, 4H), 3.67 (t, 4H), 3.32 (d, 1H), 2.91 (d, 1H), 2.62 (d, 1H), 2.52 (d, 1H), 2.40 (d, 2H), 1.28 (s, 3H).

Example 55

(R)-1-(4-Fluorophenyl)-6-(6-morpholin-4-yl-pyridine-3-sulfonyl]-1,4,5,6,7,8-hexahydro-1,2,6-triaza-cyclopenta[b]naphthalene-4a-carboxylic acid 2-hydroxethyl ester

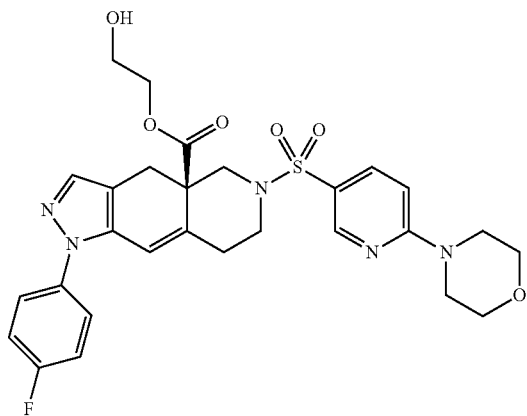 [SMILES: O=C(OCCO)[C@]12Cc3cnn(-c4ccc(F)cc4)c3C=C1CCN(S(=O)(=O)c1ccc(N3CCOCC3)nc1)C2]

Preparation 55a (R)-1-(4-Fluorophenyl)-1,4,7,8-tetrahydro-1,2,6-triaza-cyclopenta[b]naphthalene-4a,6-dicarboxylic acid-6-tert-butylester-4a-[3-(tert-butyl-dimethylsilanoxy)-ethyl ester The title compound was prepared by the method of Preparation 51b using (R)-1-(4-fluorophenyl)-1,4,7,8-hexahydro-1,2,6-triaza-cyclopenta[b]naphthalene-4a,6-dicarboxylic acid 6-tert-butyl ester and (2-bromo-ethoxy)-tert-butyldimethylsilane to afford the title compound as a yellow gum (0.09 g). LCMS (Method G): 572.3 (M+H)+, Retention time 5.11 minutes.

Preparation 55b. (R)-6-(6-Chloropyridine-3-sulfonyl)-1-(4-fluorophenyl)-1,4,5,6,7,8-tetrahydro-1,2,6-triaza-cyclopenta[b]naphthalene-4a-dicarboxylic acid-2-hydroxyethyl ester The title compound was prepared by the method of Preparation 1c using (R)-1-(4-fluorophenyl)-1,4,7,8-tetrahydro-1,2,6-triaza-cyclopenta[b]naphthalene-4a,6-dicarboxylic acid-6-tert-butylester-4a-[3-(tert-butyl-dimethylsilanoxy)-ethyl ester and 2-chloropyridyl-5-sulfonyl chloride to give the title compound. LCMS (Method G): 533 (M+H)+, Retention time 3.33 minutes.

Preparation 55c. (R)-1-(4-Fluorophenyl)-6-(6-morpholin-4-yl-pyridine-3-sulfonyl]-1,4,5,6,7,8-hexahydro-1,2,6-triaza-cyclopenta[b]naphthalene-4a-carboxylic acid-2-hydroxethyl ester The title compound was prepared by the method of Example 20 using (R)-6-(6-chloropyridine-3-sulfonyl)-1-(4-fluorophenyl)-1,4,5,6,7,8-hexahydro-1,2,6-triaza-cyclopenta[b]naphthalene-4a-carboxylic acid 2-hydroxyethyl ester (0.057 g) and morpholine (0.1 g) to give the title compound (0.049 g). $^1$H NMR (400 MHz, CHCl$_3$-d): δ 8.52 (d, 1H), 7.76 (dd, 1H), 7.48-7.37 (m, 3H), 7.16 (t, 2H), 6.62 (d, 1H), 6.43 (d, 1H), 4.59 (dt, 1H), 4.46 (dd, 1H), 4.05 (dt, 1H), 3.89-3.78 (m, 6H), 3.67 (t, 4H), 3.31 (d, 1H), 3.15 (s, 1H), 2.90-2.82 (m, 1H), 2.65-2.58 (m, 1H), 2.44-2.36 (m, 3H).

Example 56

(R)-1-(4-Fluorophenyl)-6-(6-morpholin-4-yl-pyridine-3-sulfonyl]-1,4,5,6,7,8-hexahydro-1,2,6-triaza-cyclopenta[b]naphthalene-4a-carboxylic acid 2-dimethylaminoethyl ester

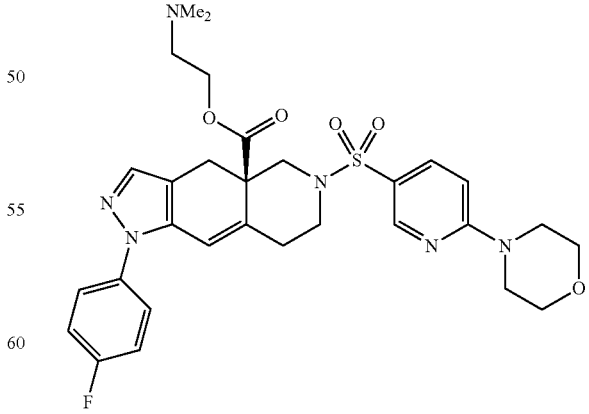

The title compound was prepared by the method of Preparation 48c using (R)-1-(4-fluorophenyl)-6-(6-morpholin-4-yl-pyridine-3-sulfonyl]-1,4,5,6,7,8-hexahydro-1,2,6-triazacyclopenta[b]naphthalene-4a-carbonyl chloride and 2-dimethylamino ethanol. LCMS (Method F): 610 (M+H)+, Retention time 3.4 minutes.

Example 57

(R)-1-(4-Fluorophenyl)-6-(6-morpholin-4-yl-pyridine-3-sulfonyl]-1,4,5,6,7,8-hexahydro-1,2,6-triaza-cyclopenta[b]naphthalene-4a-carboxylic acid 5-methylisoxazol-3-ylmethyl ester

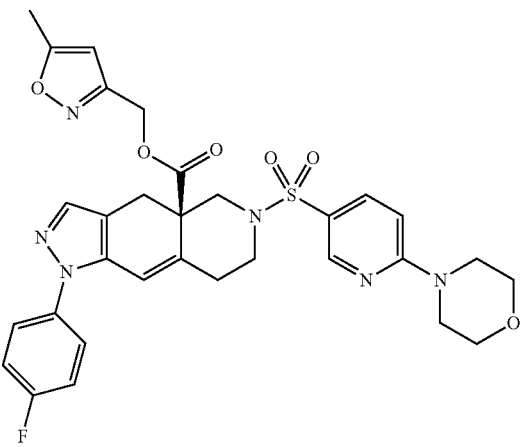 [SMILES: Cc1cc(COC(=O)[C@]23Cc4cnn(-c5ccc(F)cc5)c4C=C2CCN(S(=O)(=O)c2ccc(N4CCOCC4)nc2)C3)no1]

The title compound was prepared by the method of Preparation 54b using (R)-1-(4-fluorophenyl)-6-(6-morpholin-4-yl-pyridine-3-sulfonyl]-1,4,5,6,7,8-hexahydro-1,2,6-triaza-cyclopenta[b]naphthalene-4a-carboxylic acid and 3-chloromethyl-5-methyl isoxazole. LCMS (Method F): 635 (M+H)+, Retention time 4.90 minutes.

Example 58

(R)-1-(4-Fluorophenyl)-6-(6-morpholin-4-yl-pyridine-3-sulfonyl]-1,4,5,6,7,8-hexahydro-1,2,6-triaza-cyclopenta[b]naphthalene-4a-carboxylic acid cyclopropylmethyl ester

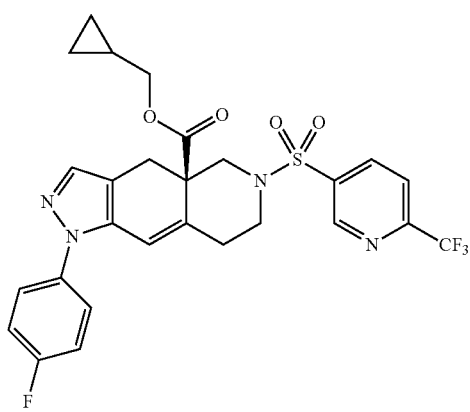 [SMILES: O=C(OCC1CC1)[C@]12Cc3cnn(-c4ccc(F)cc4)c3C=C1CCN(S(=O)(=O)c1ccc(C(F)(F)F)nc1)C2]

The title compound was prepared by the method of Preparation 1c using (R)-1-(4-fluorophenyl)-1,4,7,8-hexahydro-1,2,6-triaza-cyclopenta[b]naphthalene-4a,6-dicarboxylic acid 6-tert-butyl ester 4a-cyclopropylmethyl ester and 6-(trifluoromethyl)pyridine-3-sulfonyl chloride to give the title compound. $^1$H NMR (400 MHz, CHCl$_3$-d): δ 9.10 (d, 1H), 8.29 (dd, 1H), 7.87 (d, 1H), 7.41-7.30 (m, 3H), 7.16 (t, 2H), 6.45 (d, 1H), 4.49 (dd, 1H), 3.99-3.91 (m, 3H), 3.32 (d, 1H), 2.94-2.86 (m, 1H), 2.58-2.51 (m, 4H), 1.09-1.02 (m, 1H), 0.52 (dd, 2H), 0.21 (dd, 2H).

Example 59

(R)-1-(4-Fluorophenyl)-6-(6-methoxy pyridine-3-sulfonyl)-1,4,5,6,7,8-hexahydro-1,2,6-triaza-cyclopenta[b]naphthalene-4a-carboxylic acid cyclobutylmethyl ester

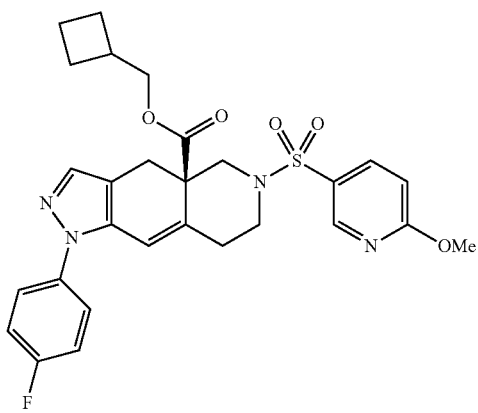 [SMILES: COc1ccc(S(=O)(=O)N2CCC3=Cc4c(cnn4-c4ccc(F)cc4)C[C@]3(C(=O)OCC3CCC3)C2)cn1]

Preparation 59a. (R)-6-(6-Chloropyridine-3-sulfonyl)-1-(4-fluorophenyl)-1,4,5,6,7,8-hexahydro-1,2,6-triaza-cyclopenta[b]naphthalene-4a-carboxylic acid methyl ester The title compound was prepared by the method of Preparation 1c using (R)-1-(4-fluorophenyl)-1,4,7,8-tetrahydro-1,2,6-triaza-cyclopenta[b]naphthalene-4a,6-dicarboxylic acid 6-tert-butylester 4a-methyl ester. LCMS (Method G): 503.1 (M+H)+, Retention time 3.65 minutes.

Preparation 59b. (R)-1-(4-Fluorophenyl)-6-(6-methoxy pyridine-3-sulfonyl)-1,4,5,6,7,8-hexahydro-1,2,6-triaza-cyclopenta[b]naphthalene-4a-carboxylic acid methyl ester A solution of (R)-6-(6-chloropyridine-3-sulfonyl)-1-(4-fluorophenyl)-1,4,5,6,7,8-hexahydro-1,2,6-triaza-cyclopenta[b]naphthalene-4a-carboxylic acid methyl ester (0.3 g) in methanol (10 mL) was treated with cesium carbonate (0.98 g) and water (0.5 mL) for 20 hours. The reaction mixture was diluted with water, extracted with ethyl acetate, the combined organic extracts dried over sodium sulfate and the residue concentrated under reduced pressure to provide a white foam (0.28 g). LCMS (Method G): 499.1 (M+H)+, Retention time 3.77 minutes.

Preparation 59c. (R)-1-(4-Fluorophenyl)-6-(6-methoxy pyridine-3-sulfonyl)-1,4,5,6,7,8-hexahydro-1,2,6-triaza-cyclopenta[b]naphthalene-4a-carboxylic acid The title compound was prepared by the method of Preparation 48a using (R)-1-(4-fluorophenyl)-6-(6-methoxy pyridine-3-sulfonyl]-1,4,5,6,7,8-hexahydro-1,2,6-triaza-cyclopenta[b]naphthalene-4a-carboxylic acid methyl ester. LCMS (Method G): 485.2 (M+H)+, Retention time 3.26 minutes.

Preparation 59d. (R)-1-(4-Fluorophenyl)-6-(6-methoxy pyridine-3-sulfonyl)-1,4,5,6,7,8-hexahydro-1,2,6-triaza-cyclopenta[b]naphthalene-4a-carboxylic acid cyclobutylmethyl ester The title compound was prepared by the method of Preparation 54b using (R)-1-(4-fluorophenyl)-6-(6-methoxy pyridine-3-sulfonyl]-1,4,5,6,7,8-hexahydro-1,2,6-triaza-cyclopenta[b]naphthalene-4a-carboxylic acid and cyclobutylmethyl bromide. $^1$H NMR (400 MHz, CHCl$_3$-d): δ 8.59 (d, 1H), 7.89 (dd, 1H), 7.45-7.37 (m, 3H), 7.16 (t, 2H), 6.84 (d, 1H), 6.42 (d, 1H), 4.40 (dd, 1H), 4.06 (dd, 2H), 4.01 (s, 3H), 3.89-3.81 (m, 1H), 3.28 (d, 1H), 2.88-2.81 (m, 1H), 2.58-2.51 (m, 4H), 2.03-1.92 (m, 2H), 1.79-1.70 (m, 4H).

Example 60

(R)-1-(4-Fluorophenyl)-6-[6-((R)-3-fluoropyrrolidin-1-yl)-pyridine-3-sulfonyl]-1,4,5,6,7,8-hexahydro-1,2,6-triaza-cyclopenta[b]naphthalene-4a-carboxylic acid 5-methylisoxazol-3-ylmethyl ester

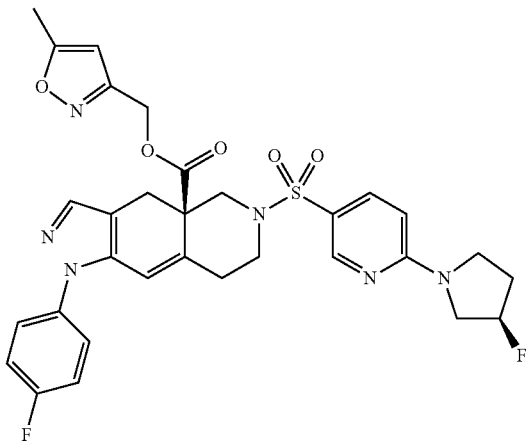 [SMILES: Cc1cc(COC(=O)[C@]23CC(C=N)=C(Nc4ccc(F)cc4)C=C2CCN(S(=O)(=O)c2ccc(N4CC[C@@H](F)C4)nc2)C3)no1]

Preparation 60a. (R)-1-(4-Fluorophenyl)-6-[6-((R)-3-fluoropyrrolidin-1-yl)-pyridine-3-sulfonyl]-1,4,5,6,7,8-hexahydro-1,2,6-triaza-cyclopenta[b]naphthalene-4a-carboxylic acid methyl ester The title compound was prepared by the method of Example 20 using (R)-6-(6-chloropyridine-3-sulfonyl)-1-(4-fluorophenyl)-1,4,5,6,7,8-hexahydro-1,2,6-triaza-cyclopenta[b]naphthalene-4a-carboxylic acid methyl ester and (R)-3-fluoropyrrolidine hydrochloride. LCMS (Method G): 556.2 (M+H)+, Retention time 3.4 minutes.

Preparation 60b. (R)-1-(4-Fluorophenyl)-6-[6-((R)-3-fluoropyrrolidin-1-yl)-pyridine-3-sulfonyl]-1,4,5,6,7,8-hexahydro-1,2,6-triaza-cyclopenta[b]naphthalene-4a-carboxylic acid The title compound was prepared by the method of Preparation 48a using (R)-1-(4-fluorophenyl)-6-[6-((R)-3-fluoropyrrolidin-1-yl)-pyridine-3-sulfonyl]-1,4,5,6,7,8-hexahydro-1,2,6-triaza-cyclopenta[b]naphthalene-4a-carboxylic acid methyl ester. LCMS (Method F): 542 (M+H)+, Retention time 3.4 minutes.

Preparation 60c. (R)-1-(4-Fluorophenyl)-6-[6-((R)-3-fluoropyrrolidin-1-yl)-pyridine-3-sulfonyl]-1,4,5,6,7,8-hexahydro-1,2,6-triaza-cyclopenta[b]naphthalene-4a-carboxylic acid 5-methylisoxazol-3-ylmethyl ester The title compound was prepared by the method of Preparation 54b using (R)-1-(4-Fluorophenyl)-6-[6-((R)-3-fluoropyrrolidin-1-ye-pyridine-3-sulfonyl]-1,4,5,6,7,8-hexahydro-1,2,6-triaza-cyclopenta[b]naphthalene-4a-carboxylic acid and 3-chloromethyl-5-methyl isoxazole. NMR (400 MHz, CHCl$_3$-d): δ 8.53 (d, 1H), 7.74 (dd, 1H), 7.38-7.32 (m, 3H), 7.15 (t, 2H), 6.49-6.40 (m, 2H), 5.94 (d, 1H), 5.46 (s, 1H), 5.33 (s, 1H), 5.17 (s, 2H), 4.39 (dd, 1H), 3.91-3.58 (m, 3H), 3.31 (d, 1H), 2.96-2.88 (m, 1H), 2.59 (d, 1H), 2.50-2.35 (d, 7H), 2.30-2.10 (m, 2H).

Example 61

(R)-1-(4-Fluorophenyl)-6-[6-((R)-3-fluoropyrrolidin-1-yl)-pyridine-3-sulfonyl]-1,4,5,6,7,8-hexahydro-1,2,6-triaza-cyclopenta[b]naphthalene-4a-carboxylic acid 3-hydroxy cyclobutylmethyl ester

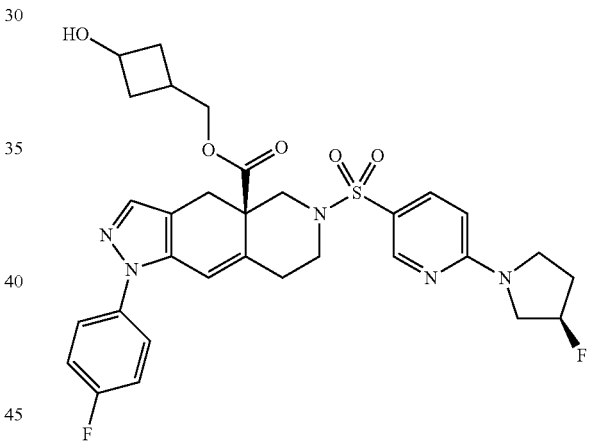

Preparation 61a. (R)-1-(4-Fluorophenyl)-6-[6-((R)-3-fluoropyrrolidin-1-yl)-pyridine-3-sulfonyl]-1,4,5,6,7,8-hexahydro-1,2,6-triaza-cyclopenta[b]naphthalene-4a-carbonyl chloride The title compound was prepared by the method of Preparation 48b using (R)-1-(4-fluorophenyl)-6-[6-((R)-3-fluoropyrrolidin-1-yl)-pyridine-3-sulfonyl]-1,4,5,6,7,8-hexahydro-1,2,6-triaza-cyclopenta[b]naphthalene-4a-carboxylic acid.

Preparation 61b. (R)-1-(4-Fluorophenyl)-6-[6-((R)-3-fluoropyrrolidin-1-yl)-pyridine-3-sulfonyl]-1,4,5,6,7,8-hexahydro-1,2,6-triaza-cyclopenta[b]naphthalene-4a-carboxylic acid-3-(tetrahydro-pyran-2yloxy)-cyclobutylmethyl ester The title compound was prepared by the method of Preparation 48b using (R)-1-(4-fluorophenyl)-6-[6-((R)-3-fluoropyrrolidin-1-yl)-pyridine-3-sulfonyl]-1,4,5,6,7,8-hexahydro-1,2,6-triaza-cyclopenta[b]naphthalene-4a-carbonyl chloride and [3-(tetrahydro-pyran-2-yloxy)-cyclobutyl]-methanol. LCMS (Method G): 626.6 (M+H)$^+$, Retention time 4.10 minutes.

Preparation 61c. (R)-1-(4-Fluorophenyl)-6-[6-((R)-3-fluoropyrrolidin-1-yl)-pyridine-3-sulfonyl]-1,4,5,6,7,8-hexahydro-1,2,6-triaza-cyclopenta[b]naphthalene-4a-carboxylic acid 3-hydroxy cyclobutylmethyl ester The title compound was prepared by the method of Preparation 53g using (R)-1-(4-fluorophenyl)-6-[6-((R)-3-fluoro-pyrrolidin-1-ye-pyridine-3-sulfonyl]-1,4,5,6,7,8-hexahydro-1,2,6-triaza-cyclopenta[b]naphthalene-4a-carboxylic acid-3-(tetrahydro-pyran-2yloxy)-cyclobutylmethyl ester. $^1$H NMR (400 MHz, CHCl$_3$-d): δ 8.53 (d, 1H), 7.75 (dd, 1H), 7.51-7.40 (m, 3H), 7.16 (td, 2H), 6.41 (d, 2H), 5.40 (d, 1H), 4.39-4.22 (m, 2H), 4.12-3.97 (m, 2H), 3.9-3.80 (m, 2H), 3.73 (d, 1H), 3.65-3.58 (m, 2H), 3.29 (dd, 1H), 2.93-2.82 (m, 1H), 2.60 (dd, 1H), 2.48 (d, 2H), 2.48-2.37 (m, 3H), 2.17-2.04 (m, 3H), 1.84-1.70 (m, 2H).

Example 62

(S)-1-[(S)-1-(4-Fluorophenyl)-6-[6-morpholin-4-yl-pyridine-3-sulfonyl]-1,4,5,6,7,8-hexahydro-1,2,6-triaza-cyclopenta[b]naphthalene-4a-ylmethyl]-pyrrolidin-3-ol

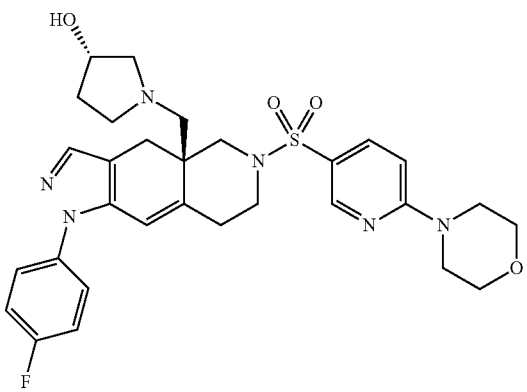 [SMILES: N=CC1=C(Nc2ccc(F)cc2)C=C2CCN(S(=O)(=O)c3ccc(N4CCOCC4)nc3)C[C@@]2(CN2CC[C@H](O)C2)C1]

A solution of (R)-1-(4-fluorophenyl)-6-[6-morpholin-4-yl-pyridine-3-sulfonyl]-1,4,5,6,7,8-hexahydro-1,2,6-triaza-cyclopenta[b]naphthalene-4a-carbaldehyde (0.074 g) in dry dichloroethane (2.8 mL) was treated with (S)-pyrrolidin-3-ol (0.062 g) and 4A powdered molecular sieves (0.14 g) for 4 hours. Sodium triacetoxyborohydride (0.045 g) was added and the reaction mixture stirred for 20 hours. The reaction mixture was diluted with dichloromethane, washed with saturated aqueous sodium hydrogen carbonate solution and brine. The organic extracts were dried over sodium sulphate and concentrated under reduced pressure. The residue was purified by preparative reverse-phase HPLC eluting with a mixture of acetonitrile and water containing 0.1% formic acid (1:19 to 7:3 by volume) to give the title compound as a white solid (0.025 g). $^1$H NMR (400 MHz, CHCl$_3$-d): δ 8.54 (d, 1H), 8.24 (s, 1H), 7.81 (dd, 1H), 7.43-7.32 (m, 3H), 7.16 (t, 2H), 6.63 (d, 1H), 6.28 (d, 1H), 4.40 (s, 1H), 4.30 (d, 1H), 3.90 (d, 1H), 3.81 (t, 4H), 3.67 (t, 4H), 3.36-3.23 (m, 2H), 3.13-3.01 (m, 3H), 2.78-2.63 (m, 2H), 2.54 (d, 1H), 2.44-2.25 (m, 3H), 2.24-2.13 (m, 2H), 1.90 (dt, 1H).

Example 63

(R)-1-[(S)-1-(4-Fluorophenyl)-6-[6-morpholin-4-yl-pyridine-3-sulfonyl)-1,4,5,6,7,8-hexahydro-1,2,6-triaza-cyclopenta[b]naphthalene-4a-ylmethyl]-pyrrolidin-3-ol

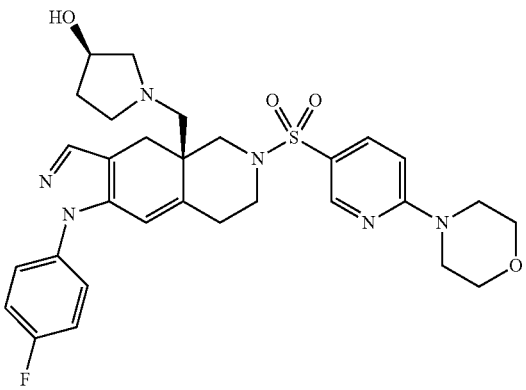 [SMILES: N=CC1=C(Nc2ccc(F)cc2)C=C2CCN(S(=O)(=O)c3ccc(N4CCOCC4)nc3)C[C@@]2(CN2CC[C@@H](O)C2)C1]

The title compound was prepared by the method of Preparation 62 using (R)-1-(4-fluorophenyl)-6-[6-morpholin-4-yl-pyridine-3-sulfonyl)-1,4,5,6,7,8-hexahydro-1,2,6-triaza-cyclopenta[b]naphthalene-4a-carbaldehyde and (R)-pyrrolidin-3-ol. LCMS (Method F): 595 (M+H)$^+$, Retention time 3.2 minutes.

Example 64

(R)-1-(4-Fluoro-phenyl)-4a-(2-methoxy-ethoxymethyl)-6-(6-morpholin-4-yl-pyridine-3-sulfonyl)-4,4a,5,6,7,8-hexahydro-1H-1,2,6-traza-cyclopenta[b]naphthalene

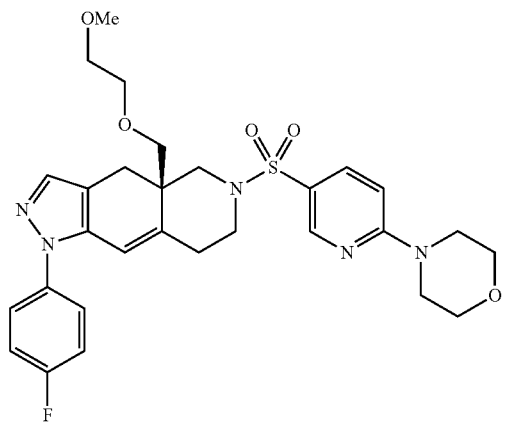 [SMILES: COCCOC[C@]12Cc3cnn(-c4ccc(F)cc4)c3C=C1CCN(S(=O)(=O)c1ccc(N3CCOCC3)nc1)C2]

The title compound was prepared by the method of Preparation 20a using (R)-6-(6-chloropyridine-3-sulfonyl)-1-(4-fluorophenyl)-4a-(2-methoxyethoxymethyl)-4,4a,5,6,7,8-hexahydro-1,2,6-triaza-cyclopenta[b]naphthalene and morpholine. $^1$H NMR (400 MHz, CHCl$_3$-d): δ 8.54 (d, 1H), 7.80 (dd, 1H), 7.41-7.39 (m, 3H), 7.15 (t, 2H), 6.62 (d, 1H), 6.27 (d, 1H), 4.17-4.15 (m, 1H), 3.81 (t, 5H), 3.60-3.57 (m, 8H), 3.38 (s, 3H), 3.25 (d, 1H), 3.14 (d, 1H), 2.76-2.63 (m, 1H), 2.43-2.33 (m, 2H), 2.21 (s, 1H), 2.10 (d, 1H), 1.26 (t, 1H).

Example 65

Glucocorticoid Receptor Binding Assay

The following is a description of an assay for determining the inhibition of dexamethasone binding of the Human Recombinant Glucocorticoid Receptor:

Binding protocol: Compounds were tested in a binding displacement assay using human recombinant glucocorticoid receptor with $^3$H-dexamethasone as the ligand. The source of the receptor was recombinant baculovirus-infected insect cells. This GR was a full-length steroid hormone receptor likely to be associated with heat-shock and other endogenous proteins.

The assay was carried out in v-bottomed 96-well polypropylene plates in a final volume of 200 μl containing 0.5 nM GR solution, 2.5 nM 3H-dexamethasone (Amersham TRK 645) in presence of test compounds, test compound vehicle (for total binding) or excess dexamethasone (20 μM, to determine non-specific binding) in an appropriate volume of assay buffer.

For the Primary Screen, test compounds were tested at 1 μM in duplicate. These compounds were diluted from 10 mM stock in 100% DMSO. After dilution to 100 μM, 5 μl were added to 245 μl assay buffer to obtained 2 μM compound and 2% DMSO.

For the $IC_{50}$ determinations, test compounds were tested at 6 concentrations in duplicate (concentration range depends on % inhibition binding that was obtained in the Primary Screen). Test compounds were diluted from 10 mM stock in 100% DMSO. The tested solutions were prepared at 2× final assay concentration in 2% DMSO/assay buffer.

All reagents and the assay plate were kept on ice during the addition of reagents. The reagents were added to wells of a v-bottomed polypropylene plate in the following order: 50 μl of 10 nM 3H-dexamethasone solution, 100 μl of TB/NSB/compound solution and 50 μl of 2 nM GR solution. After the additions, the incubation mixture was mixed and incubated for 2.5 hrs at 4° C.

After 2.5 hrs incubation, unbound counts were removed with dextran coated charcoal (DCC) as follows: 25 μl of DCC solution (10% DCC in assay buffer) was added to all wells and mixed (total volume 225 μl). The plate was centrifuged at 4000 rpm for 10 minutes at 4° C. 75 μl of the supernatants (i.e. ⅓ of total volume) was carefully pipetted into an optiplate. 200 μl of scintillation cocktail were added (Microscint-40, Packard Bioscience. B.V.). The plate was vigorously shaken for approx. 10 minutes and counted on Topcount.

For the $IC_{50}$ determinations, the results were calculated as % inhibition [$^3$H]-dexamethasone bound and fitted to sigmoidal curves (fixed to 100 and 0) to obtain $IC_{50}$ values (concentration of compound that displaces 50% of the bound counts). The $IC_{50}$ values were converted to $K_i$ (the inhibition constant) using the Cheng-Prusoff equation. Test results are presented in Table1. Compounds with a $K_i$ value less than 0.5 nM are designated with +++; compounds with a $K_i$ value between 0.5 and 1.0 nM are designated with ++; compounds with a $K_i$ greater than 1.0 nM are designated with +.

Reagents: Assay buffer: 10 mM potassium phosphate buffer pH 7.6 containing 5 mM DTT, 10 mM sodium molybdate, 100 μM EDTA and 0.1% BSA.

Example 66

GR Functional Assay Using SW1353/MMTV-5 Cells

SW1353/MMTV-5 is an adherent human chondrosarcoma cell line that contains endogenous glucocorticoid receptors. It was transfected with a plasmid (pMAMneo-Luc) encoding firefly luciferase located behind a glucocorticoid-responsive element (GRE) derived from a viral promoter (long terminal repeat of mouse mammary tumor virus). A stable cell line SW1353/MMTV-5 was selected with geneticin, which was required to maintain this plasmid. This cell line was thus sensitive to glucocorticoids (dexamethasone) leading to expression of luciferase ($EC_{50}^{dex}$ 10 nM). This dexamethasone-induced response was gradually lost over time, and a new culture from an earlier passage was started (from a cryo-stored aliquot) every three months.

In order to test for a GR-antagonist, SW1353/MMTV-5 cells were incubated with several dilutions of the compounds in the presence of 5×$EC_{50}^{dex}$ (50 nM), and the inhibition of induced luciferase expression was measured using a luminescence in a Topcounter (LucLite kit from Perkin Elmer). For each assay, a dose-response curve for dexamethasone was prepared in order to determine the $EC_{50}^{dex}$ required for calculating the $K_i$ from the $IC_{50}$'s of each tested compound. Test results are presented in Table 1 for selected compounds of the Invention. GR Functional compounds with a $K_i$ value less than 10 nM are designated with +++, compounds with a $K_i$ value between 10 nM and 50 nM are designated with ++; and compounds with a $K_i$ value greater than 50 nM are designated with +.

SW1353/MMTV-5 cells were distributed in 96-well plates and incubated in medium (without geneticin) for 24 hrs (in the absence of $CO_2$). Dilutions of the compounds in medium +50 nM dexamethasone were added and the plates further incubated for another 24 hrs after which the luciferase expression is measured.

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

What is claimed is:
1. A compound having the formula:

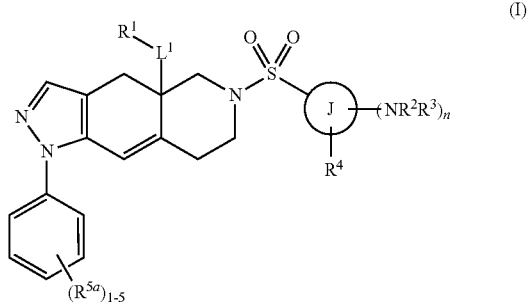

wherein

L¹ is selected from the group consisting of a bond, —C(O)O—C$_{0-6}$ alkylene, C$_{1-6}$ alkylene and C$_{1-6}$ heteroalkylene;

R¹ is selected from the group consisting of hydrogen, C$_{1-6}$ alkyl, C$_{1-6}$ haloalkyl, C$_{1-6}$ heteroalkyl, C$_{3-8}$ cycloalkyl, C$_{3-8}$ heterocycloalkyl, aryl, heteroaryl, —OR$^{1a}$, NR$^{1c}$R$^{1d}$, and —C(O)NR$^{1c}$R$^{1d}$, wherein the cycloalkyl, heterocycloalkyl, aryl and heteroaryl groups are optionally substituted with hydrogen, C$_{1-6}$ alkyl, hydroxy and C$_{1-6}$ alkoxy;

each R$^{1a}$ is independently selected from the group consisting of hydrogen, C$_{1-6}$ alkyl, C$_{1-6}$ haloalkyl, C$_{1-6}$ heteroalkyl, C$_{3-8}$ cycloalkyl, C$_{1-6}$alkylC$_{3-8}$ cycloalkyl, C$_{3-8}$ heterocycloalkyl, C$_{1-6}$alkylC$_{3-8}$ heterocycloalkyl, aryl, C$_{1-6}$ alkylaryl, heteroaryl and C$_{1-6}$ alkylheteroaryl;

each of R$^{1c}$ and R$^{1d}$ are independently selected from the group consisting of hydrogen, C$_{1-6}$ alkyl, C$_{1-6}$ heteroalkyl, C$_{3-8}$ cycloalkyl, C$_{3-8}$ heterocycloalkyl, aryl, and heteroaryl;

alternatively, R$^{1c}$ and R$^{1d}$ are combined to form a C$_{3-8}$ heterocycloalkyl having from 1 to 3 heteroatoms each independently selected from the group consisting of N, O and S, and optionally substituted with 1 to 3 groups each independently selected from the group consisting of hydrogen, C$_{1-6}$ alkyl, hydroxy and C$_{1-6}$ alkoxy;

ring J is a heteroaryl ring having from 5 to 6 ring members and from 1 to 3 heteroatoms each independently selected from the group consisting of N, O and S, wherein at least one heteroatom is N;

each of R² and R³ are independently selected from the group consisting of hydrogen, C$_{1-6}$ alkyl, C$_{2-6}$ alkenyl, C$_{2-6}$ alkynyl, C$_{1-6}$ haloalkyl, C$_{1-6}$ heteroalkyl, C$_{3-8}$ cycloalkyl, C$_{3-8}$ heterocycloalkyl, aryl and heteroaryl;

R⁴ is selected from the group consisting of hydrogen, halogen, C$_{1-6}$ alkyl, C$_{2-6}$ alkenyl, C$_{2-6}$ alkynyl, C$_{1-6}$ haloalkyl, C$_{1-6}$ alkoxy, C$_{1-6}$ haloalkoxy, C$_{1-6}$ heteroalkyl, C$_{3-8}$ cycloalkyl, C$_{3-8}$ heterocycloalkyl, aryl and heteroaryl;

alternatively R² is combined with R³ or R⁴ to form a C$_{3-8}$ heterocycloalkyl having from 1 to 3 heteroatoms each independently selected from the group consisting of N, O and S, and optionally substituted with 1 to 3 R$^{2a}$ groups, wherein each R$^{2a}$ is independently selected from the group consisting of hydrogen, C$_{1-6}$ alkyl, halogen, C$_{1-6}$ haloalkyl, hydroxy, C$_{1-6}$ alkoxy, C$_{1-6}$ haloalkoxy, nitro, cyano, C$_{3-8}$ cycloalkyl, C$_{3-8}$ heterocycloalkyl, aryl and heteroaryl;

subscript n is 0 or 1;

each R$^{5a}$ is independently selected from the group consisting of hydrogen, halogen, —OR$^{5a1}$, —NR$^{5a2}$R$^{5a3}$, —S(O$_2$)NR$^{5a2}$R$^{5a3}$, —CN, C$_{1-6}$ alkyl, C$_{2-6}$ alkenyl, C$_{2-6}$ alkynyl, C$_{1-6}$ haloalkyl, C$_{1-6}$ heteroalkyl, C$_{3-8}$ cycloalkyl, C$_{3-8}$ heterocycloalkyl, aryl, and heteroaryl;

each of R$^{5a1}$, R$^{5a2}$ and R$^{5a3}$ are independently selected from the group consisting of hydrogen, C$_{1-6}$ alkyl, C$_{1-6}$ heteroalkyl, C$_{3-8}$ cycloalkyl, C$_{3-8}$ heterocycloalkyl, aryl, and heteroaryl;

wherein when R⁴ is hydrogen, subscript n is 1;

and salts and isomers thereof.

2. The compound of claim 1, having the formula:

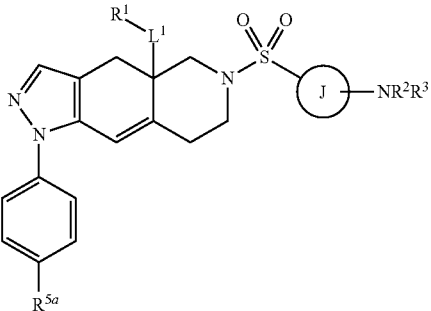

wherein each of R² and R³ is independently selected from the group consisting of H and C$_{1-6}$ alkyl;

alternatively, R² is combined with R³ to form a C$_{3-8}$ heterocycloalkyl having from 1 to 3 heteroatoms each independently selected from the group consisting of N, O and S, and optionally substituted with 1 to 3 R$^{2a}$ groups, wherein each R$^{2a}$ is independently selected from the group consisting of hydrogen, C$_{1-6}$ alkyl, halogen, C$_{1-6}$ haloalkyl, hydroxy, C$_{1-6}$ alkoxy, C$_{1-6}$ haloalkoxy, nitro, cyano, C$_{3-8}$ cycloalkyl, C$_{3-8}$ heterocycloalkyl, aryl and heteroaryl; and R$^{5a}$ is halogen.

3. The compound of claim 1, wherein

L¹ is selected from the group consisting of —C(O)O—, —C(O)O—C$_{1-6}$ alkylene, and C$_{1-6}$ alkylene;

R¹ is selected from the group consisting of C$_{1-6}$ alkyl, C$_{3-8}$ cycloalkyl, C$_{3-8}$ heterocycloalkyl, heteroaryl, and —OR$^{1a}$, wherein the cycloalkyl, heterocycloalkyl and heteroaryl groups are optionally substituted with hydrogen, C$_{1-6}$ alkyl, hydroxy and C$_{1-6}$ alkoxy; and each R$^{1a}$ is independently selected from the group consisting of hydrogen, C$_{1-6}$ alkyl, C$_{1-6}$ haloalkyl, C$_{1-6}$ heteroalkyl, C$_{3-8}$ cycloalkyl, C$_{1-6}$alkylC$_{3-8}$ cycloalkyl, C$_{3-8}$ heterocycloalkyl, C$_{1-6}$alkylC$_{3-8}$ heterocycloalkyl, aryl, C$_{1-6}$ alkylaryl, heteroaryl and C$_{1-6}$ alkylheteroaryl.

4. The compound of claim 3, wherein the group L¹-R¹ is selected from the group consisting of —CH$_2$R¹, —CH$_2$OR$^{1a}$, —C(O)OR¹ and —C(O)O—CH$_2$—R¹.

5. The compound of claim 4, wherein the group L¹-R¹ is selected from the group consisting of methoxymethyl, ethoxymethyl, (difluoromethoxy)methyl, (cyclopropylmethoxy)methyl, (2-methoxyethoxy)methyl, (2-hydroxyethoxy)methyl, (oxazol-2-ylmethoxy)methyl, ((5-methylisoxazol-3-yl)methoxy)methyl, N-(2-hydroxyethyl)-N-methyl-aminomethyl, (3-hydroxy-pyrrolidin-1-yl)methyl, methyl carboxylate, ethyl carboxylate, isopropyl carboxylate, cyclobutyl carboxylate, cyclopropylmethyl carboxylate, cyclobutylmethyl carboxylate, (3-hydroxycyclobutyl)methyl carboxylate, (3-methyloxetan-3-yl)methyl carboxylate, 2-hydroxyethyl carboxylate, 2-(dimethylamino)ethyl carboxylate, and (5-methylisoxazol-3-yl)methyl carboxylate.

6. The compound of claim 1, wherein ring J is selected from the group consisting of pyrrole, imidazole, pyrazole, thiazole, isothiazole, oxazole, isoxazole, pyridine, pyrazine, pyrimidine and pyridazine.

7. The compound of claim 1, wherein ring J is selected from the group consisting of pyrid-2-yl, pyrid-3-yl and pyrid-4-yl.

8. The compound of claim 1, having the formula:

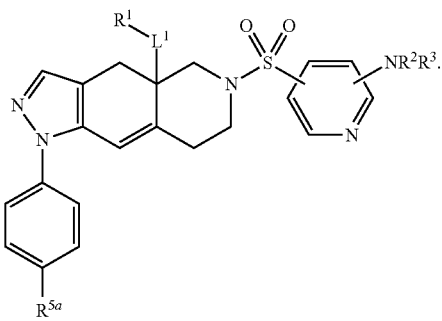

9. The compound of claim 1, wherein $R^2$ is combined with $R^3$ to form a $C_{3-8}$ heterocycloalkyl having from 1 to 2 heteroatoms each independently selected from the group consisting of N and O, and optionally substituted with 1 to 3 $R^{2a}$ groups, wherein each $R^{2a}$ is independently selected from the group consisting of $C_{1-6}$ alkyl, halogen, $C_{1-6}$ haloalkyl, hydroxy, $C_{1-6}$ alkoxy and $C_{1-6}$ haloalkoxy.

10. The compound of claim 9, wherein $R^2$ is combined with $R^3$ to form a $C_{3-8}$ heterocycloalkyl selected from the group consisting of azetidine, pyrrolidine, imidazolidine, pyrazolidine, oxazolidine, isoxazolidine, piperidine, piperazine, morpholine, azepane, homopiperazine, azacyclooctane, quinuclidine, 1,4-diazabicyclo[2.2.2]octane and 2-oxa-5-azabicyclo[2.2.1]heptane, each optionally substituted with 1 $R^{2a}$ group selected from the group consisting of halogen and hydroxy.

11. The compound of claim 10, wherein $R^2$ is combined with $R^3$ to form a $C_{3-8}$ heterocycloalkyl selected from the group consisting of azetidin-1-yl, pyrrolidin-1-yl, piperidin-1-yl, morpholin-1-yl and 2-oxa-5-azabicyclo[2.2.1]heptan-5-yl, wherein the azetidin-1-yl, pyrrolidin-1-yl, and piperidin-1-yl are each optionally substituted with 1 $R^{2a}$ group selected from the group consisting of F and hydroxy.

12. The compound of claim 11, wherein $R^2$ is combined with $R^3$ to form a $C_{3-8}$ heterocycloalkyl selected from the group consisting of azetidin-1-yl, 3-fluoro-azetidin-1-yl, 3-hydroxy-azetidin-1-yl, pyrrolidin-1-yl, 3-hydroxy-pyrrolidin-1-yl, 3-fluoro-pyrrolidin-1-yl, morpholin-1-yl and 2-oxa-5-azabicyclo[2.2.1]heptan-5-yl.

13. The compound of claim 1, wherein $R^{5a}$ is F.

14. The compound of claim 1, having the formula:

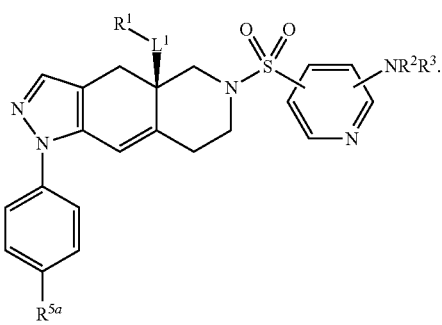

15. The compound of claim 1, having the formula:

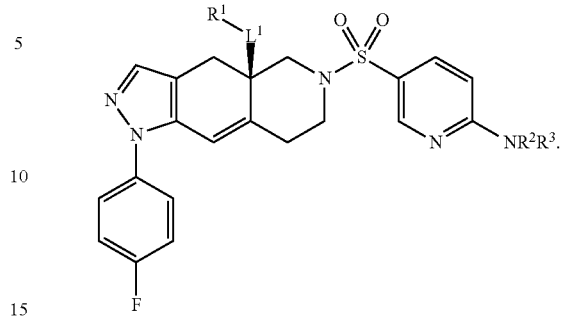

16. The compound of claim 1, wherein subscript n is 0.

17. The compound of claim 1, selected from the group consisting of:
- (R)-4a-Ethoxymethyl-1-(4-fluorophenyl)-6-[[6-(4-morpholinyl)-3-pyridinyl]sulfonyl]-1,4,7,8-tetrahydro-1,2,6-triazacyclopenta[b]naphthalene,
- (R)-1-(4-Fluorophenyl)-6-(6-morpholin-4-ylpyridine-3-sulfonyl)-1,4,5,6,7,8-hexahydro-1,2,6-triazacyclopenta[b]naphthalene-4a-carboxylic acid methyl ester,
- [(R)-1-(4-Fluorophenyl)-6-[[6-(4-morpholinyl)-3-pyridinyl]sulfonyl]-1,4,7,8-tetrahydro-1,2,6-triazacyclopenta[b]naphthalen-4a-yl]methanol,
- (R)-4a-Ethoxymethyl-1-(4-fluorophenyl)-6-[[3-pyridinyl]sulfonyl]-1,4,7,8-tetrahydro-1,2,6-triazacyclopenta[b]naphthalene,
- (R)-4a-Ethoxymethyl-1-(4-fluorophenyl)-6-[[2H-pyrido[3.2-b]-1,4-oxazin-7-yl]sulfonyl]-1,4,7,8-tetrahydro-1,2,6-triazacyclopenta[b]naphthalene,
- (R)-4a-Ethoxymethyl-1-(4-fluorophenyl)-6-[[6-(1-pyrrolidinyl)-3-pyridinyl]sulfonyl]-1,4,7,8-tetrahydro-1,2,6-triazacyclopenta[b]naphthalene,
- (R)-1-(4-Fluorophenyl)-4a-methoxymethyl-6-[[6-(1-pyrrolidinyl)-3-pyridinyl]sulfonyl]-1,4,7,8-tetrahydro-1,2,6-triazacyclopenta[b]naphthalene,
- (R)-6-[[6-(1-Azetidinyl)-3-pyridinyl]sulfonyl]-4a-ethoxymethyl-1-(4-fluorophenyl)-1,4,7,8-tetrahydro-1,2,6-triazacyclopenta[b]naphthalene,
- (R)-4a-Ethoxymethyl-1-(4-fluorophenyl)-6-[[6-methylamino-3-pyridinyl]sulfonyl]-1,4,7,8-tetrahydro-1,2,6-triazacyclopenta[b]naphthalene,
- (R)-6-[[6-Dimethylamino-3-pyridinyl]sulfonyl]-4a-ethoxymethyl-1-(4-fluorophenyl)-1,4,7,8-tetrahydro-1,2,6-triazacyclopenta[b]naphthalene,
- (R)-1-(4-Fluorophenyl)-4a-methoxymethyl-6-[[6-methylamino-3-pyridinyl]sulfonyl]-1,4,7,8-tetrahydro-1,2,6-triazacyclopenta[b]naphthalene,
- (R)-6-[[6-Dimethylamino-3-pyridinyl]sulfonyl]-1-(4-fluorophenyl)-4a-methoxymethyl-1,4,7,8-tetrahydro-1,2,6-triazacyclopenta[b]naphthalene,
- (R)-6-[[6-(1-Azetidinyl)-3-pyridinyl]sulfonyl]-1-(4-fluorophenyl)-4a-methoxymethyl-1,4,7,8-tetrahydro-1,2,6-triazacyclopenta[b]naphthalene,
- (R)-1-(4-Fluorophenyl)-4a-methoxymethyl-6-(5-morpholin-4-ylpyridine-3-sulfonyl)-4,4a,5,6,7,8-hexahydro-1H-1,2,6-triazacyclopenta[b]naphthalene,
- (R)-6-(5-Azetidin-1-ylpyridine-3-sulfonyl)-1-(4-fluorophenyl)-4a-methoxymethyl-4,4a,5,6,7,8-hexahydro-1H-1,2,6-triazacyclopenta[b]naphthalene,
- (R)-1-(4-Fluorophenyl)-4a-methoxymethyl-6-(6-morpholin-4-yl-pyridine-3-sulfonyl)-4,4a,5,6,7,8-hexahydro-1H-1,2,6-triazacyclopenta[b]naphthalene, (R)-4a-Difluoromethoxymethyl-1-(4-fluorophenyl)-6-(6-morpholin-4-yl-pyridine-3-sulfonyl)-4,4a,5,6,7,8-hexahydro-1H-1,2,6-triazacyclopenta[b]naphthalene, (R)-6-(6-Azetidin-1-yl-pyridine-3-sulfonyl)-1-(4-fluorophenyl)-4a-(oxazol-2-ylmethoxymethyl)-4,4a,5,6,7,8-hexahydro-1H-1,2,6-triazacyclopenta[b]naphthalene, (R)-6-(6-Azetidin-1-ylpyridine-3-sulfonyl)-4a-difluoromethoxymethyl-1-(4-fluorophenyl)-4,4a,5,6,7,8-hexahydro-1H-1,2,6-triazacyclopenta[b]naphthalene, (R)-1-(4-Fluorophenyl)-4a-methoxymethyl-6-[[6-(1-piperazinyl)-3-pyridinyl]sulfonyl]-1,4,7,8-tetrahydro-1,2,6-triazacyclopenta[b]naphthalene, (R)-1-(4-Fluorophenyl)-4a-methoxymethyl-6-[[6-(1-(4-methylpiperazinyl))-3-pyridinyl]sulfonyl]-1,4,7,8-tetrahydro-1,2,6-triazacyclopenta[b]naphthalene, (R)-1-(4-Fluorophenyl)-6-[6-((R)-3-fluoropyrrolidin-1-yl)-pyridine-3-sulfonyl]-4a-methoxymethyl-4,4a,5,6,7,8-hexahydro-1H-1,2,6-triaza-cyclopenta[b]naphthalene, (R)-1-{5-[(R)-1-(4-Flurophenyl)-4a-methoxymethyl-1,4,4a,5,6,7,8-hexahydro-1,2,6-triaza-cyclopenta[b]naphthalene-6-sulfonyl]-pyridin-2-yl}-pyrrolidin-3-ol, (S)-1-{5-[(R)-1-(4-Flurophenyl)-4a-methoxymethyl-1,4,4a,5,6,7,8-hexahydro-1,2,6-triaza-cyclopenta[b]naphthalene-6-sulfonyl]-pyridin-2-yl}-pyrrolidin-3-ol, (R)-1-(4-Fluorophenyl)-4a-methoxymethyl-6-[(1S,4S)-6-(2-oxa-5-aza-bicyclo[2.2.1]hept-5-yl)pyridine-3-sulfonyl]-4,4a,5,6,7,8-hexahydro-1H-1,2,6-triaza-cyclopenta[b]naphthalene, (R)-1-(4-Fluorophenyl)-4a-methoxymethyl-6-(6-trifluoromethylpyridine-3-sulfonyl)-4,4a,5,6,7,8-hexahydro-1H-1,2,6-triaza-cyclopenta[b]naphthalene, (R)-4a-Cyclopropylmethoxymethyl-1-(4-fluorophenyl)-6-(6-pyrrolidin-1-yl-pyridine-3-sulfonyl)-4,4a,5,6,7,8-hexahydro-1H-1,2,6-triaza-cyclopenta[b]naphthalene, (R)-4a-Cyclopropylmethoxymethyl-1-(4-fluorophenyl)-6-(6-((R)-3-fluoro-pyrrolidin-1-yl)-pyridine-3-sulfonyl)-4,4a,5,6,7,8-hexahydro-1H-1,2,6-triaza-cyclopenta[b]naphthalene, (R)-4a-Cyclopropylmethoxymethyl-1-(4-fluorophenyl)-6-(6-((S)-3-fluoropyrrolidin-1-yl)-pyridine-3-sulfonyl)-4,4a,5,6,7,8-hexahydro-1H-1,2,6-triaza-cyclopenta[b]naphthalene, (R)-1-{5-[(R)-4a-Cyclopropylmethoxymethyl-1-(4-fluorophenyl)-1,4,4a,5,6,7,8-hexahydro-1,2,6-triaza-cyclopenta[b]naphthalene-6-sulfonyl]pyridine-2-yl}-pyrrolidine-3-ol, (S)-1-{5-[(R)-4a-Cyclopropylmethoxymethyl-1-(4-fluorophenyl)-1,4,4a,5,6,7,8-hexahydro-1,2,6-triaza-cyclopenta[b]naphthalene-6-sulfonyl]pyridine-2-yl}-pyrrolidine-3-ol, (R)-4a-Cyclopropylmethoxymethyl-6-[6-(3-fluoroazetin-1-yl)-pyridine-3-sulfonyl]-1-(4-fluorophenyl)-1,4,4a,5,6,7,8-hexahydro-1H-1,2,6-triaza-cyclopenta[b]naphthalene, 1-{5-[(R)-4a-Cyclopropylmethoxymethyl-1-(4-fluorophenyl)-1,4,4a,5,6,7,8-hexahydro-1,2,6-triaza-cyclopenta[b]naphthalene-6-sulfonyl]-pyridin-2-yl}-azetidin-3-ol, (R)-4a-Cyclopropylmethoxymethyl-1-(4-fluorophenyl)-6-(6-morpholin-4-yl-pyridine-3-sulfonyl)-4,4a,5,6,7,8-hexahydro-1H-1,2,6-triaza-cyclopenta[b]naphthalene, (R)-1-(4-Fluorophenyl)-6-[6-((R)-3-fluoropyrrolidin-1-yl)-pyridine-3-sulfonyl]-4a-(2-methoxyethoxymethyl)-4,4a,5,6,7,8-hexahydro-1H-1,2,6-triaza-cyclopenta[b]naphthalene, 2-{(R)-1-(4-Fluorophenyl)-6-[6-((R)-3-fluoropyrrolidin-1-yl)-1,4,5,6,7,8-hexahydro-1,2,6-triaza-cyclopenta[b]naphthalene-4a-ylmethoxy}ethanol, (R)-1-(4-Fluorophenyl)-6-[6-((R)-3-fluoropyrrolidin-1-yl)-pyridine-3-sulfonyl]-4a-(5-methyl-isoxazol-3-ylmethoxymethyl)-4,4a,5,6,7,8-hexahydro-1H-1,2,6-triaza-cyclopenta[b]naphthalene, 1-{5-[(R)-1-(4-Fluorophenyl)-4a-methoxymethyl-1,4,4a,5,6,7,8-hexahydro-1,2,6-triaza-cyclopenta[b]naphthalene-6-sulfonyl]-pyridin-3-yl}-azetidin-3-ol, (R)-6-[5-(3-Fluoroazetidin-1-yl)-pyridine-3-sulfonyl]-1-(4-fluorophenyl)-4a-methoxymethyl-4,4a,5,6,7,8-hexahydro-1H-1,2,6-triaza-cyclopenta[b]naphthalene, (R)-1-{5-[(R)-1-(4-Fluorophenyl)-4a-methoxymethyl-1,4,4a,5,6,7,8-hexahydro-1,2,6-triaza-cyclopenta[b]naphthalene-6-sulfonyl]pyridine-3-yl}-pyrrolidine-3-ol, (S)-1-{5-[(R)-1-(4-Fluorophenyl)-4a-methoxymethyl-1,4,4a,5,6,7,8-hexahydro-1,2,6-triaza-cyclopenta[b]naphthalene-6-sulfonyl]pyridine-3-yl}-pyrrolidine-3-ol, (R)-1-(4-Fluorophenyl)-6-[5-((R)-3-fluoropyrrolidin-1-yl)-pyridine-3-sulfonyl]-4a-methoxymethyl-4,4a,5,6,7,8-hexahydro-1H-1,2,6-triaza-cyclopenta[b]naphthalene, (R)-1-(4-Fluorophenyl)-6-[5-((S)-3-fluoropyrrolidin-1-yl)-pyridine-3-sulfonyl]-4a-methoxymethyl-4,4a,5,6,7,8-hexahydro-1H-1,2,6-triaza-cyclopenta[b]naphthalene, (R)-1-(4-Fluorophenyl)-4a-methoxymethyl-6-(2-pyrrolidin-1-yl-pyridine-4-sulfonyl)-4,4a,5,6,7,8-hexahydro-1H-1,2,6-triaza-cyclopenta[b]naphthalene, (R)-1-{4-[(R)-1-(4-Fluorophenyl)-4a-methoxymethyl-1,4,4a,5,6,7,8-hexahydro-1,2,6-triaza-cyclopenta[b]naphthalene-6-sulfonyl]-pyridin-2-yl}-pyrrolidin-3-ol, (S)-1-{4-KR)-1-(4-Fluorophenyl)-4a-methoxymethyl-1,4,4a,5,6,7,8-hexahydro-1,2,6-triaza-cyclopenta[b]naphthalene-6-sulfonyl]-pyridin-2-yl}-pyrrolidin-3-ol, 2-{[(S)-1-(4-Fluorophenyl)-6-[6-morpholin-4-yl-pyridine-3-sulfonyl)-1,4,5,6,7,8-hexahydro-1,2,6-triaza-cyclopenta[b]naphthalene-4a-ylmethyl]-methylamino}-ethanol, (S)-1-{(S)-1-(4-Fluorophenyl)-6-[6-((R)-3-hydroxy-pyrrolidin-3-ol)-pyridine-3-sulfonyl]-1,4,5,6,7,8-hexahydro-1,2,6-triaza-cyclopenta[b]naphthalene-4a-ylmethyl}-pyrrolidin-3-ol, (S)-1-{(S)-1-(4-Fluorophenyl)-6-[6-((R)-3-fluoro-pyrrolidin-1-yl)-pyridine-3-sulfonyl]-1,4,5,6,7,8-hexahydro-1,2,6-triaza-cyclopenta[b]naphthalene-4a-ylmethyl}-pyrrolidin-3-ol, (R)-1-(4-Fluorophenyl)-6-(6-morpholin-4-yl-pyridine-3-sulfonyl]-1,4,5,6,7,8-hexahydro-1,2,6-triaza-cyclopenta[b]naphthalene-4a-carboxylic acid ethyl ester, (R)-1-(4-Fluorophenyl)-6-(6-morpholin-4-yl-pyridine-3-sulfonyl]-1,4,5,6,7,8-hexahydro-1,2,6-triaza-cyclopenta[b]naphthalene-4a-carboxylic acid isopropyl ester, (R)-1-(4-Fluorophenyl)-6-(6-morpholin-4-yl-pyridine-3-sulfonyl]-1,4,5,6,7,8-hexahydro-1,2,6-triaza-cyclopenta[b]naphthalene-4a-carboxylic acid cyclobutyl ester, (R)-1-(4-Fluorophenyl)-6-(6-morpholin-4-yl-pyridine-3-sulfonyl]-1,4,5,6,7,8-hexahydro-1,2,6-triaza-cyclopenta[b]naphthalene-4a-carboxylic acid cyclopropylmethyl ester, (R)-1-(4-Fluorophenyl)-6-(6-morpholin-4-yl-pyridine-3-sulfonyl]-1,4,5,6,7,8-hexahydro-1,2,6-triaza-cyclopenta[b]naphthalene-4a-carboxylic acid cyclobutylmethyl ester, (R)-1-(4-Fluorophenyl)-6-(6-morpholin-4-yl-pyridine-3-sulfonyl]-1,4,5,6,7,8-hexahydro-1,2,6-triaza-cyclopenta[b]naphthalene-4a-carboxylic acid 3-hydroxycyclobutylmethyl ester, (R)-1-(4-Fluorophenyl)-6-(6-morpholin-4-yl-pyridine-3-sulfonyl]-1,4,5,6,7,8-hexahydro-1,2,6-triaza-cyclopenta[b]naphthalene-4a-carboxylic acid 3-methyloxetan-3-ylmethyl ester, (R)-1-(4-Fluorophenyl)-6-(6-morpholin-4-yl-pyridine-3-sulfonyl]-1,4,5,6,7,8-hexahydro-1,2,6-triaza-cyclopenta[b]naphthalene-4a-carboxylic acid 2-hydroxethyl ester, (R)-1-(4-Fluorophenyl)-6-(6-morpholin-4-yl-pyridine-3-sulfonyl]-1,4,5,6,7,8-hexahydro-1,2,6-triaza-cyclopenta[b]naphthalene-4a-carboxylic acid 2-dimethylaminoethyl ester, (R)-1-(4-Fluorophenyl)-6-(6-morpholin-4-yl-pyridine-3-sulfonyl]-1,4,5,6,7,8-hexahydro-1,2,6-triaza-cyclopenta[b]naphthalene-4a-carboxylic acid 5-methylisoxazol-3-ylmethyl ester, (R)-1-(4-Fluorophenyl)-6-(6-morpholin-4-yl-pyridine-3-sulfonyl]-1,4,5,6,7,8-hexahydro-1,2,6-triaza-cyclopenta[b]naphthalene-4a-carboxylic acid cyclopropylmethyl ester, (R)-1-(4-Fluorophenyl)-6-(6-methoxy pyridine-3-sulfonyl)-1,4,5,6,7,8-hexahydro-1,2,6-triaza-cyclopenta[b]naphthalene-4a-carboxylic acid cyclobutylmethyl ester, (R)-1-(4-Fluorophenyl)-6-[6-((R)-3-fluoropyrrolidin-1-yl)-pyridine-3-sulfonyl]-1,4,5,6,7,8-hexahydro-1,2,6-triaza-cyclopenta[b]naphthalene-4a-carboxylic acid 5-methylisoxazol-3-ylmethyl ester, (R)-1-(4-Fluorophenyl)-6-[6-((R)-3-fluoropyrrolidin-1-yl)-pyridine-3-sulfonyl]-1,4,5,6,7,8-hexahydro-1,2,6-triaza-cyclopenta[b]naphthalene-4a-carboxylic acid 3-hydroxy cyclobutylmethyl ester, (S)-1-[(S)-1-(4-Fluorophenyl)-6-[6-morpholin-4-yl-pyridine-3-sulfonyl)-1,4,5,6,7,8-hexahydro-1,2,6-triaza-cyclopenta[b]naphthalene-4a-ylmethyl]-pyrrolidin-3-ol, (R)-1-[(S)-1-(4-Fluorophenyl)-6-[6-morpholin-4-yl-pyridine-3-sulfonyl)-1,4,5,6,7,8-hexahydro-1,2,6-triaza-cyclopenta[b]naphthalene-4a-ylmethyl]-pyrrolidin-3-ol, or (R)-1-(4-Fluoro-phenyl)-4a-(2-methoxy-ethoxymethyl)-6-(6-morpholin-4-yl-pyridine-3-sulfonyl)-4,4a,5,6,7,8-hexahydro-1H-1,2,6-traza-cyclopenta[b]naphthalene.

18. A pharmaceutical composition, comprising a compound of claim 1 and a pharmaceutically acceptable excipient.

19. A method of antagonizing a glucocorticoid receptor, the method comprising administering to a subject in need thereof, a therapeutically effective amount of a compound of claim 1.

* * * * *